US012753185B2

(12) United States Patent
Ding et al.

(10) Patent No.: US 12,753,185 B2
(45) Date of Patent: Oct. 6, 2026

(54) 2-AMINOPYRIMIDINE COMPOUND AND PHARMACEUTICAL COMPOSITION THEREOF AND APPLICATION THEREOF

(71) Applicants: GUANGZHOU SALUSTIER BIOSCIENCES CO., LTD., Guangdong (CN); JINAN UNIVERSITY, Guangdong (CN)

(72) Inventors: Ke Ding, Guangdong (CN); Shan Li, Guangdong (CN); Zhang Zhang, Guangdong (CN); Hongfei Si, Guangdong (CN); Zhengchao Tu, Guangdong (CN); Xiaomei Ren, Guangdong (CN); Chong Lei, Guangdong (CN); Xia Tang, Guangdong (CN); Yueyi Gao, Guangdong (CN); Shingpan Chan, Guangdong (CN)

(73) Assignees: GUANGZHOU SALUSTIER BIOSCIENCES CO., LTD., Guangdong (CN); JINAN UNIVERSITY, Guangdong (CN)

( * ) Notice: Subject to any disclaimer, the term of this patent is extended or adjusted under 35 U.S.C. 154(b) by 582 days.

(21) Appl. No.: 18/343,732

(22) Filed: Jun. 28, 2023

(65) Prior Publication Data

US 2023/0348487 A1 Nov. 2, 2023

Related U.S. Application Data

(63) Continuation of application No. PCT/CN2021/143765, filed on Dec. 31, 2021.

(30) Foreign Application Priority Data

Jan. 11, 2021 (CN) ........................ 202110032031.5

(51) Int. Cl.
*C07D 493/04* (2006.01)
*A61P 35/00* (2006.01)
*C07D 519/00* (2006.01)

(52) U.S. Cl.
CPC ............ *C07D 493/04* (2013.01); *A61P 35/00* (2018.01); *C07D 519/00* (2013.01)

(58) Field of Classification Search
None
See application file for complete search history.

(56) References Cited

FOREIGN PATENT DOCUMENTS

| | | | |
|---|---|---|---|
| CN | 101370792 | 2/2009 | |
| CN | 102083800 | 6/2011 | |
| CN | 104144915 | 11/2014 | |
| CN | 104974140 | 10/2015 | |
| CN | 108309959 | 7/2018 | |
| CN | 106478651 | 7/2019 | |
| WO | 2007027238 | 3/2007 | |
| WO | WO-2010058032 A2 * | 5/2010 | .............. A61P 43/00 |
| WO | 2015094803 | 6/2015 | |
| WO | 2015148867 | 10/2015 | |
| WO | 2015148869 | 10/2015 | |
| WO | 2021000884 | 1/2021 | |

OTHER PUBLICATIONS

Malatkova and Wsol, "Carbonyl reduction pathways in drug metabolism". Drug Metab Rev, 2014; 46(1): 96-123 (Year: 2014).*

Carmen Vicente et al., "Targeted sequencing identifies associations between IL7R-JAK mutations and epigenetic modulators in T-cell acute lymphoblastic leukemia", Haematologica Oct. 2015, pp. 1301-1310.

Sandrine Degryse et al., "JAK3 mutants transform hematopoietic cells through JAK1 activation, causing T-cell acute lymphoblastic leukemia in a mouse model", Blood, Nov. 2014, pp. 3092-3100.

Sandrine Degryse et al., "Mutant JAK3 signaling is increased by loss of wild-type JAK3 or by acquisition of secondary JAK3 mutations in T-ALL", Blood, Jan. 2018, pp. 421-425.

"International Search Report (Form PCT/ISA/210) of PCT/CN2021/143765," mailed on Apr. 1, 2022, with English translation thereof, pp. 1-10.

"Written Opinion of the International Searching Authority (Form PCT/ISA/237) of PCT/CN2021/143765," mailed on Apr. 1, 2022, pp. 1-4.

* cited by examiner

*Primary Examiner* — Sarah Pihonak
*Assistant Examiner* — Donna M Nestor
(74) *Attorney, Agent, or Firm* — JCIPRNET

(57) ABSTRACT

The present disclosure provides a class of 2-aminopyrimidine compounds with a structure shown in Formula (I) or their pharmaceutically acceptable salts, isotope derivatives, solvates, or their stereoisomers, geometric isomers, tautomers, or prodrug molecules or metabolites and pharmaceutical compositions and application thereof. The compounds of the present disclosure can efficiently and selectively inhibit the kinase activity of Janus Kinase 3 (JAK3), and have strong signal inhibition and cell proliferation inhibition effects on various blood tumor cells (especially human acute myeloid leukemia cell U937 cells) and solid tumor cells. They can be used to prepare anti-tumor drugs and drugs for preventing and treating inflammatory diseases.

(I)

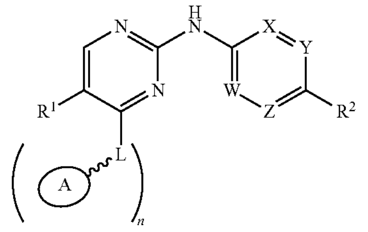

20 Claims, 6 Drawing Sheets

2-AMINOPYRIMIDINE COMPOUND AND PHARMACEUTICAL COMPOSITION THEREOF AND APPLICATION THEREOF

CROSS-REFERENCE TO RELATED APPLICATION

The present application is a continuation of PCT application No. PCT/CN2021/143765, filed on Dec. 31, 2021, which claims the priority of China Patent Application No. 202110032031.5, filed on Jan. 11, 2021. The entirety of each of the above mentioned patent applications is incorporated by reference herein and made a part of this specification.

BACKGROUND

Technical Field

The present disclosure relates to the chemical and pharmaceutical technology, in particular to a class of 2-aminopyrimidine compound and pharmaceutical composition thereof and application thereof.

Description of Related Art

Since the late 1990s, protein tyrosine kinases have received increasing attention as emerging targets. Under normal circumstances, these proteins with tyrosine kinase activity bind to ATP and undergo phosphorylation on tyrosine residues at specific positions, which subsequently activates and transduces important signaling pathways within cells, and participate in regulating life processes such as cell division, growth, proliferation, differentiation, aging, and apoptosis, etc. The disorder of tyrosine kinase can cause cellular dysfunction and lead to a series of diseases in the body, including tumors and inflammatory diseases. Therefore, targeting protein tyrosine kinases has become an important aspect of precision medicine.

Protein tyrosine kinases include receptor tyrosine kinases and non-receptor tyrosine kinases. The protein structure of receptor tyrosine kinases includes extracellular ligand binding regions, hydrophobic transmembrane regions, intracellular tyrosine kinase catalytic domains and regulatory sequences. The subcellular localization of non-receptor tyrosine kinases is different from that of receptor tyrosine kinases, excluding extracellular and transmembrane structures. They are a class of cytoplasmic tyrosine kinase proteins. After being activated in cells, non-receptor tyrosine kinase binds to downstream signaling molecules, activates them and phosphorylates them to exert tyrosine kinase activity. Janus kinase (JAK) is a non-receptor tyrosine kinase family consisting of four members: JAK1, JAK2, JAK3, and Tyk2. Since the protein structure of this type of kinase contains two kinase domains, which are the "true" kinase domain that binds to ATP and exerts kinase catalytic activity, and the pseudo kinase domain that has no catalytic activity, this type of kinase is named after the two-faced Roman god Janus. The binding of extracellular specific ligands (such as cytokines, driving factors, growth factors, etc.) to receptors will lead to the activation of JAKs and phosphorylation of JAKs-related receptors. After receptor phosphorylation, the recruitment of corresponding STATs (signal transducers and transcriptional activators) is initiated by recognition of the SH2 domain containing a specific sequence, followed by phosphorylation of STATs proteins. After homodimerization or heterodimerization, phosphorylated STATs transfer to the nucleus, bind to specific DNA binding sites, and regulate gene transcription, which leads to changes in cellular function.

In contrast to the ubiquitous expression of JAK1, JAK2, and Tyk2, JAK3 is exclusively expressed in hematopoietic cells, wherein it associates with the γ-common chain (γc) to release γc cytokines (i.e., IL-2, IL-4, IL-7, IL-9, IL-15, and IL-21), promoting the proximity, dimerization and self-phosphorylation of JAK3 related receptors and JAK1 related receptors. The activated JAK3 protein recruits STAT1, STAT3, STAT5, or STAT6 and then phosphorylates them. In canonical JAK-STAT signalling, STATs undergo JAK-mediated phosphorylation of their tyrosine residues, leading to STAT dimerization, nuclear translocation, DNA binding and target gene induction, participating in important life processes such as the growth, proliferation, development, and differentiation of lymphocytes, T cells, B cells, and NK cells, as well as immune regulation. Many clinical studies have found that loss of function in human JAK3 can lead to severe comprehensive immune deficiency (SCID), while overactivation or mutation is associated with many autoimmune diseases and cancers, especially hematological cancers such as leukemia. Research has found that the JAK3-STAT5 signaling cascade is an important signaling pathway in the hematopoietic process. In cases of T-ALL (T-lymphocytic leukemia), the probability of abnormalities in this signaling pathway is as high as 27.7%; wherein, JAK3 is the most common mutated gene in this pathway, accounting for approximately 16.1% of T-ALL cases (Haematologica 2015, 100, 1301-1310). As the most common activation mutation of JAK3, JAK3 (M511I) exhibits cytokine independent cell proliferation and transformation ability in Ba/F3 cells; in the bone marrow transplant mouse model, mice transplanted with JAK3 (M511I) mutated hematopoietic cells showed significant clinical symptoms of T-ALL (a sharp increase in white blood cell count, enlargement of the spleen, thymus, and lymph nodes, and an increase in CD8+ T cells in peripheral blood and hematopoietic tissues), while mice transplanted with wild-type JAK3 cells did not develop any disease (*Blood* 2014, 124, 3092-3100). In addition, research shows that about ⅓ of T-ALL cases with JAK3 mutations contain two JAK3 mutations (homozygote mutations or two different mutations); the occurrence of dual mutations in 293T cells and Ba/F3 cell models showed stronger pathway activation and cell transformation ability, posing a greater threat to hematogenic tumor activity (*Blood* 2018, 131, 421-425). Therefore, JAK3 has become a potential new target for the treatment of hematological tumors, and the development of small molecule inhibitors targeting JAK3 will provide important strategies for alleviating or treating related diseases.

At present, eight JAK inhibitors have been approved by FDA, EMEA or MHLW, namely: Ruxolitinib (JAK1/JAK2 inhibitor approved by the FDA in 2011), Tofacitinib (pan JAK inhibitor approved by the FDA in 2012), and Baricitinib (JAK1/JAK2 inhibitor approved by the EMEA and FDA in 2017 and 2018), Peficitinib (pan JAK inhibitor approved by MHLW in 2019), Fedratinib (JAK2 inhibitor approved by the FDA in 2019), Upadacitinib (JAK1 inhibitor approved by the FDA in 2019), Delgocitinib (pan JAK inhibitor approved by MHLW in 2020), Filgotinib (JAK1 inhibitor approved by EMEA and MHLW in 2020), Abrocitinib (JAK1 inhibitor approved by the FDA in 2022), Pacritinib (JAK2 inhibitor approved by the FDA in 2022), Deucravacitinib (Tyk2 inhibitor approved by the FDA in 2022). Among them, five drugs (Ruxolitinib, Tofatinib, Baricitinib, Upadacitinib, and Fedratinib) approved by the FDA have been given black box warnings due to potential serious side effects in clinical practice. Therefore, developing highly selective JAK3 inhibitors can effectively reduce toxic side effects by reducing interference with numerous unrelated cytokine pathways while maintaining therapeutic efficacy.

Although the research and development of highly selective JAK inhibitors will be the direction and trend of molecular optimization by pharmaceutical chemists in the future, it is difficult to find highly selective ATP competitive inhibitors among the JAKs family because the protein structure of the JAKs family has high sequence homology, especially the highest homology observed in the ATP catalytic domain; in addition, JAK3 has a higher ATP affinity compared to other family members, leading to challenges in the development of selective JAK3 inhibitors, but it's not impossible. By comparing the specific amino acid sequences of ATP binding pockets, it was found that JAK3 kinase contains a unique cysteine residue (Cys909) that has lipophilic function and can covalently bind with nucleophilic reagents, while it is serine in the equivalent position in the other three JAK members. Based on this, Pfizer has developed a highly selective JAK3 irreversible inhibitor PF-06651600 through a structure-based drug design strategy ($IC_{50}$ value of the kinase at 1 mM ATP concentration: JAK3 is 33.1 nM, while other subtypes are greater than 10 μM). At present, this compound is in phase III clinical trials for the treatment of alopecia areata and has been recognized as a breakthrough therapy by the US FDA. So far, there is no JAK3 selective inhibitor entering clinical application, and the development of JAK3 small molecule inhibitors with high activity and low toxicity for the treatment of inflammatory diseases or hematological tumors has important clinical significance.

In summary, there is an urgent need to develop new types of small molecule compounds in this field, especially those with novel skeletons, to solve the current problems of low selectivity and high toxicity of JAK inhibitors in clinical practice, and to address clinical needs.

SUMMARY

In response to the above-mentioned issues, the present disclosure provides a new class of 2-aminopyrimidine compounds, which can selectively inhibit the activity of JAK3 kinase with high activity, thereby inhibiting the proliferation of various tumor cells, and it can be used for the treatment of tumors or inflammatory diseases related to JAK3 kinase. The detailed technical solution is as follows:

2-aminopyrimidine compounds with the structure shown in Formula (I) or their pharmaceutically acceptable salts, isotope derivatives, solvates, or their stereoisomers, geometric isomers, tautomers, or prodrug molecules or metabolites:

(I)

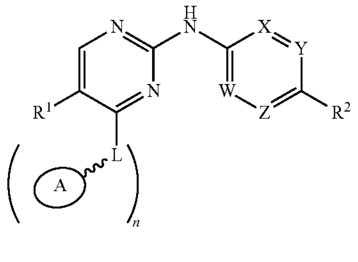

wherein,

R1 is selected from: H, halogen, cyano, one or more R11 substituted or unsubstituted C1-C6 alkyl groups, one or more R11 substituted or unsubstituted C3-C6 cycloalkyl groups, one or more R11 substituted or unsubstituted C1-C6 alkoxy groups, one or more R11 substituted or unsubstituted C3-C6 cycloalkoxy groups, formamide groups;

R2 is selected from: H, halogen, —(CH2)mNR3R4, —(CH2)mCR3R4R5 or —(CH2)mOCR3R4R5; wherein, each m is independently 0, 1, 2, or 3; each R3 and each R4 are independently selected from: H, one or more R12 substituted C1-C6 alkyl groups, or R3, R4, together with the attached N or C to form a 3-12 membered single ring, fused ring, bridge ring, or spiral ring substituted by one or more R12 with ring atoms containing 0, 1, 2, or 3 heteroatoms; R5 is selected from: H, cyano or C1-C3 alkyl; each R12 is independently selected from: H, halogen, hydroxyl, amino, C1-C3 alkyl, C1-C3 alkyl substituted by —C(═O)NHR13, hydroxy substituted C1-C3 alkyl, C1-C3 alkyl substituted by C3-C6 cycloalkyl group, C3-C8 heterocyclic group substituted C1-C3 alkyl group, C1-C3 alkoxy, —NHR13, —N(R13)2, —C(═O)R13, R13 substituted or unsubstituted 4-8-membered single ring, fused ring, bridge ring, or spiral ring containing 0, 1, 2, or 3 heteroatoms; R13 is a C1-C3 alkyl group; the heteroatom is O, S, and/or N;

W, X, Y, and Z are independently N or —CR6; wherein, R6 is selected from: hydrogen, halogen, one or more R11 substituted or unsubstituted C1-C3 alkyl groups, one or more R11 substituted or unsubstituted C1-C3 alkoxy groups, —NH—CN, —NHC(O)—CR7=CR8R9, —NHS(O)2-CR7=CR8R9; R7, R8, and R9 are independently selected from: H, cyano, one or more R11 substituted or unsubstituted C1-C6 alkyl groups;

n is 0 or 1;

L is O or S;

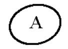

is a 4-12 membered saturated or partially saturated single ring, bridge ring, spiral ring, or fused ring substituted with one or more R10 with ring atoms containing 0, 1, 2, or 3 heteroatoms; wherein, each R10 is independently selected from: hydrogen, halogen, hydroxyl, one or more R11 substituted or unsubstituted C1-C3 alkyl groups, one or more R11 substituted or unsubstituted C1-C3 alkoxy groups, and the heteroatoms are O, S, and/or N;

R11 is selected from: halogen, hydroxyl, amino, C1-C3 alkyl, C1-C3 alkoxy, —NHR13, —N (R13) 2, —C(═O) R13.

In some embodiments,

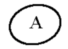

is an 8-10 saturated or partially saturated fused double ring substituted by one or more $R^{10}$ and containing 1, 2, or 3 oxygen atoms.

In some embodiments,

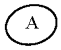

is selected from the following groups:

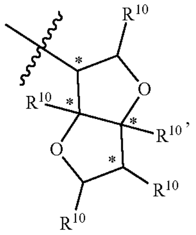,
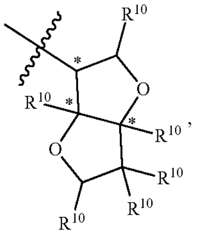,
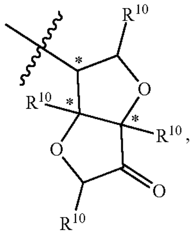,
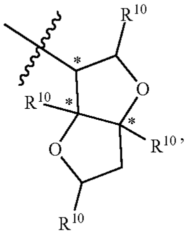, wherein, the configurations of chiral carbon atoms labeled with * are independently S or R configurations.

In some embodiments,

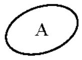

is selected from the following groups:

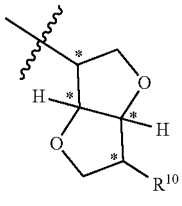,
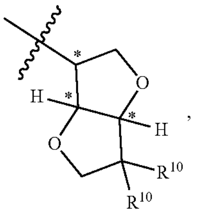,
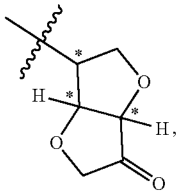,
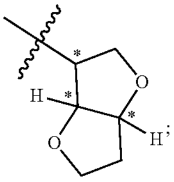;

wherein, the configurations of chiral carbon atoms labeled with * are independently S or R configurations, and each $R^{10}$ is independently selected from: halogen, hydroxyl, $C_1$-$C_3$ alkyl, $C_1$-$C_3$ alkoxy.

In some embodiments,

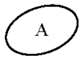

is selected from the following groups:

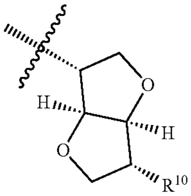
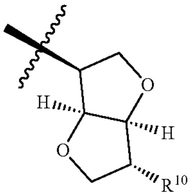
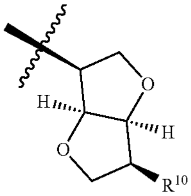
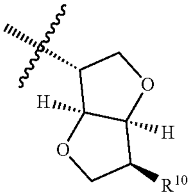
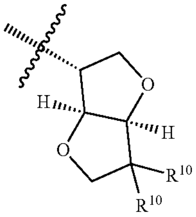
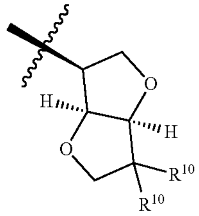
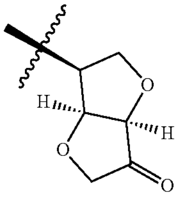
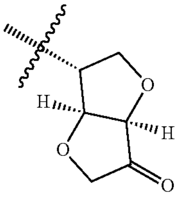
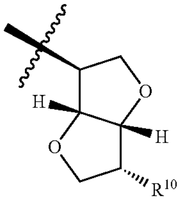
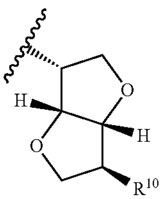
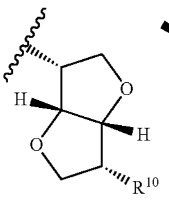
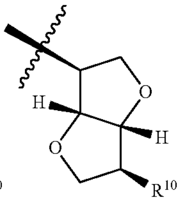
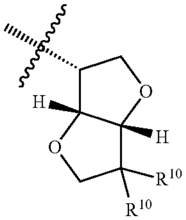
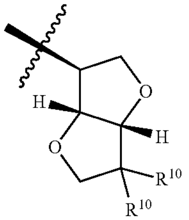
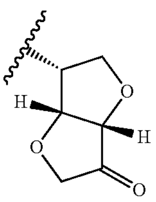
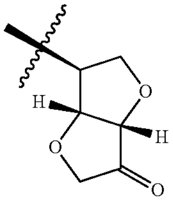

-continued
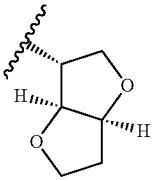
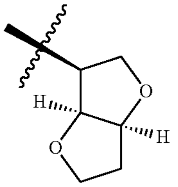
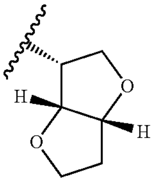
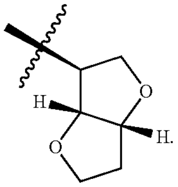
In some embodiments,
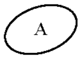
is selected from the following groups:
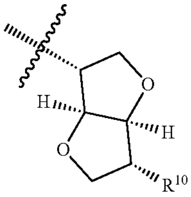
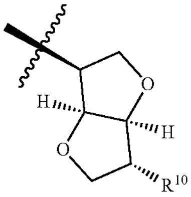
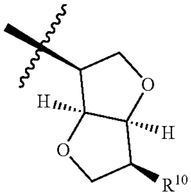
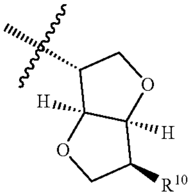
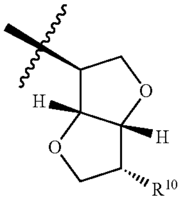
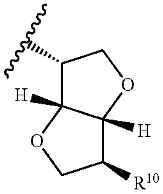
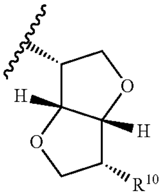
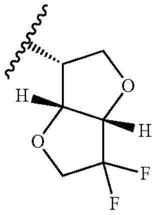
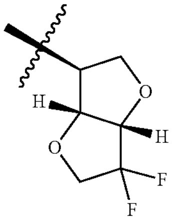
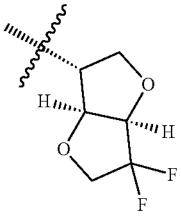
-continued
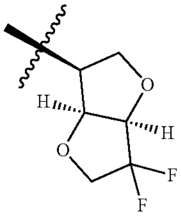
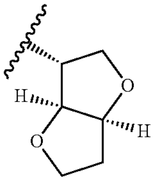
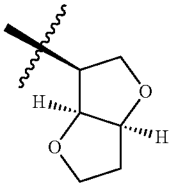
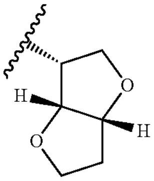
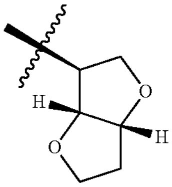
wherein, each $R^{10}$ is independently selected from: F, hydroxyl, methyl, methoxy, ethoxy, and isopropoxy.
In some embodiments,
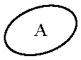
is selected from the following groups:
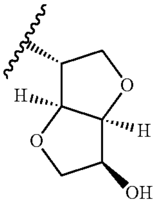
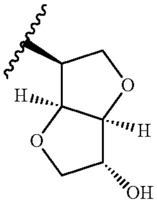
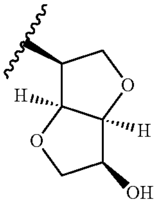
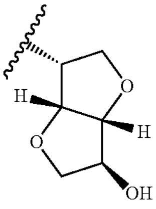
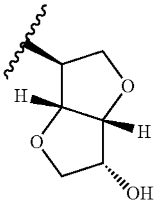
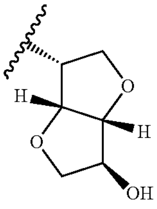
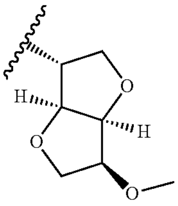
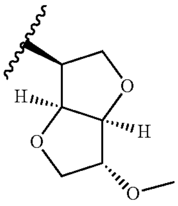

-continued
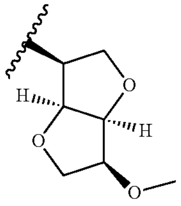 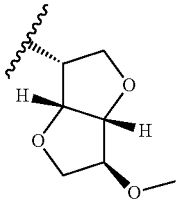
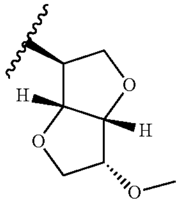 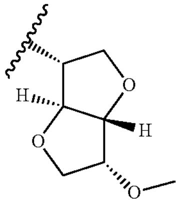
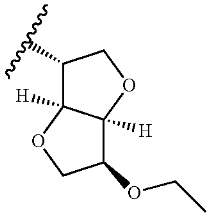 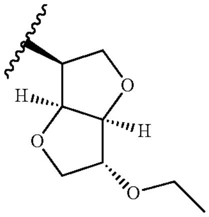
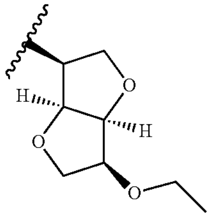 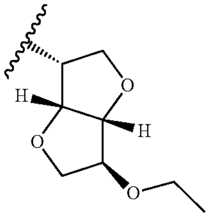
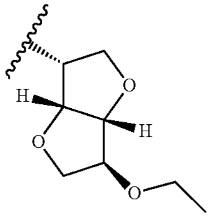 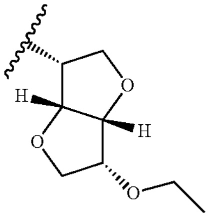
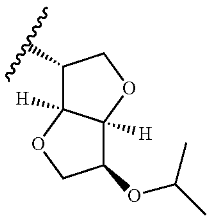 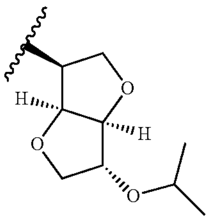
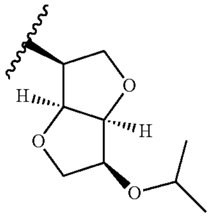 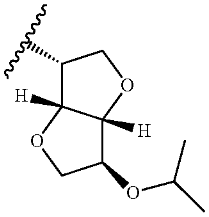
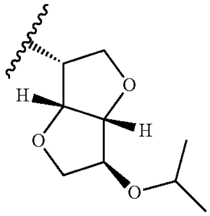 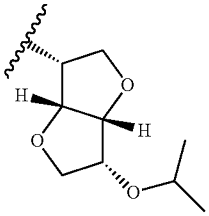
-continued
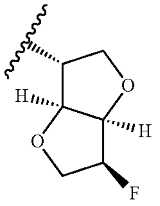 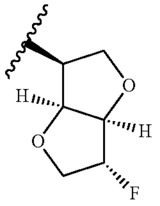 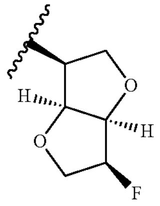
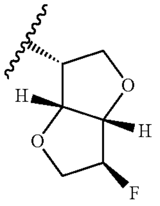 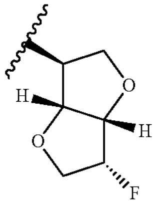 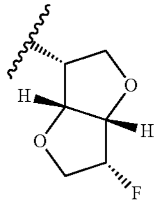
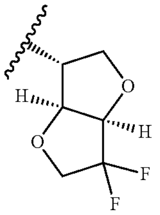 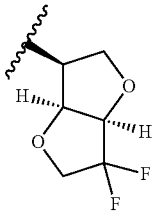 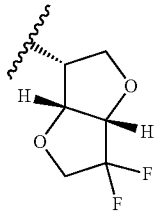
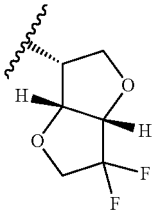 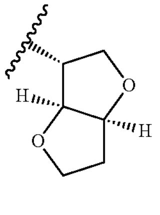 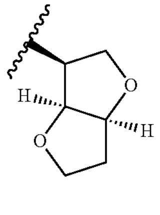
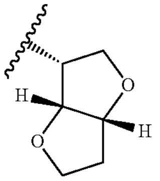 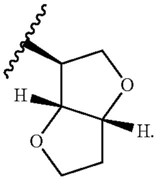
In some embodiments, $R^6$ is selected from: hydrogen, halogen, $C_1$-$C_3$ alkyl group, $C_1$-$C_3$ alkoxy group, —NH—CN,
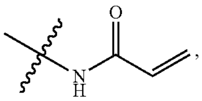 [SMILES: *NC(=O)C=C], 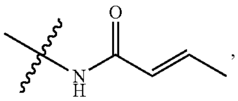,
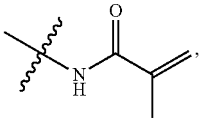,
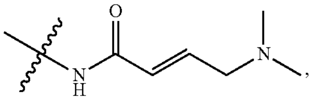,
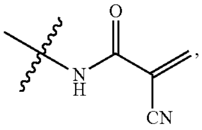, 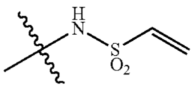.

In some embodiments, W, X are both CH; Y and Z are independently selected from N or $CR^6$ respectively, wherein, $R^6$ is selected from: hydrogen, halogen, $C_1$-$C_3$ alkyl, $C_1$-$C_3$ alkoxy, —NH—CN,

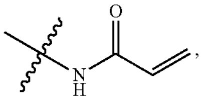,
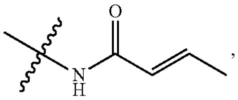,
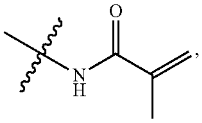,
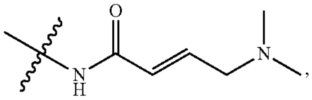,
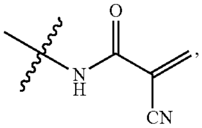,
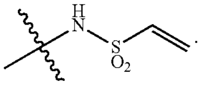.

In some embodiments, W, X are both CH; Y is $CR^6$, wherein, $R^6$ is selected from: hydrogen, halogen, $C_1$-$C_3$ alkyl, $C_1$-$C_3$ alkoxy,

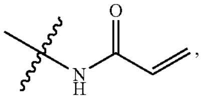,
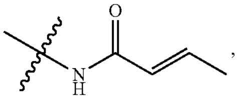,
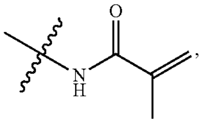,
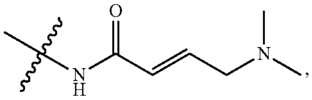, and Z is CH or N.

In some embodiments, W, X and Z are all CH; Y is $CR^6$, wherein $R^6$ is

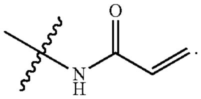.

In some embodiments, $R^2$ is selected from: H, halogen, $—(CH_2)_mNR^3R4$, $—(CH_2)_m—CR^3R^4R^5$; wherein, each m is independently 0, 1, 2, or 3;

each $R^3$ and each $R^4$ are independently selected from: H, one or more $R^{12}$ substituted $C_1$-$C_3$ alkyl groups, or $R^3$, $R^4$, together with the attached N or C to form a 5-11 membered single ring, fused ring, bridge ring, or spiral ring substituted by one or more $R^{12}$ with ring atoms containing 0, 1, 2, or 3 heteroatoms;

$R^5$ is selected from: H, cyano or $C_1$-$C_3$ alkyl;

each $R^{12}$ is independently selected from: H, hydroxyl, acetyl, $R^{13}$ substituted or unsubstituted 4-8-membered heterocyclic groups, halogens, hydroxyl, amino, $C_1$-$C_3$ alkyl, $C_1$-$C_3$ alkoxy, $—NHR^{13}$, $—N(R^{13})$ 2; $R^{13}$ is a $C_1$-$C_3$ alkyl group.

In some embodiments, $R^2$ is selected from: H, halogen, $—(CH_2)_mNR^3R^4$, $—(CH_2)_m—CR^3R^4R^5$; wherein, each m is independently 0 or 1;

each $R^3$ and each $R^4$ are independently selected from: H, one or more $R^{12}$ substituted $C_1$-$C_3$ alkyl groups, or $R^3$, $R^4$, together with the attached N or C to form a 5-11 membered single ring, fused ring, bridge ring, or spiral ring substituted by one or more $R^{12}$ with ring atoms containing 0, 1, 2, or 3 heteroatoms;

$R^5$ is selected from: H, cyano or $C_1$-$C_3$ alkyl;

each $R^{12}$ is independently selected from: H, hydroxyl, acetyl, $R^{13}$ substituted or unsubstituted 4-8-membered heterocyclic groups, halogens, hydroxyl, amino, $C_1$-$C_3$ alkyl, $C_1$-$C_3$ alkoxy, $—NHR^{13}$, $—N(R^{13})_2$; $R^{13}$ is a $C_1$-$C_3$ alkyl group.

In some embodiments, $R^2$ is selected from: H, halogen.

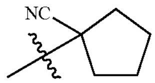,
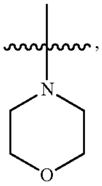,
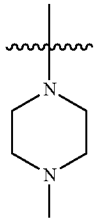,
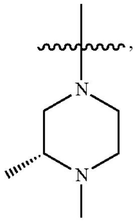,
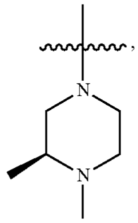,
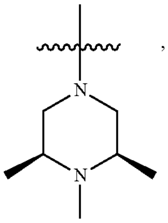,
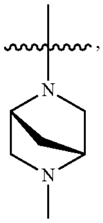,
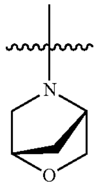,
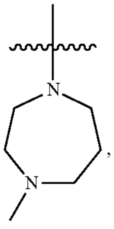,
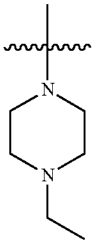,
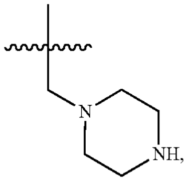,
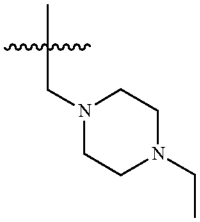,
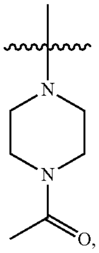,
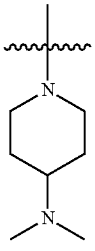,
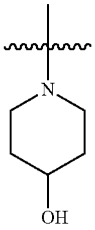,
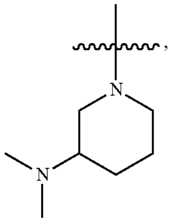,
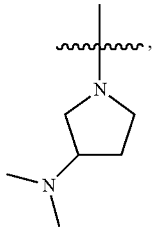, -continued

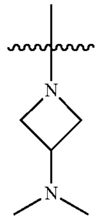, 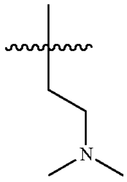, 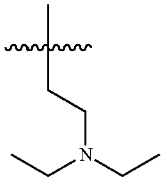,

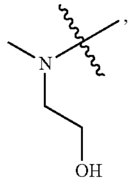,

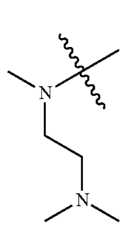, 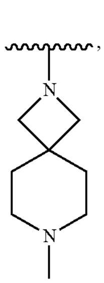, 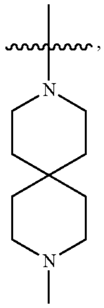, 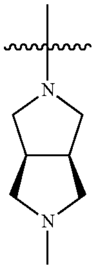,

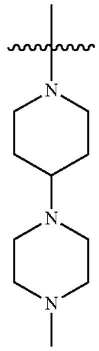, 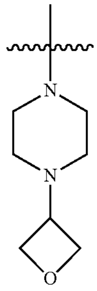, 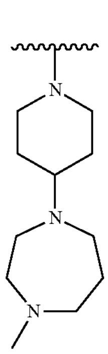,

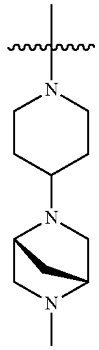, 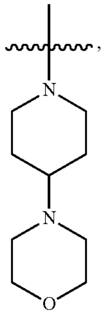, 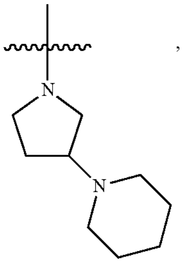,

-continued

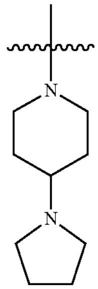, 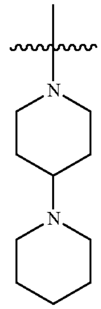.

In some embodiments, $R^1$ is selected from: H, halogen, cyano, formamide, $C_1$-$C_6$ alkyl group, $C_1$-$C_6$ alkoxy group, $C_3$-$C_6$ cycloalkyl group, $C_3$-$C_6$ cycloalkoxy group, halogenated $C_1$-$C_6$ alkyl group, halogenated $C_1$-$C_6$ alkoxy group.

In some embodiments, $R^1$ is selected from: H, halogen, $C_1$-$C_3$ alkyl, $C_1$-$C_3$ alkoxy.

In some embodiments, $R^1$ is selected from: H, halogen, methyl, cyano, formamide, trifluoromethyl, difluoromethyl, methoxy, cyclopropyl, trifluoromethoxy.

In some embodiments, the 2-aminopyrimidine compounds has the structure shown in Formula (II) as follows:

(II)

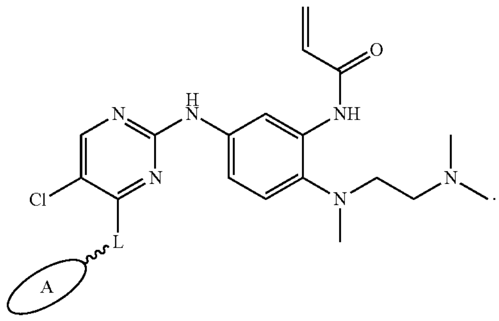.

The present disclosure also provides an application of JAK3 inhibitors of the 2-aminopyrimidine compounds or their pharmaceutically acceptable salts, isotope derivatives, solvates, or their stereoisomers, geometric isomers, tautomers, or prodrug molecules or metabolites.

The detailed technical solution is as follows:

An application of the 2-aminopyrimidine compounds or their pharmaceutically acceptable salts, isotope derivatives, solvates, or their stereoisomers, geometric isomers, tautomers, or prodrug molecules or metabolites in JAK3 inhibitors.

An application of the 2-aminopyrimidine compounds or their pharmaceutically acceptable salts, isotope derivatives, solvates, or their stereoisomers, geometric isomers, tautomers, or prodrug molecules or metabolites in the preparation of drugs for the prevention and/or treatment of tumors and/or inflammatory diseases.

In some embodiments, the tumors are hematomas and solid tumors, wherein the hematomas are multiple myeloma, B-lymphoma, myelofibrosis, polycythemia vera, primary thrombocytosis, chronic myeloid leukemia, acute myeloid leukemia, acute lymphocytic leukemia, chronic myeloid leukemia, histiocyte lymphoma, acute megakaryocyte leukemia Juvenile lymphoblastic leukemia, T-lymphoblastic leukemia, T-lymphoblastic lymphoma; the solid tumors are non small cell lung cancer, small cell lung cancer, lung adenocarcinoma, lung squamous cell cancer, pancreatic cancer, breast cancer, prostate cancer, liver cancer, skin cancer, epithelial cell cancer, gastrointestinal stromal tumor, nasopharyngeal carcinoma, glioma; the inflammatory diseases are rheumatoid arthritis, atopic dermatitis, contact dermatitis, psoriasis, psoriasis, ulcerative colitis, Crohn's disease, eczema, discoid lupus erythematosus, systemic lupus erythematosus, alopecia areata, graft-versus-host disease, ankylosing spondylitis, diffuse systemic sclerosis of skin, dermatomyositis.

The present disclosure also provides a pharmaceutical composition for preventing and treating tumors and/or inflammatory diseases.

The detailed technical solution is as follows:

A pharmaceutical composition for preventing and treating tumors and/or inflammatory diseases, is prepared from active ingredients and a pharmaceutically acceptable excipient and/or carrier, wherein the active ingredients comprise the 2-aminopyrimidine compound or pharmaceutically acceptable salt, isotope derivative, solvate, or stereoisomer, geometric isomer, tautomer, or prodrug molecule, metabolites.

The present disclosure also provides a class of structurally novel 2-aminopyrimidine compounds or their pharmaceutically acceptable salts, isotope derivatives, solvates, or their stereoisomers, geometric isomers, tautomers, or prodrug molecules or metabolites, which can efficiently and selectively inhibit the kinase activity of Janus Kinase 3 (JAK3), and has strong signal inhibition and cell proliferation inhibition effects on various blood tumor cells (especially human acute myeloid leukemia cells U937) and solid tumor cells, and can be used to prepare drugs for anti-tumor and JAK3 kinase related inflammatory disease treatment.

DESCRIPTION OF THE EMBODIMENTS

Figure 1:
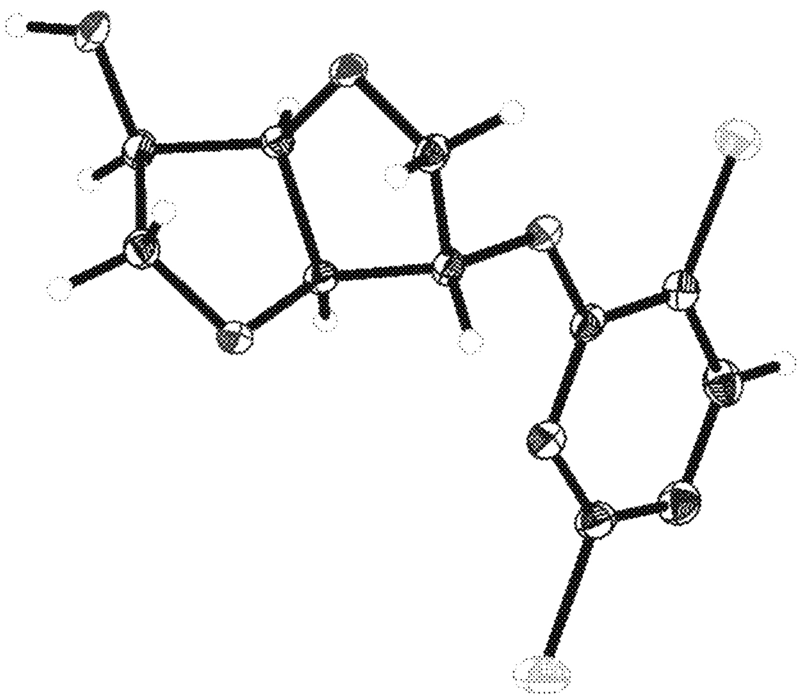
FIG. 1 shows the single crystal structure of intermediate 3-1.

In the compounds of the present disclosure, when any variable (eg. $R^3$, $R^4$, etc.) occurs more than once in any component, its definition at each occurrence is independent of the definition at each other occurrences. Similarly, combinations of substituents and variables are permissible if only the compound with such combinations are stabilized. A line from a substituent to a ring system indicates that the indicated bond may be attached to any substitutable ring atom. If the ring system is polycyclic, it means that such bonds are only attached to any suitable carbon atoms adjacent to the ring. It is understood that an ordinary skilled in the art can select substituents and substitution patterns for the compounds of the present disclosure to provide the compounds that are chemically stable and can be readily synthesized from the available starting materials by the methods described below. If a substituent itself is substituted by more than one group, it should be understood that these groups may be on the same carbon atom or on different carbon atoms, so long as the structure is stabilized.

The term "alkyl" in the present disclosure is meant to include branched and straight chain saturated aliphatic hydrocarbon groups having the specified number of carbon atoms. For example, the definition of "C1-C6" in "C1-C6 alkyl" includes groups having 1, 2, 3, 4, 5 or 6 carbon atoms arranged in a straight or branched chain. For example, "C1-C6 alkyl" specifically includes methyl, ethyl, n-propyl, isopropyl, n-butyl, tert-butyl, isobutyl, pentyl, hexyl. The term "cycloalkyl" refers to a monocyclic saturated aliphatic hydrocarbon group having the specified number of carbon atoms. For example, "cycloalkyl" includes cyclopropyl, cyclobutyl, cyclopentyl or cyclohexyl, etc. The term "alkoxy" refers to a group with an —O-alkyl structure, such as $-OCH_3$, $-OCH_2CH_3$, $-OCH_2CH_2CH_3$, $-O-CH_2CH(CH_3)_2$, $-OCH_2CH_2CH_2CH_3$, $-O-CH(CH_3)_2$, etc.

The term "heterocyclyl" is a saturated or partially unsaturated monocyclic or polycyclic cyclic substituent wherein one or more ring atoms are selected from N, O or $S(O)_m$ (wherein m is an integer from 0 to 2), and the remaining ring atoms are carbon, such as: morpholinyl, piperidinyl, tetrahydropyrrolyl, pyrrolidinyl, dihydroimidazolyl, dihydroisoxazolyl, dihydroisothiazolyl, dihydro oxadiazolyl, dihydrooxazolyl, dihydropyrazinyl, dihydropyrazolyl, dihydropyridyl, dihydropyrimidinyl, dihydropyrrolyl, dihydrotetrazolyl, dihydrothiadiazolyl, dihydrothiazolyl, dihydrothienyl, dihydrotriazolyl, dihydroazetidine, tetrahydrofuranyl, tetrahydrothienyl, etc., and their N-oxides. The connection of heterocyclic substituents can be achieved through carbon atoms or through heteroatoms.

As understood by the skilled in the art, "halogen" or "halo" as used herein means chlorine, fluorine, bromine and iodine.

Unless otherwise defined, alkyl, cycloalkyl, aryl, heteroaryl and heterocycloalkyl substituents can be unsubstituted or substituted. For example, a C1-C6 alkyl group can be substituted by one, two, or three substituents selected from OH, halogen, alkoxy, dialkylamino, or heterocyclyl groups such as morpholinyl, piperidinyl, etc.

The present disclosure provides a class of 2-aminopyrimidine compounds with the structure shown in Formula (I):

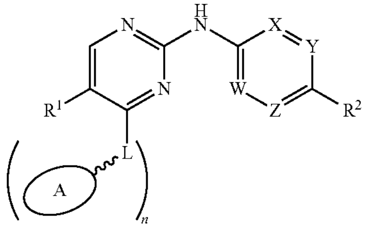

(I)

wherein, $R^1$ is selected from: H, halogen, cyano, one or more $R^{11}$ substituted or unsubstituted $C_1$-$C_6$ alkyl groups, one or more $R^{11}$ substituted or unsubstituted $C_3$-$C_6$ cycloalkyl groups, one or more $R^{11}$ substituted or unsubstituted C1-C6 alkoxy groups, one or more $R^{11}$ substituted or unsubstituted $C_3$-$C_6$ cycloalkoxy groups, formamide groups;

$R^2$ is selected from: H, halogen, —$(CH_2)_mNR^3R^4$, —$(CH_2)_mCR^3R^4R^5$ or —$(CH_2)_mOCR^3R^4R^5$; wherein, each m is independently 0, 1, 2, or 3; each $R^3$ and each $R^4$ are independently selected from: H, one or more $R^{12}$ substituted C1-C6 alkyl groups, or $R^3$, $R^4$, together with the attached N or C to form a 3-12 membered single ring, fused ring, bridge ring, or spiral ring substituted by one or more $R^{12}$ with ring atoms containing 0, 1, 2, or 3 heteroatoms; $R^5$ is selected from: H, cyano or $C_1$-$C_3$ alkyl; each $R^{12}$ is independently selected from: H, halogen, hydroxyl, amino, $C_1$-$C_3$ alkyl, $C_1$-$C_3$ alkyl substituted by —C(═O)$NHR^{13}$, hydroxy substituted $C_1$-$C_3$ alkyl, $C_1$-$C_3$ alkyl substituted by $C_3$-$C_6$ cycloalkyl group, $C_3$-$C_8$ heterocyclic group substituted $C_1$-$C_3$ alkyl group, $C_1$-$C_3$ alkoxy, —$NHR^{13}$, —$N(R^{13})_2$, —C(═O)$R^{13}$, $R^{13}$ substituted or unsubstituted 4-8-membered single ring, fused ring, bridge ring, or spiral ring containing 0, 1, 2, or 3 heteroatoms; $R^{13}$ is a $C_1$-$C_3$ alkyl group; the heteroatom is O, S, and/or N;

W, X, Y, and Z are independently N or —$CR^6$; wherein, $R^6$ is selected from: hydrogen, halogen, one or more $R^{11}$ substituted or unsubstituted $C_1$-$C_3$ alkyl groups, one or more $R^{11}$ substituted or unsubstituted $C_1$-$C_3$ alkoxy groups, —NH—CN, —NHC(O)—CR7=$CR^8R^9$, —$NHS(O)_2$—$CR^7$═$CR^8R^9$; $R^7$, $R^8$, and $R^9$ are independently selected from: H, cyano, one or more $R^{11}$ substituted or unsubstituted $C_1$-$C_6$ alkyl groups; wherein n is 0 or 1;

L is O or S;

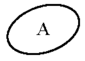

is a 4-12 membered saturated or partially saturated single ring, bridge ring, spiral ring, or fused ring substituted with one or more $R^{10}$ with ring atoms containing 0, 1, 2, or 3 heteroatoms; wherein, each $R^{10}$ is independently selected from: hydrogen, halogen, hydroxyl, one or more $R^{11}$ substituted or unsubstituted $C_1$-$C_3$ alkyl groups, one or more $R^{11}$ substituted or unsubstituted $C_1$-$C_3$ alkoxy groups, and the heteroatoms are O, S, and/or N;

$R^{11}$ is selected from: halogen, hydroxyl, amino, $C_1$-$C_3$ alkyl, $C_1$-$C_3$ alkoxy, —$NHR^{13}$, —$N(R^{13})_2$, —C(═O)$R^{13}$.

The present disclosure includes free forms of compounds of Formula I or Formula II, as well as pharmaceutically acceptable salts and stereoisomers thereof. Some specific exemplary compounds in the present disclosure are protonation salts of amine compounds. The term "free form" refers to the amine compound in non-salt form. "The pharmaceutically acceptable salts" include not only exemplary salts of the particular compounds described herein, but also typical pharmaceutically acceptable salts of free form of all compounds of Formula I and II. The free forms of specific salts of the compounds can be isolated using techniques known in the art. For example, the free form can be regenerated by treating the salt with an appropriate dilute aqueous base, such as dilute aqueous NaOH, dilute aqueous potassium carbonate, dilute aqueous ammonia, and dilute aqueous sodium bicarbonate. The free forms differ somewhat from their respective salt forms in certain physical properties such as solubility in polar solvents, but for the purposes of the invention, such salts of acid or base are otherwise pharmaceutically equivalent to their respective free forms.

The pharmaceutically acceptable salts of the present disclosure can be synthesized from the compounds containing a basic or acidic moiety in the present disclosure by conventional chemical methods. Generally, salts of basic compounds can be prepared by ion exchanged chromatography or by reacting the free base with a stoichiometric or excess amount of inorganic or organic acid in the desired salt form in a suitable solvent or combination of solvents. Similarly, salts of acidic compounds can be formed by reaction with a suitable inorganic or organic base.

Accordingly, the pharmaceutically acceptable salts of the compounds in the present disclosure include conventional non-toxic salts of the compounds in the present disclosure formed by reacting a basic compound of the present disclosure with an inorganic or organic acid. For example, conventional non-toxic salts include those derived from inorganic acids such as hydrochloric acid, hydrobromic acid, sulfuric acid, sulfamic acid, phosphoric acid, nitric acid, etc. They also include those derived from organic acids such as acetic acid, propionic acid, succinic acid, glycolic acid, hard Fatty acid, lactic acid, malic acid, tartaric acid, citric acid, ascorbic acid, pamoic acid, maleic acid, hydroxymaleic acid, phenylacetic acid, glutamic acid, benzoic acid, salicylic acid, p-aminobenzenesulfonic acid, 2-acetoxy-benzoic acid, fumaric acid, toluenesulfonic acid, methanesulfonic acid, ethanedisulfonic acid, oxalic acid, isethionic acid, and trifluoroacetic acid, etc.

If the compounds of the present disclosure are acidic, the appropriate "pharmaceutically acceptable salts" refer to the salts prepared from pharmaceutically acceptable non-toxic bases including inorganic bases and organic bases. The salts derived from inorganic bases include aluminum, ammonium, calcium, copper, iron, ferrous, lithium, magnesium, manganese, manganous, potassium, sodium, zinc, etc. Particularly preferably, ammonium salts, calcium salts, magnesium salts, potassium salts, and sodium salts. The salts derived from pharmaceutically acceptable organic non-toxic bases include salts of primary, secondary and tertiary amines. Substituted amines include naturally occurring substituted amines, cyclic amines and basic ion exchange resins such as Amino acid, betaine, caffeine, choline, N,N'-dibenzylethylenediamine, diethylamine, 2-diethylaminoethanol, 2-dimethylaminoethanol, aminoethanol, ethanolamine, ethyl Diamine, N-ethylmorpholine, N-ethylpiperidine, Glucosamine, Glucosamine, Histidine, Hydroxocobalamin, Isopropylamine, Lysine, Methylglucamine, Morpholine, Piperazine, Piperidine, quack, polyamine resin, procaine, purine, theobromine, triethylamine, trimethylamine, tripropylamine, tromethamine, etc.

The preparation of the pharmaceutically acceptable salts described above and other typical pharmaceutically acceptable salts was described in more detail by Berg et al., in "Pharmaceutical Salts," J. Pharm. Sci. 1977:66:1-19.

Since under physiological conditions, the deprotonated acidic moieties (such as carboxyl groups) in compounds can be anions, which carry electric charges and can be neutralized by internally cationic protonated or alkylated basic moieties (such as tetravalent nitrogen atoms), so it should be noted that the compounds of the present disclosure are potential inner salts or zwitterions.

In one embodiment, the present disclosure provides compounds with the structure of Formula (I) or Formula (II) and their pharmaceutically acceptable salts for treating human or other mammalian tumors or inflammatory diseases.

In one embodiment, the compounds of the present disclosure and their pharmaceutically acceptable salts can be used to treat or control of multiple myeloma, B-lymphoma, myelofibrosis, polycythemia vera, primary thrombocytosis, chronic myeloid leukemia, acute myeloid leukemia, acute lymphocytic leukemia, chronic myeloid leukemia, histiocyte lymphoma, acute megakaryocyte leukemia Juvenile lymphoblastic leukemia, T-lymphoblastic leukemia, T-lymphoblastic lymphoma, non-small cell lung cancer, small cell lung cancer, lung adenocarcinoma, lung squamous cell cancer, pancreatic cancer, breast cancer, prostate cancer, liver cancer, skin cancer, epithelial cell cancer, gastrointestinal stromal tumor, nasopharyngeal carcinoma, glioma; The inflammatory diseases are rheumatoid arthritis, atopic dermatitis, contact dermatitis, psoriasis, psoriasis, ulcerative colitis, Crohn's disease, eczema, discoid lupus erythematosus, systemic lupus erythematosus, alopecia areata, graft-versus-host disease, ankylosing spondylitis, diffuse systemic sclerosis of skin, dermatomyositis.

Drug Metabolites and Prodrugs:

The metabolites of the compounds of the present disclosure and their pharmaceutically acceptable salts, and prodrugs that can be converted into the structures of the compounds of the present disclosure or their pharmaceutically acceptable salts in vivo, also fall within the scope of protection defined by the claims of this application.

Pharmaceutical Composition

The present disclosure also provides a pharmaceutical composition, comprising active ingredients within a safe and effective dosage range, as well as pharmaceutically acceptable carriers or excipients.

The "active ingredient" mentioned in the present disclosure refers to the compounds of Formula I or Formula II described in the present disclosure or their pharmaceutically acceptable salts, isotope derivatives, solvates, or their stereoisomers, geometric isomers, tautomers, or prodrug molecules or metabolites.

The "active ingredient" and pharmaceutical composition of the present disclosure can be used as JAK protein kinase inhibitors, and can be used to prepare drugs for preventing and/or treating tumor and/or inflammatory diseases.

"Safe and effective dosage" refers to the amount of the active ingredients that are sufficient to significantly improve the condition without causing serious side effects. Typically, the pharmaceutical compositions contain 1-2000 mg of active ingredients/formulation, and more preferably, 10-200 mg of active ingredients/formulation. Preferably, the 'one dose' is one tablet.

"Pharmaceutically acceptable carrier or excipient" refers to one or more compatible solid or liquid fillers or gel substances, which are suitable for human use, and must have sufficient purity and sufficiently low toxicity.

"Compatibility" here refers to that each component in the composition can be mixed with the active ingredients of the present disclosure intermingled between each other without significantly reducing the efficacy of the active ingredients.

Examples of pharmaceutically acceptable carriers or excipients include cellulose and its derivatives (such as sodium carboxymethyl cellulose, sodium ethylcellulose, cellulose acetate, etc.), gelatin, talc, solid lubricants (such as stearic acid, magnesium stearate), calcium sulfate, vegetable oil (such as soybean oil, sesame oil, peanut oil, olive oil, etc.), polyols (such as propylene glycol, glycerin, mannitol, sorbitol, etc.), emulsifier (such as Tween @), wetting agent (such as sodium dodecyl sulfate), colorant, flavoring agent, stabilizer, antioxidant, preservative, pyrogen-free water, etc.

In another preferred example, the compounds of Formula I or Formula II of the present disclosure can form complexes with macromolecular compounds or macromolecule through nonbonding cooperation. In another preferred example, the compound of Formula I or Formula II of the present disclosure, as a small molecule, can also be connected with a macromolecular compound or a polymer through a chemical bond. The macromolecular compounds can be biological macromolecules such as polysaccharides, proteins, nucleic acids, peptides, etc.

There is no special restriction on application methods of the active ingredients or drug composition of the present disclosure, and typical administration methods include (but not limited to) oral, intratumoral, rectal, parenteral (intravenous, intramuscular or subcutaneous), etc.

The solid dosage forms used for oral administration include capsules, tablets, pills, powders and granules.

In these solid dosage forms, the active ingredient is mixed with at least one conventional inert excipient (or carrier), such as sodium citrate or dicalcium phosphate, or with the following ingredients:

(a) fillers or compatibilizers, such as starch, lactose, sucrose, glucose, mannitol, and silicic acid;
(b) adhesives, such as hydroxymethyl cellulose, alginate, gelatin, polyvinylpyrrolidone, sucrose, and arabic gum;
(c) humectants, such as glycerin;
(d) disintegrating agents, such as agar, calcium carbonate, potato starch or cassava starch, algic acid, some composite silicates, and sodium carbonate;
(e) slow solvent, such as paraffin;
(f) absorption accelerators, such as quaternary amine compounds;
(g) wetting agents, such as cetyl alcohol and glyceryl monostearate;
(h) adsorbents, such as kaolin; and
(i) lubricants, such as talc, calcium stearate, magnesium stearate, solid polyethylene glycol, sodium dodecyl sulfate, or their mixtures. In the case of capsules, tablets and pills, the dosage form may also include buffers.

The solid dosage form can also be prepared with coating and shell materials, such as casings and other materials known in the art. They may comprise an opaque agent. Furthermore, the active ingredients from such compositions may be released in certain part of the digestive tract in a delayed manner. Examples of embedding components that can be used are polymers and waxes.

Liquid dosage forms for oral administration include pharmaceutically acceptable lotion, solutions, suspensions, syrups or tinctures. In addition to the active ingredients, the liquid dosage form may include inert diluents commonly used in the art, such as water or other solvents, solubilizers, emulsifiers (such as ethanol, isopropanol, ethyl carbonate, ethyl acetate, propylene glycol, 1,3-butanediol, dimethylformamide), and oil (especially cottonseed oil, peanut oil, corn germ oil, olive oil, castor oil and sesame oil or mixtures of these substances). In addition to these inert diluents, the composition may also include auxiliary agents, such as wetting agents, emulsifiers and suspending agents, sweeteners, flavoring agents and spices.

In addition to the active ingredients, the suspension may contain suspension agents, such as ethoxylated isooctadecanol, polyoxyethylene sorbitol and dehydrated sorbitol ester, microcrystalline cellulose, aluminum methoxide and agar, or mixtures of these substances.

Compositions for parenteral injection may include physiologically acceptable sterile aqueous or anhydrous solutions, dispersions, suspensions or emulsions, and sterile powders for re-dissolution into sterile injectable solutions or dispersions. Suitable aqueous and non-aqueous carriers, diluents, solvents or excipients include water, ethanol, polyols, and their suitable mixtures.

The compound of the present disclosure can be administered separately or in combination with other therapeutic drugs (such as hypoglycemic drugs).

When using a pharmaceutical composition, a safe and effective amount of the compound of the present disclosure is applied to mammals (such as humans) in need of treatment, wherein the dosage at the time of application is a pharmaceutically effective dosage. For an individual weighing 60 kg, the daily dosage is usually 1-2000 mg, preferably 20-500 mg. Of course, the specific dosage should also consider factors such as the route of administration and the patient's health status, etc., which are within the skill range of a skilled physician.

Drug Combinations

The compounds of Formula I or Formula II may be used in combination with other drugs known to treat or improve similar conditions. In the case of combined administration, the administration mode and dosage of the original drug remain unchanged, while the compounds of Formula I or Formula II are administered simultaneously or subsequently. When the compounds of Formula I or Formula II are administered concomitantly with one or more other drugs, it is preferred to use a pharmaceutical composition containing one or more known drugs and the compounds of Formula I or Formula II. Drug combination also includes administration of the compounds of Formula I or Formula II with one or more other known drugs in overlapping time periods. When the compounds of Formula I or Formula II are used in combination with one or more other drugs, the compounds of Formula I or Formula II or known drugs may be administered at lower doses than that when they are administered alone.

Drugs or active ingredients that can be used in combination with the compounds of Formula I or Formula II include, but not limited to: estrogen receptor modulators, androgen receptor modulators, retinal-like receptor modulators, cytotoxic/cytostatics, antiproliferative agents, protein transferase inhibitors, HMG-CoA reductase inhibitors, HIV protein kinase inhibitors agents, reverse transcriptase inhibitors, angiogenesis inhibitors, cell proliferation and survival signaling inhibitors, drugs that interfere with cell cycle checkpoints and apoptosis inducers, cytotoxic drugs, tyrosine protein inhibitors, EGFR inhibitors, VEGFR inhibitors, serine/threonine protein inhibitors, Bcr-Abl inhibitors, c-Kit inhibitors, Met inhibitors, Raf inhibitors, MEK inhibitors, MMP inhibitors, topoisomerase inhibitors, histidine Acid deacetylase inhibitors, proteasome inhibitors, CDK inhibitors, Bcl-2 family protein inhibitors, MDM2 family protein inhibitors, IAP family protein inhibitors, STAT family protein inhibitors, PI3K inhibitors, AKT inhibitors, integrin blocker, interferon-α, interleukin-12, COX-2 inhibitor, p53, p53 activator, VEGF antibody, EGF antibody, JAK inhibitors, etc.

In one example, the drugs or active ingredients that can be used in combination with the compounds of Formula (I) or Formula (II) include, but are not limited to: Aldesleukin, Alendronic Acid, Interferon, Altranoin, Allopurinol, Sodium Allopurinol, Palonosetron Hydrochloride, Hexamelamine, Aminoglumitide, Amifostine, Ammonium rubicin, ampicillin, anastrozole, dolasetron, aranesp, arglabin, arsenic trioxide, anoxin, 5-azacytidine, azathioprine, bacille Calmette-Guerin or tic BCG, betadine, beta-acetate Metasone, betamethasone sodium phosphate preparation, bexarotene, bleomycin sulfate, bromouridine, bortezomib, busulfan, calcitonin, alezolizumab injection, capecitabine, carboplatin, kangshi cefesone, cymoleukin, daunorubicin, chlorambucil, cisplatin, cladribine, cladribine, clodronate, cyclophosphamide, cytarabine, dacarbazine, actinobacteria D, Daunorubicin Liposome, Dexamethasone, Dexamethasone Phosphate, Estradiol Valerate, Denisole 2, Dipomet, Delorelin, Delazoxan, Diethylstilbestrol, Dafucon, Docetaxel, Deoxyfluridine, Doxorubicin, Dronabinol, Chin-166-chitosan complex, eligard, rasburicase, epirubicin hydrochloride, aprepitant, epirubicin, epoetin alfa, erythropoietin, eplatin, Levamisole tablets, estradiol preparations, 17-beta-estradiol, estramustine sodium phosphate, ethinyl estradiol, amifostine, hydroxyphosphate, fenbifu, etoposide, fadrozole, tamoxib fenestrate, filgrastim, finasteride, filgrastim, floxuridine, fluconazole, fludarabine, 5-fluorodeoxyuridine monophosphate, 5-fluorouracil, fluoxymesterone, Flutamide, Formestan, 1-β-D-D-arabinofuranocytothidine-5'-stearoyl phosphate, Formustine, Fulvestrant, Gammaglobulin, Gemcitabine, Gemtox Monoclonal antibody, imatinib mesylate, carbazide, wax paper capsules, goserelin, granisilone hydrochloride, histrelin, and methoxine, hydrocortisone, erythro-hydroxynonyl adrenal gland Purine, hydroxyurea, titan isibemumab, idarubicin, ifosfamide, interferon alpha, interferon-alpha2, interferon alpha-2A, interferon alpha-2B, interferon alpha-nl, Interferon alpha-n3, interferon beta, interferon gamma-la, interleukin-2, intron A, Iressa, irinotecan, keteri, lentinan sulfate, letrozole, tetrahydroform Folic acid, leuprolide, leuprolide acetate, levothyroxine, levothyroxine calcium salt, levothyroxine sodium, levothyroxine sodium preparations, lomustine, lonidamine, dronabinol, Nitrogen mustard, mecobalamin, medroxyprogesterone acetate, megestrol acetate, melphalan, esterified estrogen, 6-mercaptopurine, mesna, methotrexate, methyl aminolevulinate, mitifoxine, minocycline, mitomycin C, mitotane, mitosodium quinone, trolosteine, doxorubicin citrate liposome, nedaplatin, pegylated filgras kiosk, opryleukin, neupogen, nilutamide, tamoxifen, NSC-631570, Recombinant Human Interleukin 1-β, Octreotide, Ondansetron Hydrochloride, Dehydrocortisone Oral Solution, Oxaliplatin, Paclitaxel, Prednisone Sodium Phosphate, Pegaspargase, Pegasin, Pentostatin, Streptolyticum, Pilocarpine Hydrochloride, Pirarubicin, Pukamycin, Porfimer Sodium, Prednimustine, Steprednisolone, Prednisone, Premax Li, Procarb, Recombinant Human Erythropoietin, Raltitrexed, Ribi, Etidronate, Rhenium-186, Rituxan, Strength-A, Romotide, Pilocarpine Hydrochloride Tablets, Octreotide, Samostim, Semustine, Sizoran, Sobuzoxan, Methylprednisolone, Paphos Acid, Stem Cell Therapy, Streptozocin, Strontium Chloride-89, Levothyroxine Sodium, Tamoxifen, Tansu Loxin, Tasonamin, Tastolactone, Taxotere, Tecethiazine, Temozolomide, Teniposide, Testosterone Propionate, Methyltestosterone, Thioguanine, Thiatepa, Thyroid Stimulating Hormone, Tiludronic Acid, Topotecan, Toremifene, Tosilimumab, Trastuzumab, Triosulfan, Tretinoin, Methotrexate Tablets, Trimethylmelamine, Trimethrexate, Tripro acetate Relin, triptorelin pamoate, eufradine, uridine, valrubicin, veslinone, vinblastine, vincristine, vincristine, vinorelbine, velulizine, dextran Propionimine, net statin, zofenin, paclitaxel protein stabilizer, acolbifene, interferon r-lb, affinitak, aminopterin, azoxifene, asoprisnil, atamestane, atrasentan, BAY 43-9006, Avastin, CCI-779, CDC-501, Celebrex, Cetuximab, Crinator, Cyproterone Acetate, Decitabine, DN-101, Doxorubicin-MTC, dSLIM, dutasteride, edotecarin, eflunomine, ixitecan, fenretinide, histamine dihydrochloride, histidine hydrogel implant, holmium-166 DOTMP, ibandronic acid, interferon gamma, intron-PEG, ixabepilone, keyhole limpet hemocyanin, L-651582, lanreotide, Lasoxifene, libra, lonafamib, imiprexifene, minoxifene, MS-209, liposomal MTP-PE, MX-6, nafarelin, nemorubicin, novarestat, nolatrexide, olimerson, onco-TCS, osidem, paclitaxel polyglutamate, sodium paclitaxel, PN-401, QS-21, quasiyang, R-1549, raloxifene, leopard Ranazyme, 13-cis-retinoic acid, satraplatin, siocalcidol, T-138067, tarceva, docosahexaenoate paclitaxel, thymosin alphal, gazofurin, tipifarnib, tirapazamine, TLK-286, toremifene, trans MID-lo7R, valspoda, vapretide, vatalanib, verteporfin, vinflunine, Z-100 and zolelinic acid or their combination.

The benefits of the present disclosure are:

(1) A novel structure of 2-aminopyrimidine compounds is provided.

(2) This type of compounds has a strong selective inhibitory effect on JAK3 kinase, can effectively inhibit the growth of various tumor cells, and can be used to prepare antitumor drugs.

(3) The compounds can effectively prevent the transmission of the JAK3-STAT5 signaling pathway, and can be used for the preparation of drugs for anti-inflammatory diseases.

A further description about the present disclosure is given below in conjunction with specific embodiments. It should be understood that these embodiments are only used to illustrate the present invention, but not to limit its scope. The following embodiments, which has not specified specific conditions, are usually performed in accordance with conventional conditions, such as those described in "Molecular Cloning: Laboratory Manual" (New York: Cold Spring Harbor Laboratory Press, 1989) edited by Sambrook, etc, or as recommended by the manufacturer. Unless otherwise specified, percentages and portions are calculated by weight.

Unless otherwise defined, all professional and scientific terms used herein have the same meanings as those are familiar to the skilled in the art. In addition, any methods and materials similar or equivalent to those described herein can be applied to the methods of the present disclosure. The preferred implementation methods and materials described herein are for demonstration purposes only.

All the reagents used in the following examples are commercially available products.

Example 1

Synthesis of (3R,3aR,6S, 6aR)-6-(5-chloro-2-((3-chloro-4-(4-(4-methylpiperazin-1-yl) piperidin-1-yl) phenyl)amino)pyrimidin-4-yl) oxygen) hexahydrofurano[3,2-b]furan-3-ol (LS 3-96) and (3S,3aR,6R, 6aR)-6-(5-chloro-2-((3-chloro-4-(4-(4-methylpiperazin-1-yl) piperidin-1-yl)phenyl)amino)pyrimidin-4-yl) oxygen) hexahydrofurano[3,2-b]furan-3-ol (LS 4-97)

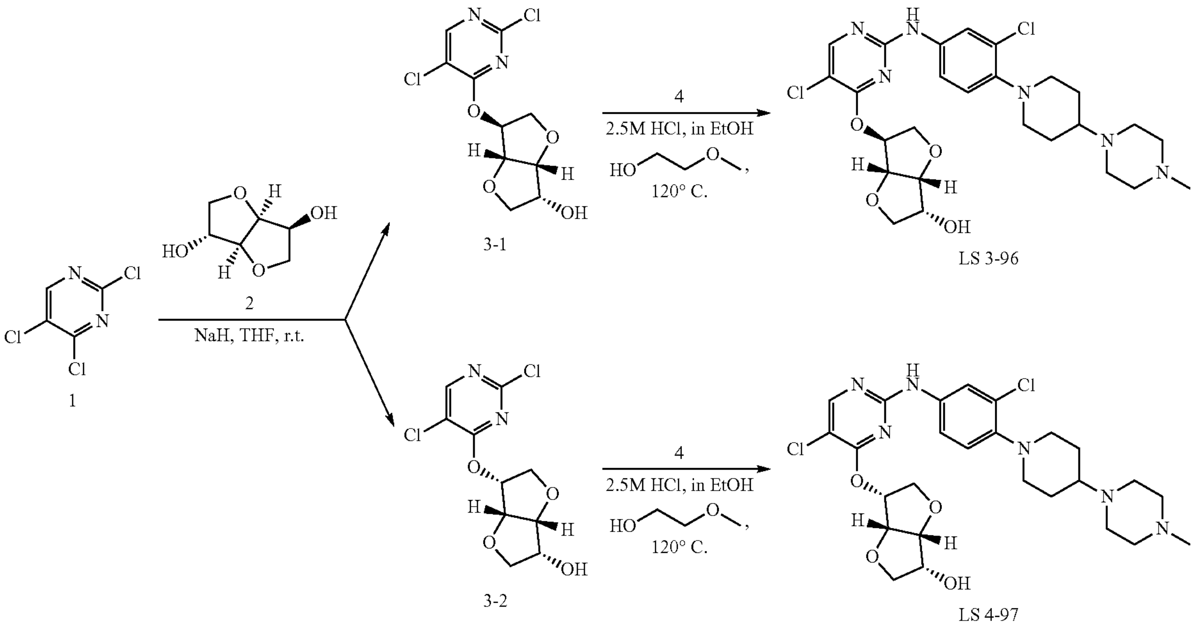

1 2 3-1 3-2 LS 3-96 LS 4-97

-continued

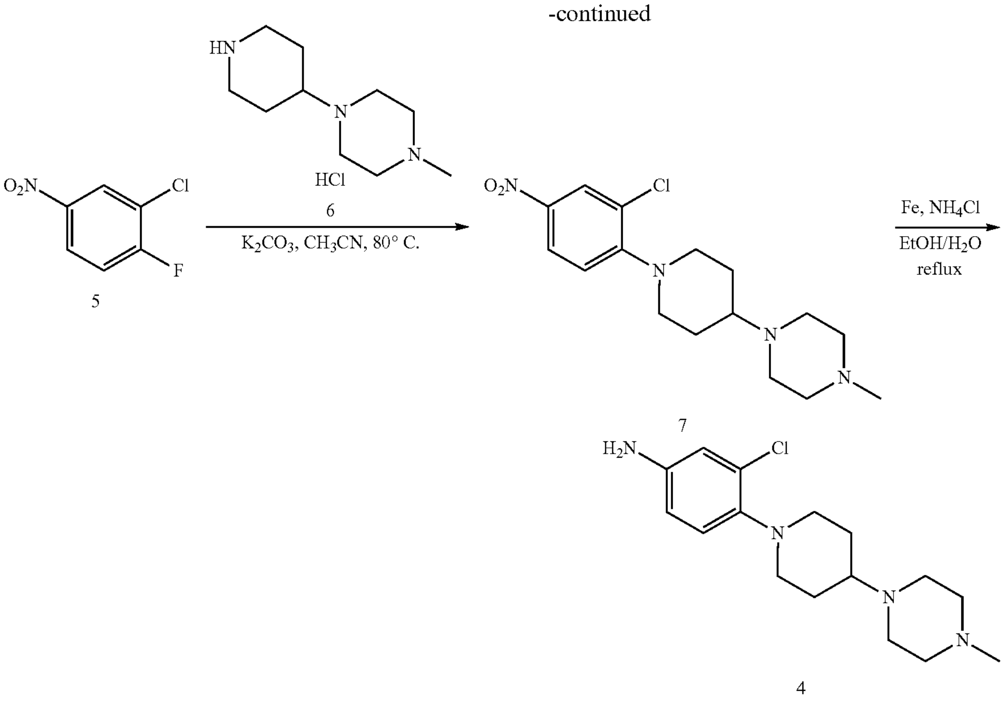

Step 1 Synthesis of 6-(2,5-dichloro-4-yl) oxygen) hexahydrofurano[3,2-b]furan-3-ol (3-1 and 3-2)

60% sodium hydride (0.13 g, 3.27 mmol) was added in portion to a tetrahydrofuran (THF, 20 mL) solution of isosorbitol (2, 0.48 g, 3.27 mmol) in an ice bath. After stirring for 10 minutes, 2,4,5-trichloropyrimidine (1, 0.5 g, 2.72 mmol) was added dropwise and stirred overnight at room temperature. After quenching with ice water carefully, the resulting mixture was extracted with dichloromethane twice. The organic layer was washed with brine, dried over anhydrous $Na_2SO_4$, and then concentrated under reduced pressure. The residue was then purified by silica gel column chromatography to obtain white solid 3-1 (227 mg, yield: 28.5%) and 3-2 (123 mg, yield: 15.5%)

$^1$H NMR for 3-1 (400 MHz, DMSO-$d_6$) δ 8.69 (s, 1H), 5.44-5.40 (m, 1H), 5.00 (d, J=6.0 Hz, 1H), 4.60 (d, J=4.4 Hz, 1H), 4.49 (t, J=4.8 Hz, 1H), 4.20-4.11 (m, 1H), 4.08-4.00 (m, 2H), 3.78 (dd, J=8.8, 6.4 Hz, 1H), 3.45-3.38 (m, 1H). MS (ESI) m/z 293.0 $[M+H]^+$.

The crystal structure and analysis of intermediate 3-1 are shown in FIG. 1 (CCDC number 2119312) and Table 1, confirming its chemical structure (stereo configuration) is correct.

TABLE 1

Single crystal parameters of intermediate 3-1

| | No. 3-1 |
|---|---|
| Molecular formula | $C_{10}H_{10}Cl_2N_2O_4$ |
| Molecular weight | 293.10 |
| Temperature/K | 100.00 (10) |
| Crystal system | Orthorhombic system |
| Space group | $P2_12_12_1$ |
| a/Å | 6.29734 (15) |
| b/Å | 10.7626 (2) |

TABLE 1-continued

Single crystal parameters of intermediate 3-1

| | No. 3-1 |
|---|---|
| c/Å | 17.8771 (4) |
| α/° | 90 |
| β/° | 90 |
| γ/° | 90 |
| Cell volume/Å$^3$ | 1211.63 (5) |
| Z | 4 |
| $\rho_{calc}$ g/cm$^3$ | 1.607 |
| μ/mm$^{-1}$ | 4.935 |
| F(000) | 600.0 |
| Crystal size/mm$^3$ | 0.14 × 0.13 × 0.12 |
| Illuminant | CuKα (λ = 1.54184) |
| 2θ Data collection scope/° | 9.592 to 147.426 |
| Index range | $-7 \le h \le 5$, $-13 \le k \le 11$, $-21 \le l \le 22$ |
| Diffraction collection | 7133 |
| Independent diffraction | 2385 [$R_{int}$ = 0.0396, $R_{sigma}$ = 0.0312] |
| Data/Restrictions/Parameters | 2385/0/164 |
| Goodness of fit F$^2$ | 1.055 |
| Final R index[I >= 2σ (I)] | $R_1$ = 0.0373, $wR_2$ = 0.0981 |
| Final R index[full data] | $R_1$ = 0.0374, $wR_2$ = 0.0983 |
| Maximum residual electron density peak/e Å$^{-3}$ | 0.31/−0.34 |
| Flack parameter | −0.005 (10) |

$^1$H NMR for 3-2 (400 MHz, $CDCl_3$) δ 8.34 (s, 1H), 5.59 (td, J=5.6, 3.6 Hz, 1H), 5.05 (t, J=5.2 Hz, 1H), 4.44 (d, J=4.8 Hz, 1H), 4.36 (s, 1H), 4.08 (dd, J=10.8, 3.6 Hz, 1H), 4.00-3.88 (m, 2H), 3.84 (d, J=10.0 Hz, 1H), 2.31 (d, J=4.4 Hz, 1H). MS (ESI) m/z 293.0 $[M+H]^+$.

Step 2 Synthesis of 3-chloro-4-(4-(4-methylpiperazin-1-yl) piperidin-1-yl) aniline (4)

1-Methyl-4-(piperidyl-4-yl) piperazine hydrochloride (6, 0.45 g, 2.0 mmol) was added to a solution of 2-chloro-1-fluoro-4-nitrobenzene (5, 0.3 g, 1.71 mmol) and potassium carbonate (0.48 g, 3.42 mmol) in acetonitrile (10 mL). The temperature of the system was raised to 80° C. to react overnight. After the reaction is complete, cooled to room temperature, spin-dried most of the solvent, extracted three times with dichloromethane. The organic phases were combined, washed with saturated salt water, dried over anhydrous sodium sulfate, and then concentrated under reduced pressure. The residue was then purified by silica gel column chromatography to obtain a yellow solid 7 (0.53 g, yield 92%).

$^1$H NMR (400 MHz, DMSO-$d_6$) δ 8.21 (d, J=2.8 Hz, 1H), 8.13 (dd, J=9.2, 2.8 Hz, 1H), 7.27 (d, J=9.2 Hz, 1H), 3.57 (d, J=12.0 Hz, 2H), 2.82 (t, J=11.6 Hz, 2H), 2.51-2.40 (m, 4H), 2.44-2.19 (m, 5H), 2.14 (s, 3H), 1.88 (d, J=11.6 Hz, 2H), 1.64-1.49 (m, 2H).

Reduced iron powder (1.42 g, 25.3 mmol) and ammonium chloride (4.6 g, 84.3 mmol) were added to a mixture of ethanol/water (2:1 by volume) of intermediate 7 (2.85 g, 8.43 mmol), refluxed and reacted for 2 hours. After the reaction was complete, cooled to room temperature, filtered over a pad of Celite e followed by MeOH wash, spin-dried most of the solvent, extracted three times with dichloromethane. The organic phases were combined, washed with saturated salt water, dried over anhydrous sodium sulfate, and then concentrated under reduced pressure. The residue was then purified by silica gel column chromatography to obtain solid 4 (2.2 g, yield 87%).

$^1$H NMR (400 MHz, $CDCl_3$) δ 6.87 (d, J=8.4 Hz, 1H), 6.74 (d, J=2.8 Hz, 1H), 6.53 (dd, J=8.4, 2.8 Hz, 1H), 3.51 (s, 2H), 3.29 (d, J=11.6 Hz, 2H), 2.89-2.22 (m, 14H), 1.89 (d, J=11.6 Hz, 2H), 1.80-1.73 (m, 2H). MS (ESI) m/z 309.2 $[M+H]^+$.

Step 3 Synthesis of (3R,3aR,6S, 6aR)-6-(5-chloro-2-((3-chloro-4-(4-(4-methylpiperazin-1-yl) piperidin-1-yl)phenyl)amino)pyrimidin-4-yl) oxygen) hexahydrofurano-[3,2b]furan-3-ol (LS 3-96)

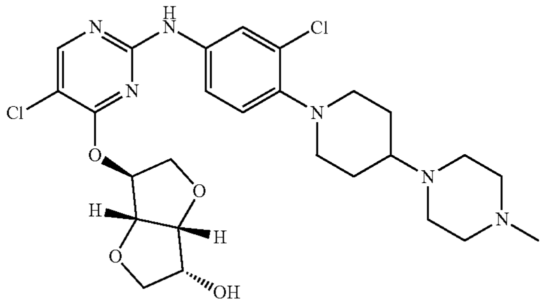 [SMILES: CN1CCN(C2CCN(c3ccc(Nc4ncc(Cl)c(O[C@H]5CO[C@H]6[C@@H]5OC[C@H]6O)n4)cc3Cl)CC2)CC1]

Intermediate 4 (60 mg, 0.195 mmol) and 2.5 M hydrogen chloride ethanol solution (0.2 mL) were added to the ethylene glycol monomethyl ether solvent of intermediate 3-1 (63 mg, 0.214 mmol), and the system was heated to 120° C. for overnight reaction. After the reaction was complete, the mixture was cooled to room temperature, concentrated under reduced pressure and extracted three times with dichloromethane. The organic phases were combined, washed with saturated salt water, dried over anhydrous sodium sulfate, and then concentrated under reduced pressure. The residue was then purified by silica gel column chromatography to obtain white solid LS 3-96 (33 mg, yield 30%). $^1$H NMR (400 MHz, $CDCl_3$) δ 8.15 (s, 1H), 7.65 (d, J=2.4 Hz, 1H), 7.29 (dd, J=8.8, 2.4 Hz, 1H), 7.08 (s, 1H), 6.99 (d, J=8.8 Hz, 1H), 5.51 (d, J=3.6 Hz, 1H), 4.76 (t, J=4.8 Hz, 1H), 4.69 (d, J=4.4 Hz, 1H), 4.35 (q, J=6.0 Hz, 1H), 4.25 (d, J=10.8 Hz, 1H), 4.18 (dd, J=10.8, 4.0 Hz, 1H), 3.94 (dd, J=9.2, 6.0 Hz, 1H), 3.66 (dd, J=9.2, 5.6 Hz, 1H), 3.46-3.34 (m, 2H), 2.82-2.33 (m, 11H), 2.30 (s, 3H), 1.93 (d, J=11.9 Hz, 2H), 1.83-1.68 (m, 2H). $^{13}$C NMR (151 MHz, $CDCl_3$) δ 163.32 (s), 157.32 (s), 156.96 (s), 145.19 (s), 134.40 (s), 129.12 (s), 121.75 (s), 120.53 (s), 118.60 (s), 107.03 (s), 85.70 (s), 82.13 (s), 81.22 (s), 73.60 (s), 73.46 (s), 72.32 (s), 61.72 (s), 55.45 (s), 51.70 (d, J=3.6 Hz), 49.03 (s), 46.06 (s), 28.58 (s). HRMS (ESI) calcd for $C_{26}H_{35}Cl_2N_6O_4$ $[M+H]^+$ 565.2091; found 565.2080.

Synthesis of (3S,3aR,6R, 6aR)-6-(5-chloro-2-((3-chloro-4-(4-(4-methylpiperazin-1-yl) piperidin-1-yl) phenyl)amino)pyrimidin-4-yl) oxygen) hexahydrofurano[3,2-b]furan-3-ol (LS 4-97)

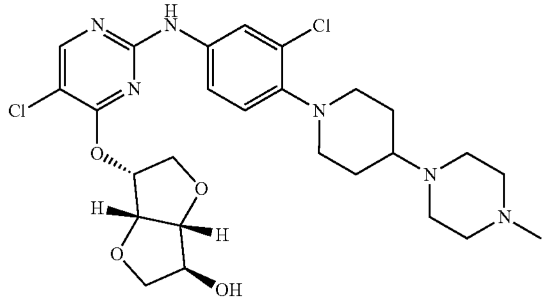 [SMILES: CN1CCN(C2CCN(c3ccc(Nc4ncc(Cl)c(O[C@@H]5CO[C@H]6[C@@H]5OC[C@@H]6O)n4)cc3Cl)CC2)CC1]

The synthesis method was the same as that of LS 3-96, except that the intermediate 3-2 was used instead of intermediate 3-1 in the reaction, with a yield of 37%. $^1$H NMR (400 MHz, $CDCl_3$) δ 8.14 (s, 1H), 7.78 (d, J=2.4 Hz, 1H), 7.16 (dd, J=8.8, 2.4 Hz, 1H), 7.02-6.96 (m, 1H), 6.88 (s, 1H), 5.51-5.44 (m, 1H), 5.06 (t, J=5.2 Hz, 1H), 4.47 (d, J=4.8 Hz, 1H), 4.39 (d, J=2.8 Hz, 1H), 4.08 (dd, J=10.4, 4.0 Hz, 1H), 4.03-3.94 (m, 2H), 3.88 (d, J=10.4 Hz, 1H), 3.40 (d, J=12.0 Hz, 2H), 3.01-2.18 (m, 14H), 2.05-1.97 (m, 1H), 1.93 (d, J=12.4 Hz, 2H), 1.84-1.71 (m, 2H). $^{13}$C NMR (151 MHz, $CDCl_3$) δ 163.93 (s), 157.35 (s), 156.53 (s), 144.91 (s), 134.60 (s), 128.81 (s), 121.82 (s), 120.33 (s), 118.58 (s), 106.42 (s), 88.72 (s), 80.62 (s), 76.64 (s), 75.87 (s), 75.67 (s), 71.10 (s), 61.69 (s), 55.37 (s), 51.67 (d, J=10.6 Hz), 48.94 (s), 46.01 (s), 31.63 (s). HRMS (ESI) calcd for $C_{26}H_{35}Cl_2N_6O_4$ $[M+H]^+$ 565.2091; found 565.2084.

Example 2

Synthesis of (3R,3aR,6R, 6aR)-6-(5-chloro-2-((3-chloro-4-(4-(4-methylpiperazin-1-yl) piperidin-1-yl) phenyl)amino)pyrimidin-4-yl) oxygen) hexahydrofurano[3,2-b]furan-3-ol (LS 4-104)

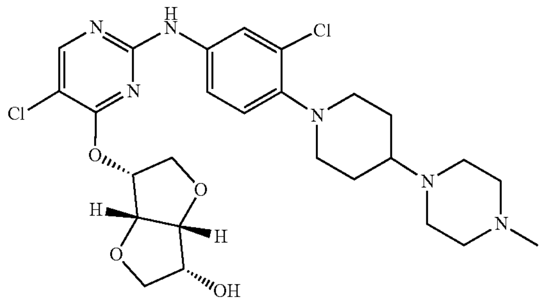 [SMILES: CN1CCN(C2CCN(c3ccc(Nc4ncc(Cl)c(O[C@@H]5CO[C@H]6[C@@H]5OC[C@H]6O)n4)cc3Cl)CC2)CC1]

The synthesis method was the same as that of LS 3-96 in Example 1, except that 1,4:3,6-bis dehydrated mannitol was used instead of isosorbitol (2) in the reaction.

$^1$H NMR (400 MHz, $CDCl_3$) δ 8.14 (s, 1H), 7.79 (d, J=2.4 Hz, 1H), 7.13 (dd, J=8.8, 2.4 Hz, 1H), 7.06-6.89 (m, 2H), 5.49 (q, J=5.2 Hz, 1H), 4.94 (t, J=5.2 Hz, 1H), 4.54 (t, J=5.2 Hz, 1H), 4.30 (dd, J=13.2, 6.4 Hz, 1H), 4.24-4.09 (m, 2H), 3.98 (dd, J=9.2, 6.4 Hz, 1H), 3.63 (dd, J=8.8, 8.0 Hz, 1H), 3.39 (d, J=11.6 Hz, 2H), 2.96-2.26 (m, 14H), 1.93 (d, J=12.0 Hz, 2H), 1.85-1.74 (m, 2H). $^{13}$C NMR (151 MHz, $CDCl_3$) δ 163.78 (s), 157.46 (s), 156.82 (s), 145.17 (s), 134.53 (s), 128.94 (s), 122.08 (s), 120.45 (s), 118.82 (s), 106.65 (s), 81.63 (s), 80.73 (s), 76.68 (s), 73.45 (s), 72.22 (s), 71.53 (s), 61.69 (s), 55.44 (s), 51.72 (d, J=1.0 Hz), 49.04 (s), 46.06 (s), 28.61 (s). HRMS (ESI) calcd for $C_{26}H_{35}Cl_2N_6O_4$ $[M+H]^+$ 565.2091; found 565.2087.

Example 3

Synthesis of (3R,3aR,6S, 6aR)-6-(5-Chloro-2-((2-methoxy-4-(4-(4-methylpiperazin-1-yl) piperidin-1-yl)phenyl)amino)pyrimidin-4-yl) oxygen) hexahydrofurano[3,2-b]furan-3-ol

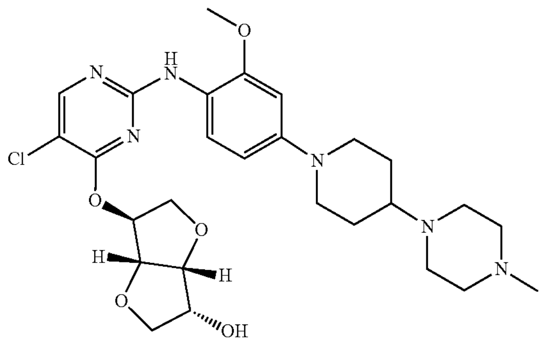 [SMILES: COc1cc(N2CCC(N3CCN(C)CC3)CC2)ccc1Nc1ncc(Cl)c(O[C@H]2CO[C@H]3[C@@H]2OC[C@H]3O)n1]

The synthesis method was the same as that of LS 3-96 in Example 1, except that 4-fluoro-2-methoxy-1-nitrobenzene was used instead of 2-chloro-1-fluoro-4-nitrobenzene (5) in the reaction.

$^1$H NMR (400 MHz, $CDCl_3$) δ 8.13 (s, 1H), 8.07 (d, J=9.6 Hz, 1H), 7.40 (s, 1H), 6.59-6.49 (m, 2H), 5.57 (d, J=3.2 Hz, 1H), 4.76 (t, J=4.8 Hz, 1H), 4.70 (d, J=4.4 Hz, 1H), 4.36 (q, J=1.6 Hz, 1H), 4.27 (d, J=10.8 Hz, 1H), 4.15 (dd, J=10.7, 3.7 Hz, 1H), 3.94 (dd, J=9.2, 5.6 Hz, 1H), 3.88 (s, 3H), 3.74-3.61 (m, 3H), 2.79-2.45 (m, 14H), 1.95 (d, J=12.8 Hz, 2H), 1.77-1.68 (m, 2H). MS (ESI) m/z 561.3 $[M+H]^+$.

Example 4

Synthesis of (3R,3aR,6S, 6aR)-6-(5-chloro-2-((3-methoxy-4-(4-methylpiperazin-1-yl) phenyl)amino) pyrimidin-4-yl) oxygen) hexahydrofurano[3,2-b] furan-3-ol (LS 4-106)

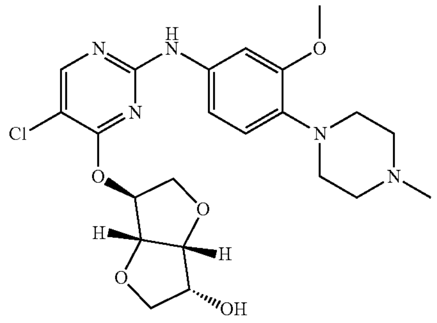 [SMILES: COc1cc(Nc2ncc(Cl)c(O[C@H]3CO[C@H]4[C@@H]3OC[C@H]4O)n2)ccc1N1CCN(C)CC1]

The synthesis method was the same as that of LS 3-96 in Example 1, except that 1-fluoro-2-methoxy-4-nitrobenzene was used instead of 2-chloro-1-fluoro-4-nitrobenzene (5), and N-methylpiperazine instead of 1-methyl-4-(piperidyl-4-yl) piperazine hydrochloride (6) in the reaction.

$^1$H NMR (400 MHz, $CDCl_3$) δ 8.14 (s, 1H), 7.11 (d, J=2.4 Hz, 1H), 7.06 (dd, J=8.8, 2.4 Hz, 1H), 6.98 (s, 1H), 6.91 (d, J=8.4 Hz, 1H), 5.56 (d, J=3.6 Hz, 1H), 4.75 (t, J=4.8 Hz, 1H), 4.67 (d, J=4.4 Hz, 1H), 4.40-4.31 (m, 1H), 4.23 (d, J=10.8 Hz, 1H), 4.12 (dd, J=10.8, 4.0 Hz, 1H), 3.93 (dd, J=9.6, 6.0 Hz, 1H), 3.88 (s, 3H), 3.64 (dd, J=9.6, 6.0 Hz, 1H), 3.08 (s, 4H), 2.63 (s, 5H), 2.36 (s, 3H). MS (ESI) m/z 478.2 $[M+H]^+$.

Example 5

Synthesis of 1-(4-(5-chloro-4-(((3R,3aR,6R, 6aR)-6-hydroxyhexahydrofurano[3,2-b]furan-3-yl) oxygen)pyrimidin-2-yl)amino)phenyl)cyclopentane-1-acetonitrile (LS 5-58)

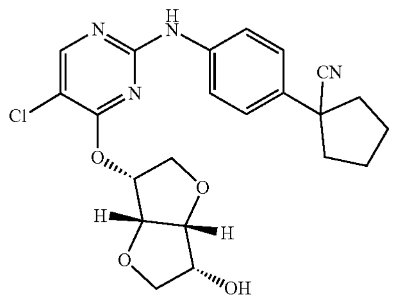 [SMILES: N#CC1(c2ccc(Nc3ncc(Cl)c(O[C@@H]4CO[C@H]5[C@@H]4OC[C@H]5O)n3)cc2)CCCC1]

The synthesis method was the same as that of LS 3-96 in Example 1, except that 1,4:3,6-bis dehydrated mannitol was used instead of isosorbitol (2), and 1-(4-aminophenyl)cyclopentane-1-acetonitrile instead of 3-chloro-4-(4-(4-methylpiperazin-1-yl) piperidin-1-yl) aniline (4) to participate in the reaction.

$^1$H NMR (400 MHz, $CDCl_3$) δ 8.16 (s, 1H), 7.52 (d, J=8.4 Hz, 2H), 7.44 (s, 1H), 7.40 (d, J=8.4 Hz, 2H), 5.52 (q, J=5.6 Hz, 1H), 4.89 (t, J=5.2 Hz, 1H), 4.53 (t, J=5.2 Hz, 1H), 4.34-4.25 (m, 1H), 4.17 (d, J=5.2 Hz, 2H), 3.98 (dd, J=8.8, 6.4 Hz, 1H), 3.67-3.58 (m, 1H), 2.52-2.44 (m, 2H), 2.09-1.90 (m, 6H). HRMS (ESI) calcd for $C_{22}H_{24}ClN_4O_4[M+H]^+$ 443.1481; found 443.1465.

Example 6

Synthesis of (3R,3aR,6R, 6aR)-6-(5-chloro-2-((4-(4-methylpiperazin-1-yl)phenyl)amino)pyrimidin-4-yl) oxygen) hexahydrofurano[3,2-b]furan-3-ol (LS 4-144)

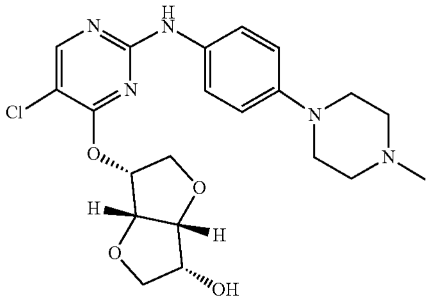 [SMILES: CN1CCN(c2ccc(Nc3ncc(Cl)c(O[C@@H]4CO[C@H]5[C@@H]4OC[C@H]5O)n3)cc2)CC1]

The synthesis method was the same as that of LS 3-96 in Example 1, except that 1,4:3,6-bis dehydrated mannitol was used instead of isosorbitol (2), and 4-(4-methylpiperazin-1-yl) aniline instead of 3-chloro-4-(4-(4-methylpiperazin-1-yl) piperazin-1-yl) aniline (4) in the reaction.

$^1$H NMR (400 MHz, $CDCl_3$) δ 8.12 (s, 1H), 7.40-7.33 (m, 2H), 6.95-6.85 (m, 3H), 5.46 (q, J=5.6 Hz, 1H), 4.85 (t, J=5.2 Hz, 1H), 4.51 (t, J=5.2 Hz, 1H), 4.33-4.25 (m, 1H), 4.17 (dd, J=10.0, 6.0 Hz, 1H), 4.10 (dd, J=10.0, 5.6 Hz, 1H), 3.98 (dd, J=9.2, 6.4 Hz, 1H), 3.63 (dd, J=9.2, 8.0 Hz, 1H), 3.29-3.20 (m, 4H), 2.78-2.68 (m, 4H), 2.46 (s, 3H). HRMS (ESI) calcd for $C_{21}H_{27}ClN_5O_4$ $[M+H]^+$ 448.1746; found 448.1734.

Example 7

Synthesis of (3R,3aR,6R, 6aR)-6-(5-chloro-2-((3-chloro-4-(4-methylpiperazin-1-yl)phenyl)amino) pyrimidin-4-yl) oxygen) hexahydrofurano[3,2-b] furan-3-ol (LS 4-142)

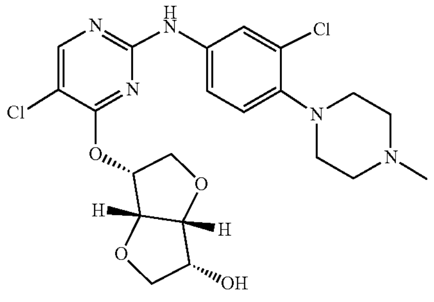 [SMILES: CN1CCN(c2ccc(Nc3ncc(Cl)c(O[C@@H]4CO[C@H]5[C@@H]4OC[C@H]5O)n3)cc2Cl)CC1]

The synthesis method was the same as that of LS 3-96 in Example 1, except that 1,4:3,6-bis dehydrated mannitol was used instead of isosorbitol (2), and 3-chloro-4-(4-methylpiperazin-1-yl) aniline instead of 3-chloro-4-(4-(4-methylpiperazin-1-yl) piperidin-1-yl) aniline (4) in the reaction.

$^1$H NMR (400 MHz, $CDCl_3$) δ 8.15 (s, 1H), 7.79 (d, J=2.8 Hz, 1H), 7.17 (dd, J=8.8, 2.8 Hz, 1H), 7.06 (s, 1H), 7.02 (d, J=8.8 Hz, 1H), 5.49 (q, J=5.6 Hz, 1H), 4.93 (t, J=5.6 Hz, 1H), 4.54 (t, J=5.6 Hz, 1H), 4.30 (dd, J=12.8, 6.4 Hz, 1H), 4.22-4.12 (m, 2H), 3.98 (dd, J=9.2, 6.4 Hz, 1H), 3.63 (dd, J=8.8, 8.0 Hz, 1H), 3.11 (s, 4H), 2.71 (s, 4H), 2.43 (s, 3H). HRMS (ESI) calcd for $C_{21}H_{26}Cl_2N_5O_4$ $[M+H]^+$ 482.1356; found 482.1330.

Example 8

Synthesis of (3R,3aR,6R, 6aR)-6-(5-Chloro-2-((4-(4-(4-methylpiperazin-1-yl) piperidin-1-yl)phenyl) amino)pyrimidin-4-yl) oxygen) hexahydrofurano[3, 2-b]furan-3-ol (LS 4-145)

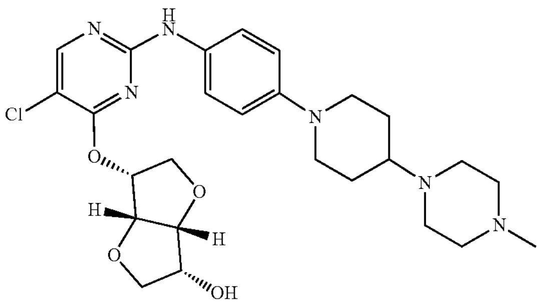 [SMILES: CN1CCN(C2CCN(c3ccc(Nc4ncc(Cl)c(O[C@@H]5CO[C@H]6[C@@H]5OC[C@H]6O)n4)cc3)CC2)CC1]

The synthesis method was the same as that of LS 3-96 in Example 1, except that 1,4:3,6-bis dehydrated mannitol was used instead of isosorbitol (2), and 4-(4-(4-methylpiperazin-1-yl) piperidin-1-yl) aniline instead of 3-chloro-4-(4-(4-methylpiperazin-1-yl) piperidin-1-yl) aniline (4) in the reaction.

$^1$H NMR (400 MHz, $CDCl_3$) δ 8.14 (s, 1H), 7.40-7.32 (m, 2H), 6.97-6.90 (m, 2H), 6.87 (s, 1H), 5.48 (q, J=5.6 Hz, 1H), 4.87 (t, J=5.6 Hz, 1H), 4.53 (t, J=5.6 Hz, 1H), 4.31 (m, 1H), 4.19 (dd, J=9.6, 5.6 Hz, 1H), 4.12 (dd, J=10.0, 5.6 Hz, 1H), 4.00 (dd, J=9.2, 6.8 Hz, 1H), 3.76-3.61 (m, 3H), 2.91-2.56 (m, 10H), 2.50-2.44 (m, 1H), 2.42 (s, 3H), 1.99 (d, J=12.8 Hz, 2H), 1.77-1.67 (m, 2H). HRMS (ESI) calcd for $C_{26}H_{36}ClN_6O_4[M+H]^+$ 531.2481; found 531.2457.

Example 9

Synthesis of (3R,3aR,6R, 6aR)-6-(5-Chloro-2-((3-methoxy-4-(4-(4-methylpiperazin-1-yl) piperidin-1-yl)phenyl)amino)pyrimidin-4-yl) oxygen) hexahydrofurano[3,2-b]furan-3-ol (LS 4-143)

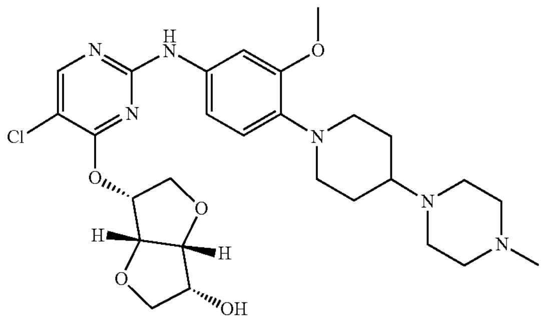 [SMILES: COc1cc(Nc2ncc(Cl)c(O[C@@H]3CO[C@H]4[C@@H]3OC[C@H]4O)n2)ccc1N1CCC(N2CCN(C)CC2)CC1]

The synthesis method was the same as that of LS 3-96 in Example 1, except that 1,4:3,6-bis dehydrated mannitol was used instead of isosorbitol (2), and 3-methoxy-4-(4-(4-methylpiperazin-1-yl) piperidin-1-yl) aniline instead of 3-chloro-4-(4-(4-methylpiperazin-1-yl) piperidin-1-yl) aniline (4) in the reaction.

$^1$H NMR (400 MHz, $CDCl_3$) δ 8.13 (s, 1H), 7.06-6.94 (m, 3H), 6.88 (d, J=8.4 Hz, 1H), 5.47 (q, J=5.6 Hz, 1H), 4.83 (t, J=5.2 Hz, 1H), 4.49 (t, J=5.6 Hz, 1H), 4.32-4.23 (m, 1H), 4.16 (dd, J=10.0, 6.0 Hz, 1H), 4.08 (dd, J=10.0, 5.6 Hz, 1H), 3.97 (dd, J=9.2, 6.4 Hz, 1H), 3.85 (s, 3H), 3.63 (dd, J=9.2, 8.0 Hz, 1H), 3.49 (d, J=11.6 Hz, 2H), 2.75-2.45 (m, 11H), 2.31 (s, 3H), 1.90 (d, J=11.2 Hz, 2H), 1.85-1.75 (m, 2H). HRMS (ESI) calcd for $C_{27}H_{38}ClN_6O_5[M+H]^+$ 561.2587; found 561.2556.

Example 10

Synthesis of (3R,3aR,6R, 6aR)-6-(5-chloro-2-((2-chloro-4-(4-(4-methylpiperazin-1-yl) piperidin-1-yl) phenyl)amino) pyrimidin-4-yl) oxygen) hexahydrofurano[3,2-b]furan-3-ol (LS 4-148)

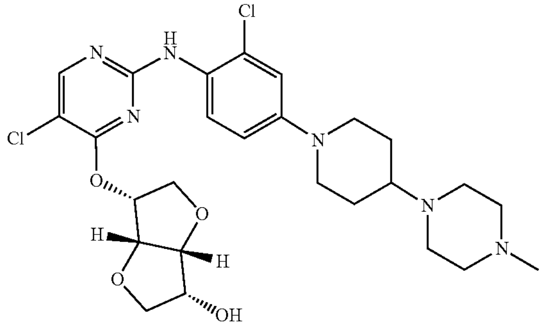 [SMILES: CN1CCN(C2CCN(c3ccc(Nc4ncc(Cl)c(O[C@@H]5CO[C@H]6[C@@H]5OC[C@H]6O)n4)c(Cl)c3)CC2)CC1]

The synthesis method was the same as that of LS 3-96 in Example 1, except that 1,4:3,6-bis dehydrated mannitol was used instead of isosorbitol (2), and 2-chloro-4-(4-(4-methylpiperazin-1-yl) piperidin-1-yl) aniline instead of 3-chloro-4-(4-(4-methylpiperazin-1-yl) piperidin-1-yl) aniline (4) in the reaction.

$^1$H NMR (400 MHz, $CDCl_3$) δ 8.14 (s, 1H), 7.93 (d, J=9.2 Hz, 1H), 7.08 (s, 1H), 6.94 (d, J=2.8 Hz, 1H), 6.84 (dd, J=9.2, 2.8 Hz, 1H), 5.47 (q, J=5.6 Hz, 1H), 4.84 (t, J=5.2 Hz, 1H), 4.50 (t, J=5.2 Hz, 1H), 4.33-4.24 (m, 1H), 4.16 (dd, J=10.0, 6.0 Hz, 1H), 4.09 (dd, J=9.6, 5.2 Hz, 1H), 3.97 (dd, J=9.2, 6.8 Hz, 1H), 3.72-3.59 (m, 3H), 2.76-2.45 (m, 10H), 2.34-2.28 (m, 4H), 1.94 (d, J=12.0 Hz, 2H), 1.70-1.60 (m, 2H). HRMS (ESI) calcd for $C_{26}H_{35}Cl_2N_6O_4$ $[M+H]^+$ 565.2091; found 565.2068.

Example 11

Synthesis of (3R,3aR,6R, 6aR)-6-(5-Chloro-2-(3,5-Dichloro-4-(4-(4-methylpiperazin-1-yl) piperidin-1-yl)phenyl)amino) pyrimidin-4-yl) oxygen) hexahydrofurano[3,2-b]furan-3-ol (LS 5-16)

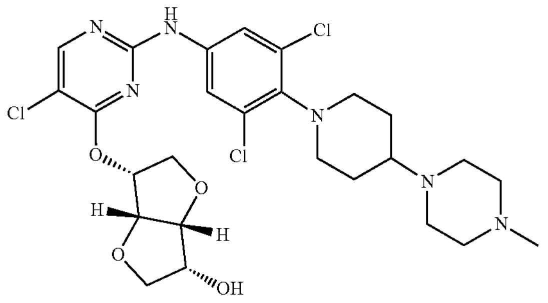 [SMILES: CN1CCN(C2CCN(c3c(Cl)cc(Nc4ncc(Cl)c(O[C@@H]5CO[C@H]6[C@@H]5OC[C@H]6O)n4)cc3Cl)CC2)CC1]

The synthesis method was the same as that of LS 3-96 in Example 1, except that 1,4:3,6-bis dehydrated mannitol was used instead of isosorbitol (2), and 3,5-dichloro-4-(4-(4-methylpiperazin-1-yl) piperidin-1-yl) aniline instead of 3-chloro-4-(4-(4-methylpiperazin-1-yl) piperidin-1-yl) aniline (4) to participate in the reaction.

$^1$H NMR (400 MHz, $CDCl_3$) δ 8.17 (s, 1H), 7.55 (d, J=2.4 Hz, 1H), 7.43 (d, J=2.4 Hz, 1H), 7.05 (s, 1H), 5.49 (q, J=5.2 Hz, 1H), 4.96 (t, J=5.2 Hz, 1H), 4.55 (t, J=5.6 Hz, 1H), 4.36-4.26 (m, 1H), 4.18 (d, J=5.6 Hz, 2H), 3.98 (dd, J=9.2, 6.8 Hz, 1H), 3.63 (dd, J=8.8, 8.0 Hz, 1H), 3.33 (t, J=11.6 Hz, 2H), 3.03 (d, J=11.6 Hz, 2H), 2.85-2.25 (m, 13H), 1.87 (d, J=10.8 Hz, 5H), 1.74-1.67 (m, 2H). HRMS (ESI) calcd for $C_{26}H_{34}C_{13}N_6O_4$ $[M+H]^+$ 599.1702; found 599.1694.

Example 12

Synthesis of (3R,3aR,6R,6aR)-6-(5-Chloro-2-((5-methyl-6-(4-(4-methylpiperazin-1-yl) piperidin-1-yl) pyridine-3-yl)amino)pyrimidin-4-yl) oxygen) hexahydrofurano[3,2-b]furan-3-ol (LS 4-150)

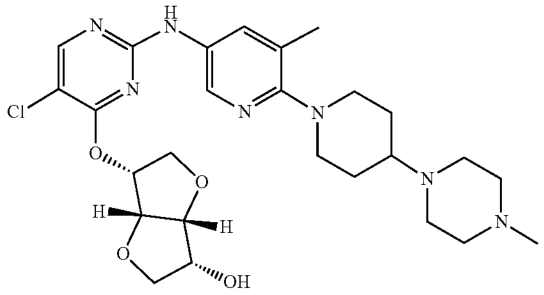 [SMILES: Cc1cc(Nc2ncc(Cl)c(O[C@@H]3CO[C@H]4[C@@H]3OC[C@H]4O)n2)cnc1N1CCC(N2CCN(C)CC2)CC1]

The synthesis method was the same as that of LS 3-96 in Example 1, except that 1,4:3,6-bis dehydrated mannitol was used instead of isosorbitol (2), and 5-methyl-6-(4-(4-methylpiperazin-1-yl) piperidin-1-yl)pyridine-3-amino instead of 3-chloro-4-(4-(4-methylpiperazin-1-yl) piperidin-1-yl) aniline (4) to participate in the reaction.

$^1$H NMR (400 MHz, $CDCl_3$) δ 8.23 (d, J=2.4 Hz, 1H), 8.11 (s, 1H), 7.62 (d, J=2.0 Hz, 1H), 7.06 (s, 1H), 5.46 (q, J=5.6 Hz, 1H), 4.84 (t, J=5.2 Hz, 1H), 4.49 (t, J=5.6 Hz, 1H), 4.27 (dt, J=8.0, 6.4 Hz, 1H), 4.17-4.06 (m, 2H), 3.96 (dd, J=9.2, 6.4 Hz, 1H), 3.61 (dd, J=8.8, 8.4 Hz, 1H), 3.41 (d, J=12.8 Hz, 2H), 2.87-2.57 (m, 7H), 2.43-2.13 (m, 10H), 1.95 (d, J=11.6 Hz, 2H), 1.74-1.58 (m, 2H). MS (ESI) m/z 546.3 $[M+H]^+$.

Example 13

Synthesis of (3R,3aR,6R, 6aR)-6-(5-chloro-2-((5-((4-ethylpiperazin-1-yl)methyl)pyridin-2-yl)amino) pyrimidin-4-yl) oxygen) hexahydrofurano[3,2-b] furan-3-ol (LS 5-54)

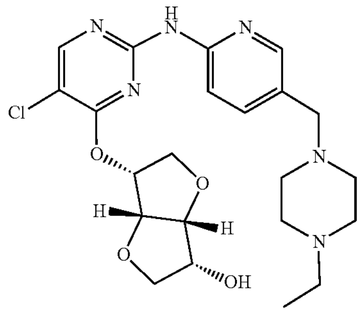 [SMILES: CCN1CCN(Cc2ccc(Nc3ncc(Cl)c(O[C@@H]4CO[C@H]5[C@@H]4OC[C@H]5O)n3)nc2)CC1]

The synthesis method was the same as that of LS 3-96 in Example 1, except that 1,4:3,6-bis dehydrated mannitol was used instead of isosorbitol (2), and 5-((4-ethylpiperazin-1-yl)methyl)pyridine-2-amino instead of 3-chloro-4-(4-(4-methylpiperazin-1-yl) piperazin-1-yl) aniline (4) in the reaction.

$^1$H NMR (400 MHz, $CDCl_3$) δ 8.29-8.22 (m, 2H), 8.22 (d, J=1.6 Hz, 1H), 8.19 (d, J=8.4 Hz, 1H), 7.66 (dd, J=8.8, 2.4 Hz, 1H), 5.53 (q, J=5.6 Hz, 1H), 4.90 (t, J=5.2 Hz, 1H), 4.54 (t, J=5.6 Hz, 1H), 4.35-4.26 (m, 1H), 4.21 (dd, J=10.0, 5.6 Hz, 1H), 4.15 (dd, J=10.0, 5.2 Hz, 1H), 3.97 (dd, J=8.8, 6.4 Hz, 1H), 3.64 (dd, J=8.8, 8.0 Hz, 1H), 3.49 (s, 2H), 2.74-2.45 (m, 10H), 1.14 (t, J=7.2 Hz, 3H). HRMS (ESI) calcd for $C_{22}H_{30}ClN_6O_4[M+H]^+$ 477.2012; found 477.2020.

Example 14

Synthesis of N-(3-(5-chloro-4-(((3R,3aR,6R, 6aR)-6-hydroxyhexahydrofurano[3,2-b]furan-3-yl) oxygen) pyrimidin-2-yl)amino)phenyl) acrylamide (LS 5-77)

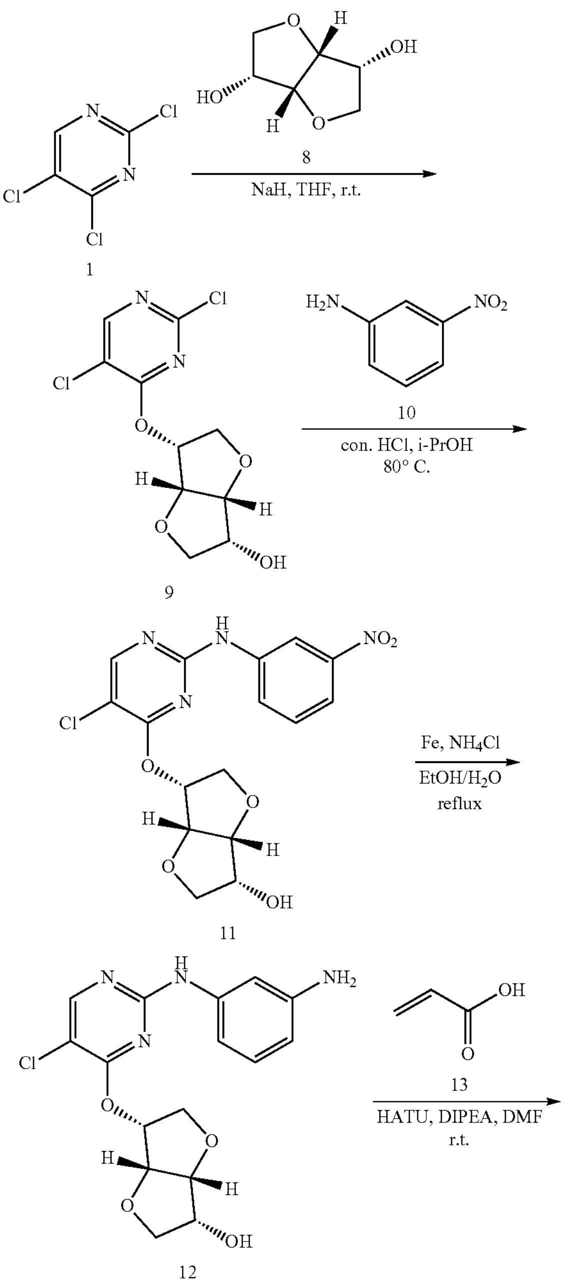

-continued

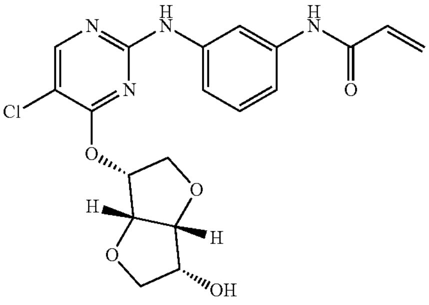

LS 5-77

Step 1 Synthesis of (3R,3aR,6R, 6aR)-6-(2,5-dichloropyrimidin-4-yl) oxygen) hexahydrofurano[3,2-b]furan-3-ol (9)

The synthesis method was the same as that of compound 3-1 in Example 1, except that 1,4:3,6-bis dehydrated mannitol (8) was used instead of isosorbitol (2) to participate in the reaction.

$^1$H NMR (400 MHz, DMSO-$d_6$) δ 8.68 (s, 1H), 5.51 (td, J=5.2, 4.0 Hz, 1H), 4.80 (t, J=5.2 Hz, 1H), 4.28 (t, J=4.8 Hz, 1H), 4.14-3.90 (m, 3H), 3.70 (t, J=7.6 Hz, 1H), 3.34 (dd, J=9.6, 8.0 Hz, 1H). MS (ESI) m/z 293.0 $[M+H]^+$.

Figure 2:
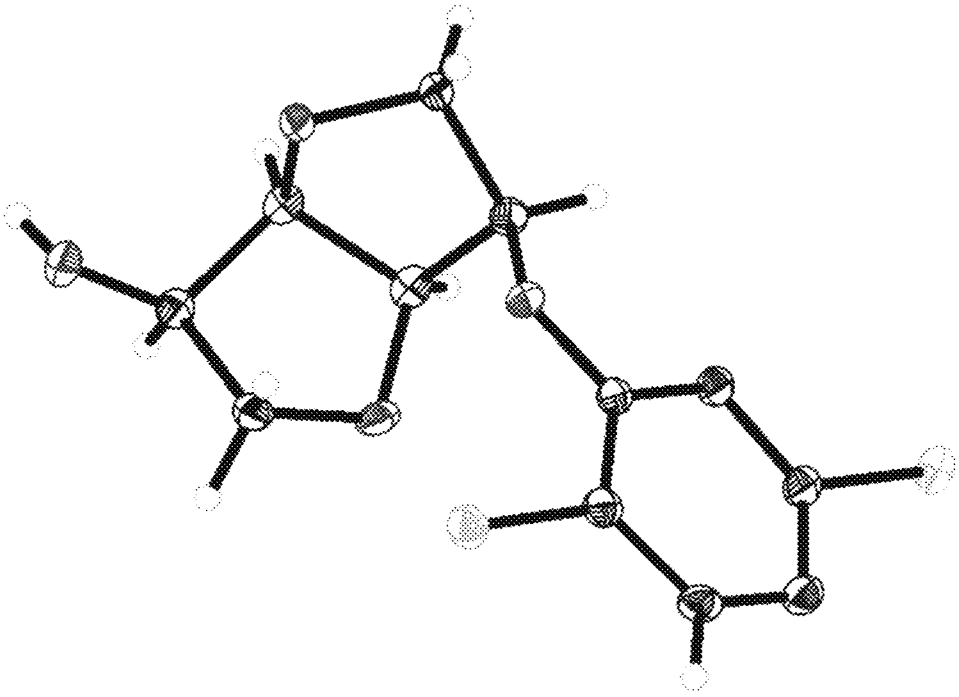
FIG. 2 shows the single crystal structure of intermediate 9.

The crystal structure and analysis of intermediate 9 are shown in FIG. 2 (CCDC number 2119315) and Table 2, confirming that its chemical structure (stereo configuration) was correct.

TABLE 2

Single crystal parameters of Intermediate 9

| | No. 9 |
|---|---|
| Molecular formula | $C_{10}H_{10}Cl_2N_2O_4$ |
| Molecular weight | 293.10 |
| Temperature/K | 100.00 (10) |
| Crystal system | tetragonal |
| Space group | $P4_3$ |
| a/Å | 9.49090 (10) |
| b/Å | 9.49090 (10) |
| c/Å | 12.5117 (2) |
| α/° | 90 |
| β/° | 90 |
| γ/° | 90 |
| Cell volume/Å$^3$ | 1127.02 (3) |
| Z | 4 |
| $\rho_{calc}$ g/cm$^3$ | 1.727 |
| μ/mm$^{-1}$ | 5.305 |
| F(000) | 600.0 |
| Crystal size/mm$^3$ | 0.12 × 0.11 × 0.1 |
| Illuminant | CuKα (λ = 1.54184) |
| 2θ Data collection scope/° | 9.318 to 147.066 |
| Index range | −11 ≤ h ≤ 11, −8 ≤ k ≤ 10, −15 ≤ l ≤ 15 |
| Diffraction collection | 5021 |
| Independent diffraction | 2179 [$R_{int}$ = 0.0212, $R_{sigma}$ = 0.0236] |
| Data/Restrictions/Parameters | 2179/1/164 |
| Goodness of fit F$^2$ | 1.077 |
| Final R index[I >= 2σ (I)] | $R_1$ = 0.0238, $wR_2$ = 0.0586 |
| Final R index[full data] | $R_1$ = 0.0242, $wR_2$ = 0.0590 |
| Maximum residual electron density peak/e Å$^{-3}$ | 0.19/−0.26 |
| Flack parameter | 0.015 (7) |

Step 2 Synthesis of (3R,3aR,6R, 6aR)-6-(5-chloro-2-((3-nitrophenyl)amino)pyrimidin-4-yl) oxygen) hexahydrofurano[3,2-b]furan-3-ol (11)

2-Nitroaniline (10, 0.13 g, 0.98 mmol) and concentrated hydrochloric acid (1.13 mmol) were added into an isopropanol solution of intermediate 9 (0.3 g, 1.0 mmol), and the temperature was raised to 80° C. for overnight reaction. After the reaction was complete, the system was cooled to room temperature, spin-dried most of the solvent, extracted three times with dichloromethane; the organic phases were combined, washed with saturated salt water, dried over anhydrous sodium sulfate, and then concentrated under reduced pressure. The residue was then purified by silica gel column chromatography to obtain solid 11 (0.18 g, 46%).

$^1$H NMR (400 MHz, DMSO-$d_6$) δ 10.26 (s, 1H), 8.85 (t, J=2.4 Hz, 1H), 8.43 (s, 1H), 7.95 (d, J=8.4 Hz, 1H), 7.83 (dd, J=8.0, 2.4 Hz, 1H), 7.59 (t, J=8.2 Hz, 1H), 5.53 (dd, J=10.8, 5.2 Hz, 1H), 4.99 (d, J=6.8 Hz, 1H), 4.88 (t, J=5.2 Hz, 1H), 4.34 (t, J=4.8 Hz, 1H), 4.14-4.04 (m, 2H), 3.99 (dd, J=10.0, 4.8 Hz, 1H), 3.79-3.69 (m, 1H), 3.40 (t, J=8.4 Hz, 1H). MS (ESI) m/z 395.1 $[M+H]^+$.

Step 3 Synthesis of (3R,3aR,6R, 6aR)-6-(2-(((3-aminophenyl)amino)-5-chloropyrimidin-4-yl) oxygen) hexahydrofurano[3,2-b]furan-3-ol (12)

Reduced iron powder (64 mg, 1.14 mmol) and ammonium chloride (0.2 g, 3.8 mmol) were added to a mixed solvent of ethanol/water (2:1 by volume) of intermediate 11 (0.15 g, 0.38 mmol), refluxed and reacted for 2 hours. After the reaction was complete, the mixture was cooled to room temperature and filtered over a pad of Celite. The volatiles were removed under reduced pressure and the residue was extracted three times with dichloromethane. The organic phases were combined, washed with saturated salt water, dried over anhydrous sodium sulfate, and then concentrated under reduced pressure. The residue was then purified by silica gel column chromatography to obtain solid 12 (0.11 g, 79%).

$^1$H NMR (400 MHz, DMSO-$d_6$) δ 9.39 (s, 1H), 8.25 (s, 1H), 6.96 (t, J=2.0 Hz, 1H), 6.91 (t, J=8.0 Hz, 1H), 6.77 (d, J=8.0 Hz, 1H), 6.20 (dd, J=8.0, 1.2 Hz, 1H), 5.44 (dd, J=11.2, 5.6 Hz, 1H), 5.00 (s, 2H), 4.95 (d, J=6.8 Hz, 1H), 4.82 (t, J=5.2 Hz, 1H), 4.31 (t, J=4.8 Hz, 1H), 4.13-4.00 (m, 2H), 3.93 (dd, J=9.6, 5.2 Hz, 1H), 3.76-3.68 (m, 1H), 3.42-3.35 (m, 1H). MS (ESI) m/z 365.1 $[M+H]^+$.

Step 4 Synthesis of N-(3-(5-chloro-4-((((3R,3aR, 6R, 6aR)-6-hydroxyhexahydrofurano-[3,2b]furan-3-yl)oxy) pyrimidin-2-yl)amino)phenyl) acrylamide (LS 5-77)

Acrylic acid (13, 20 mg, 0.27 mmol), O-(7-azobenzotriazol-1-oxide)-N,N",N"-tetramethylurea hexafluorophosphate (HATU, 0.12 g, 0.3 mmol), and N, N-diisopropylethylamine (DIPEA, 64 mg, 0.5 mmol) were added to a DMF solution of intermediate 12 (90 mg, 0.25 mmol), and stirred to react overnight at room temperature. After the reaction was complete, most of the solvents were removed under reduced pressure. The crude product was extracted three times with dichloromethane, the organic phases were combined, washed with saturated salt water, dried over anhydrous sodium sulfate, and then concentrated under reduced pressure. The residue was then purified by silica gel column chromatography to obtain a white solid.

$^1$H NMR (400 MHz, DMSO-$d_6$) δ 10.10 (s, 1H), 9.75 (s, 1H), 8.31 (s, 2H), 7.28 (d, J=8.0 Hz, 1H), 7.22 (t, J=8.0 Hz, 1H), 7.13 (d, J=7.6 Hz, 1H), 6.46 (dd, J=16.8, 10.0 Hz, 1H), 6.25 (dd, J=16.8, 2.0 Hz, 1H), 5.75 (dd, J=10.0, 2.0 Hz, 1H), 5.65 (q, J=5.2 Hz, 1H), 4.94 (d, J=6.8 Hz, 1H), 4.82 (t, J=5.2 Hz, 1H), 4.26 (t, J=4.8 Hz, 1H), 4.13-4.00 (m, 2H), 3.94 (dd, J=9.6, 5.2 Hz, 1H), 3.72 (t, J=7.4 Hz, 1H), 3.38 (t, J=8.4 Hz, 1H). $^{13}$C NMR (151 MHz, DMSO-$d_6$) δ 163.76 (s), 163.52 (s), 158.17 (s), 157.11 (s), 140.78 (s), 139.63 (s), 132.36 (s), 129.15 (s), 127.27 (s), 115.16 (s), 113.73 (s), 110.72 (s), 105.22 (s), 81.98 (s), 80.72 (s), 77.40 (s), 72.33 (s), 71.47 (s), 70.95 (s). HRMS (ESI) calcd for $C_{19}H_{20}ClN_4O_5$ [M+H]$^+$ 419.1117; found 419.1126.

Example 15

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-fluorophenyl) acrylamide (LS 5-62)

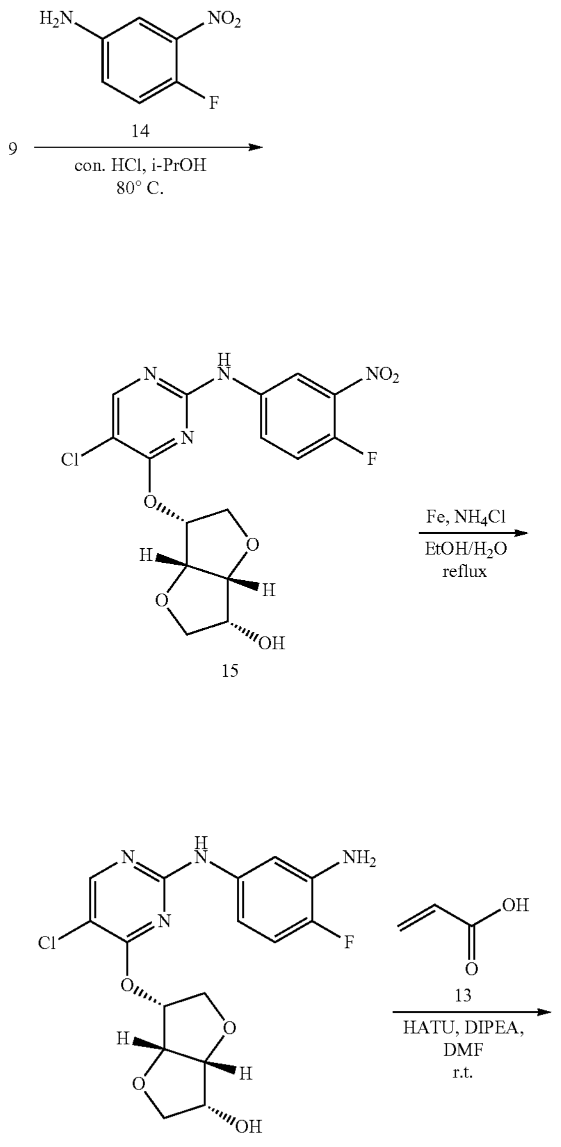

14
15
13
16

-continued

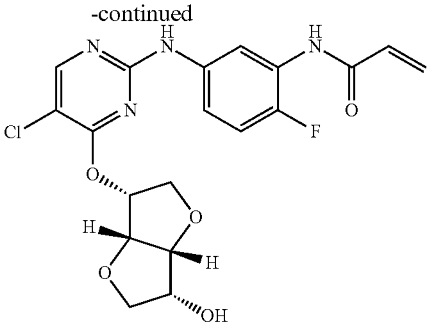

LS 5-62

Step 1 Synthesis of (3R,3aR,6R, 6aR)-6-(5-chloro-2-((4-fluoro-3-nitrophenyl)amino)pyrimidin-4-yl) oxygen) hexahydrofurano[3,2-b]furan-3-ol (15)

The synthesis method was the same as that of compound 11, except that raw material 14 was used instead of m-nitroaniline (10) to participate in the reaction.

$^1$H NMR (400 MHz, $CDCl_3$) δ 8.84 (dd, J=6.4, 2.8 Hz, 1H), 8.20 (s, 1H), 7.81 (s, 1H), 7.45 (dt, J=8.8, 3.2 Hz, 1H), 7.26-7.19 (m, 1H), 5.68-5.59 (m, 1H), 5.00 (t, J=5.6 Hz, 1H), 4.58 (t, J=5.6 Hz, 1H), 4.33-4.27 (m, 1H), 4.24 (dd, J=10.4, 4.4 Hz, 1H), 4.18 (dd, J=10.0, 5.2 Hz, 1H), 3.96 (dd, J=8.8, 6.4 Hz, 1H), 3.62 (dd, J=8.8, 8.0 Hz, 1H). MS (ESI) m/z 413.1 [M+H]$^+$.

Step 2 Synthesis of (3R,3aR,6R, 6aR)-6-(2-(((3-amino-4-fluorophenyl)amino)-5-chloropyrimidin-4-yl) oxygen) hexahydrofurano[3,2-b]furan-3-ol (16)

The synthesis method was the same as that of compound 12.

$^1$H NMR (400 MHz, DMSO-$d_6$) δ 9.44 (s, 1H), 8.25 (s, 1H), 7.12 (dd, J=8.4, 2.4 Hz, 1H), 6.88 (dd, J=11.2, 8.8 Hz, 1H), 6.79-6.70 (m, 1H), 5.44 (dd, J=10.8, 5.2 Hz, 1H), 5.09 (s, 2H), 4.95 (d, J=7.2 Hz, 1H), 4.80 (t, J=5.2 Hz, 1H), 4.31 (t, J=5.2 Hz, 1H), 4.12-4.01 (m, 2H), 3.93 (dd, J=9.6, 4.8 Hz, 1H), 3.75-3.68 (m, 1H), 3.42-3.35 (m, 1H). MS (ESI) m/z 383.1 [M+H]$^+$.

Step 3 Synthesis of N-(5-(5-chloro-4-(((3R,3aR,6R, 6aR)-6-hydroxyhexahydrofurano-[3,2b]furan-3-yl) oxy) pyrimidin-2-yl)amino)-2-fluorophenyl) acrylamide (LS 5-62)

Acrylic acid (13.13 mg, 0.18 mmol), O-(7-azobenzotriazol-1-oxide)-N,N",N"-tetramethylurea hexafluorophosphate (HATU, 74 mg, 0.19 mmol), and N, N-diisopropylethylamine (DIPEA, 42 mg, 0.32 mmol) were added to a DMF solution of intermediate 16 (62 mg, 0.16 mmol), stirred to react overnight at room temperature. After the reaction was complete, most of the solvents were removed under reduced pressure. The crude product was extracted three times with dichloromethane, the organic phases were combined, washed with saturated salt water, dried over anhydrous sodium sulfate, spin-dried, and separated by column chromatography to obtain a white solid.

$^1$H NMR (400 MHz, $CDCl_3$) δ 8.76 (s, 1H), 8.07 (s, 1H), 7.06-6.92 (m, 2H), 6.42-6.26 (m, 2H), 5.83 (q, J=5.2 Hz, 1H), 5.75 (dd, J=8.8, 2.8 Hz, 1H), 4.87 (t, J=5.2 Hz, 1H), 4.39 (t, J=5.2 Hz, 1H), 4.25-4.04 (m, 3H), 3.87 (dd, J=8.8, 6.4 Hz, 1H), 3.55 (t, J=8.4 Hz, 1H), 3.36-3.30 (m, 1H). $^{13}$C

NMR (151 MHz, DMSO-$d_6$) δ 163.91 (s), 163.79 (s), 158.08 (s), 157.21 (s), 149.32 (d, J=240.7 Hz), 136.60 (s), 131.79 (s), 127.92 (s), 126.02 (d, J=12.4 Hz), 116.45 (d, J=6.9 Hz), 115.66 (d, J=20.6 Hz), 114.98 (s), 105.18 (s), 81.99 (s), 80.73 (s), 77.38 (s), 72.29 (s), 71.44 (s), 71.00 (s). HRMS (ESI) calcd for $C_{19}H_{19}ClFN_4O_5[M+H]^+$437.1023; found 437.1033.

Example 16

Synthesis of N-(5-(5-chloro-4-((3R,3aR,6R,6aR)-6-hydroxyhexahydrofurano[3,2-b]furan-3-yl) oxygen) pyrimidin-2-yl)amino)-2-fluorophenyl) acrylamide (LS 5-12)

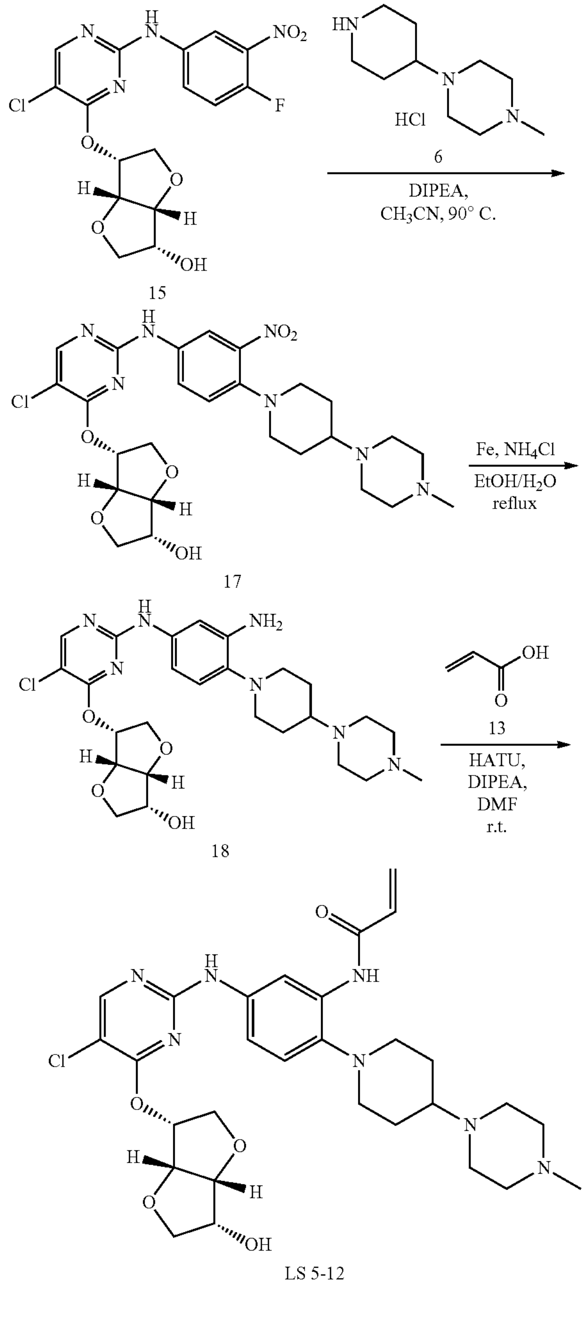

6
15
17
13
18
LS 5-12

Step 1 Synthesis of (3R,3aR,6R,6aR)-6-(5-chloro-2-((4-fluoro-3-nitrophenyl)amino)pyrimidin-4-yl) oxygen) hexahydrofurano[3,2-b]furan-3-ol (17)

1-methyl-4-(piperidin-4-yl) piperazine hydrochloride (6, 0.32 g, 1.45 mmol) and N, N-diisopropylethylamine (DIPEA, 0.38 g, 2.9 mmol) were added to the acetonitrile solution of intermediate 15 (0.4 g, 0.97 mmol). The temperature of the system was raised to 90° C. to react overnight. After the reaction is complete, cooled to room temperature, spin-dried most of the solvent, extracted three times with dichloromethane. The organic phases were merged, washed with saturated salt water, dried over anhydrous sodium sulfate, spin-dried, and separated by column chromatography to obtain a solid 17.

$^1$H NMR (400 MHz, $CDCl_3$) δ 8.51 (d, J=2.4 Hz, 1H), 8.17 (s, 1H), 7.34 (dd, J=8.8, 2.4 Hz, 1H), 7.22 (s, 1H), 7.12 (d, J=8.8 Hz, 1H), 5.59 (q, J=5.2 Hz, 1H), 4.97 (t, J=5.4 Hz, 1H), 4.57 (t, J=5.4 Hz, 1H), 4.34-4.24 (m, 1H), 4.18 (d, J=5.2 Hz, 2H), 3.96 (dd, J=8.8, 6.4 Hz, 1H), 3.65-3.60 (m, 1H), 3.30-3.25 (m, 2H), 3.16-2.98 (m, 14H), 2.80 (t, J=11.6 Hz, 2H), 2.65 (d, J=9.2 Hz, 2H). MS (ESI) m/z 576.2 $[M+H]^+$.

Step 2 Synthesis of N-(5-((5-chloro-4-(((3R,3aR, 6R, 6aR)-6-hydroxyhexahydrofurano[3,2-b]furan-3-yl) oxygen) pyrimidin-2-yl)amino)-2-(4-(4-methylpiperazin-1-yl) piperidin-1-yl)phenyl) acrylamide (LS 5-12)

Reduced iron powder (9 mg, 0.16 mmol) and ammonium chloride (3 mg, 0.055 mmol) were added to a mixed solvent of ethanol/water (2:1 by volume) of intermediate 17 (32 mg, 0.055 mmol), refluxed and reacted for 2 hours. After the reaction was complete, cooled to room temperature, filtered with a pad of Celite, spin-dried most of the solvent, extracted three times with dichloromethane. The organic phases were merged, washed with saturated salt water, dried over anhydrous sodium sulfate, spin-dried, and separated with column chromatography to obtain a gray solid 18.

Acrylic acid (13, 4.4 mg, 0.06 mmol), O-(7-azobenzotriazol-1-oxide)-N, N",N"-tetramethylurea hexafluorophosphate (HATU, 26 mg, 0.066 mmol), and N, N-diisopropylethylamine (DIPEA, 15 mg, 0.11 mmol) were added to 2 mL of DMF solution of intermediate 18 (30 mg, 0.055 mmol), and stirred to react overnight at room temperature. After the reaction was complete, most of the solvents was spin-dried under reduced pressure. The crude product was extracted three times with dichloromethane, the organic phases were combined, washed with saturated salt water, dried over anhydrous sodium sulfate, spin-dried, and separated by column chromatography to obtain a white solid.

$^1$H NMR (400 MHz, $CDCl_3$) δ 8.99 (s, 1H), 8.76 (s, 1H), 8.14 (s, 1H), 7.15-7.05 (m, 2H), 6.97 (d, J=7.2 Hz, 1H), 6.37 (dd, J=16.8, 1.6 Hz, 1H), 6.25 (dd, J=16.8, 10.0 Hz, 1H), 5.99 (q, J=5.6 Hz, 1H), 5.77 (dd, J=10.0, 1.2 Hz, 1H), 4.98 (t, J=5.2 Hz, 1H), 4.49 (t, J=5.6 Hz, 1H), 4.31-4.20 (m, 2H), 4.13 (dd, J=9.6, 5.2 Hz, 1H), 3.95 (dd, J=8.8, 6.4 Hz, 1H), 3.62 (dd, J=9.2, 8.0 Hz, 1H), 3.01 (d, J=12.0 Hz, 2H), 2.88-2.49 (m, 10H), 2.42-2.32 (m, 4H), 2.06 (d, J=12.4 Hz, 2H), 1.70-1.60 (m, 2H). $^{13}$C NMR (151 MHz, $CDCl_3$) δ 164.01 (s), 163.02 (s), 157.48 (s), 156.73 (s), 136.59 (s), 136.46 (s), 133.77 (s), 131.82 (s), 127.21 (s), 120.80 (s), 114.14 (s), 109.73 (s), 106.59 (s), 81.66 (s), 81.01 (s), 76.85 (s), 73.41 (s), 72.37 (s), 71.70 (s), 61.29 (s), 55.38 (s), 52.63

(d, J=13.3 Hz), 49.52 (s), 46.01 (s), 30.03 (s). HRMS (ESI) calcd for $C_{29}H_{39}ClN_7O_5$ $[M+H]^+$ 600.2696; found 600.2693.

Example 17

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-4-methoxy-2-(4-(4-methylpiperazin-1-yl) piperidin-1-yl)phenyl) acrylamide (LS 5-3)

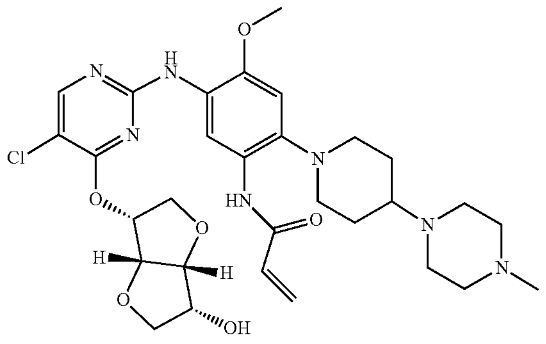 [SMILES: C=CC(=O)Nc1cc(Nc2ncc(Cl)c(O[C@@H]3CO[C@H]4[C@@H]3OC[C@H]4O)n2)c(OC)cc1N1CCC(N2CCN(C)CC2)CC1]

The synthesis method was the same as that of LS 5-12 in Example 16, except that 4-fluoro-2-methoxy-5-nitroaniline was used instead of 4-fluoro-3-nitroaniline (14) to participate in the reaction.

$^1H$ NMR (400 MHz, $CDCl_3$) δ 9.44 (s, 1H), 8.46 (s, 1H), 8.15 (s, 1H), 7.71 (s, 1H), 6.71 (s, 1H), 6.45-6.16 (m, 3H), 5.76 (dd, J=9.2, 2.4 Hz, 1H), 5.04 (t, J=5.6 Hz, 1H), 4.48 (t, J=5.2 Hz, 1H), 4.30 (dd, J=9.6, 6.0 Hz, 1H), 4.22 (s, 1H), 4.16 (dd, J=9.6, 4.8 Hz, 1H), 3.93 (dd, J=8.8, 6.4 Hz, 1H), 3.86 (s, 3H), 3.75-3.64 (m, 2H), 3.64-3.56 (m, 1H), 3.13-2.86 (m, 8H), 2.77-2.58 (m, 6H), 2.10-2.02 (m, 2H), 1.90-1.85 (m, 2H). $^{13}C$ NMR (151 MHz, $CDCl_3$) δ 164.18 (s), 162.60 (s), 157.24 (s), 156.61 (s), 144.22 (s), 135.76 (s), 131.77 (s), 126.78 (s), 126.40 (s), 125.78 (s), 109.53 (s), 106.21 (s), 103.14 (s), 81.73 (s), 81.23 (s), 72.94 (s), 72.26 (s), 71.84 (s), 61.32 (s), 56.05 (s), 55.04 (s), 52.48 (d, J=29.1 Hz), 49.12 (s), 45.74 (s), 29.67 (s). HRMS (ESI) calcd for $C_{30}H_{41}ClN_7O_6[M+H]^+$ 630.2801; found 630.2820.

Example 18

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-morpholinephenyl) acrylamide (LS 5-66)

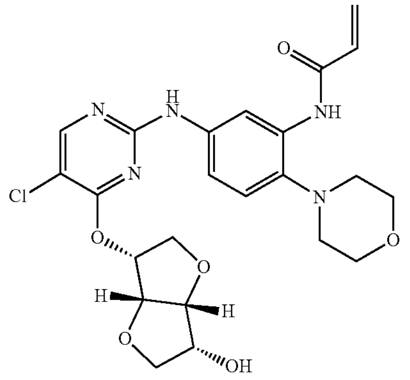 [SMILES: C=CC(=O)Nc1cc(Nc2ncc(Cl)c(O[C@@H]3CO[C@H]4[C@@H]3OC[C@H]4O)n2)ccc1N1CCOCC1]

The synthesis method was the same as that of LS 5-12 in Example 16, except that morpholine was used instead of 1-methyl-4-(piperidin-4-yl) piperazine hydrochloride (6) to participate in the reaction.

$^1H$ NMR (400 MHz, $CDCl_3$) δ 9.05 (s, 1H), 8.87 (s, 1H), 8.12 (s, 1H), 7.89 (s, 1H), 7.16 (d, J=8.8 Hz, 1H), 7.08-6.97 (m, 1H), 6.43-6.25 (m, 2H), 6.07 (q, J=5.2 Hz, 1H), 5.80 (dd, J=9.6, 1.6 Hz, 1H), 5.01 (t, J=5.6 Hz, 1H), 4.48 (t, J=5.2 Hz, 1H), 4.31-4.13 (m, 3H), 3.95 (dd, J=8.8, 6.4 Hz, 1H), 3.92-3.77 (m, 4H), 3.72 (q, J=6.8 Hz, 1H), 3.64-3.55 (m, 1H), 2.96-2.76 (m, 4H). $^{13}C$ NMR (151 MHz, $CDCl_3$) δ 164.03 (s), 162.98 (s), 157.42 (s), 156.74 (s), 137.08 (s), 135.50 (s), 133.91 (s), 131.76 (s), 127.33 (s), 121.31 (s), 114.28 (s), 109.72 (s), 106.74 (s), 81.66 (s), 81.02 (s), 76.85 (s), 73.40 (s), 72.36 (s), 71.71 (s), 67.73 (s), 52.88 (s). HRMS (ESI) calcd for $C_{23}H_{27}ClN_5O_6$ $[M+H]^+$ 504.1644; found 504.1637.

Example 19

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(2-hydroxyethyl) (methyl)amino)phenyl) acrylamide (LS 5-74)

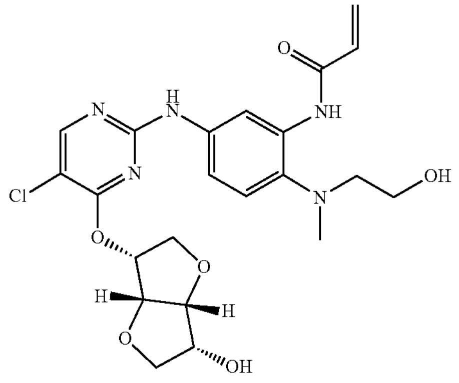 [SMILES: C=CC(=O)Nc1cc(Nc2ncc(Cl)c(O[C@@H]3CO[C@H]4[C@@H]3OC[C@H]4O)n2)ccc1N(C)CCO]

The synthesis method was the same as that of LS 5-12 in Example 16, except that 2-methylaminoethanol was used instead of 1-methyl-4-(piperidin-4-yl) piperazine hydrochloride (6) to participate in the reaction.

$^1$H NMR (400 MHz, $CDCl_3$) δ 8.84 (s, 1H), 8.09 (s, 1H), 7.21-6.99 (m, 2H), 6.52-6.27 (m, 2H), 5.88 (d, J=4.8 Hz, 1H), 5.75-5.64 (m, 1H), 4.92 (t, J=5.2 Hz, 1H), 4.42 (t, J=5.2 Hz, 1H), 4.28-4.13 (m, 2H), 4.09 (dd, J=9.6, 5.2 Hz, 1H), 3.90 (dd, J=8.8, 6.8 Hz, 1H), 3.68-3.56 (m, 3H), 3.35 (dt, J=3.2, 1.6 Hz, 1H), 2.93 (s, 2H), 2.80-2.70 (m, 3H). HRMS (ESI) calcd for $C_{22}H_{27}ClN_5O_6$ $[M+H]^+$ 492.1644; found 492.1649.

Example 20

Synthesis of (E)-N-(5-(5-chloro-4-(((3R,3aR,6R, 6aR)-6-hydroxyhexahydrofurano[3,2-b]furan-3-yl) oxygen) pyrimidin-2-yl)amino)-2-(4-(4-methylpiperazin-1-yl) piperidin-1-yl)phenyl)-2-butenamide (LS 5-72)

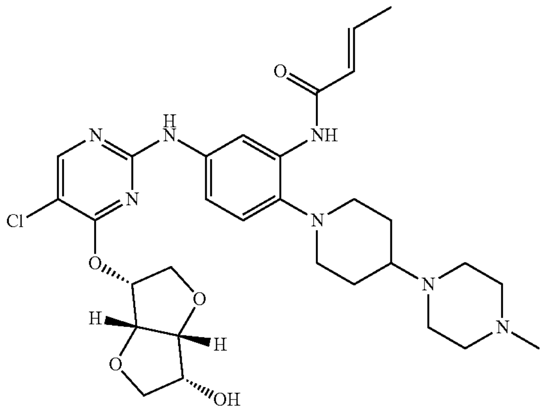 [SMILES: C/C=C/C(=O)Nc1cc(Nc2ncc(Cl)c(O[C@@H]3CO[C@H]4[C@@H]3OC[C@H]4O)n2)ccc1N1CCC(N2CCN(C)CC2)CC1]

The synthesis method was the same as that of LS 5-12 in Example 16, except that 2-butenoic acid was used instead of acrylic acid (13) to participate in the reaction.

$^1$H NMR (400 MHz, $CDCl_3$) δ 8.96 (s, 1H), 8.52 (s, 1H), 8.13 (s, 1H), 7.13-7.02 (m, 2H), 7.02-6.87 (m, 2H), 6.06-5.89 (m, 2H), 4.98 (t, J=5.6 Hz, 1H), 4.49 (t, J=5.2 Hz, 1H), 4.32-4.19 (m, 2H), 4.13 (dd, J=10.0, 5.2 Hz, 1H), 3.95 (dd, J=8.8, 6.4 Hz, 1H), 3.65-3.57 (m, 1H), 3.10-2.46 (m, 16H), 2.08 (d, J=10.0 Hz, 2H), 1.96 (dd, J=6.8, 1.6 Hz, 3H), 1.65-1.55 (m, 2H). $^{13}$C NMR (151 MHz, DMSO-$d_6$) δ 159.23 (s), 158.68 (s), 152.76 (s), 151.94 (s), 136.42 (s), 131.79 (s), 131.58 (s), 129.28 (s), 121.20 (s), 115.90 (s), 109.08 (s), 104.99 (s), 101.72 (s), 76.93 (s), 76.25 (s), 68.60 (s), 67.63 (s), 66.95 (s), 56.57 (s), 50.57 (s), 47.78 (d, J=14.0 Hz), 44.80 (s), 41.19 (s), 25.38 (s), 13.16 (s). HRMS (ESI) calcd for $C_{30}H_{41}ClN_7O_5[M+H]^+$ 614.2852; found 614.2855.

Example 21

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(4-(4-methylpiperazin-1-yl) piperidin-1-yl)phenyl) methylacrylamide (LS 5-73)

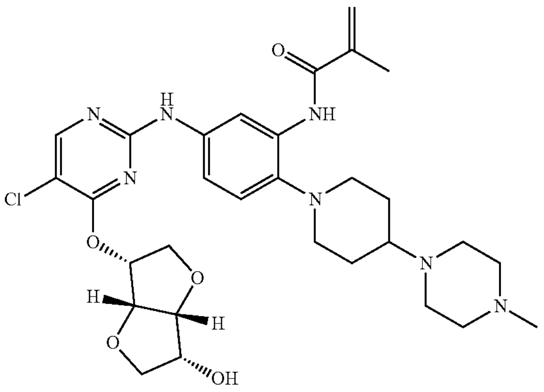 [SMILES: C=C(C)C(=O)Nc1cc(Nc2ncc(Cl)c(O[C@@H]3CO[C@H]4[C@@H]3OC[C@H]4O)n2)ccc1N1CCC(N2CCN(C)CC2)CC1]

The synthesis method was the same as that of LS 5-12 in Example 16, except that methacrylic acid was used instead of acrylic acid (13) to participate in the reaction.

$^1$H NMR (400 MHz, $CDCl_3$) δ 9.19 (s, 1H), 9.03 (s, 1H), 8.14 (s, 1H), 7.19-7.00 (m, 2H), 6.94 (d, J=8.0 Hz, 1H), 6.02 (q, J=5.2 Hz, 1H), 5.87 (s, 1H), 5.48 (s, 1H), 4.99 (t, J=5.6 Hz, 1H), 4.48 (t, J=5.2 Hz, 1H), 4.32-4.19 (m, 2H), 4.14 (dd, J=10.0, 5.2 Hz, 1H), 3.95 (dd, J=9.2, 6.4 Hz, 1H), 3.66-3.57 (m, 1H), 3.02 (d, J=12.0 Hz, 2H), 2.91-2.44 (m, 10H), 2.43-2.27 (m, 4H), 2.13-2.00 (m, 5H), 1.70-1.59 (m, 2H). $^{13}$C NMR (151 MHz, $CDCl_3$) δ 165.52 (s), 164.02 (s), 157.48 (s), 156.71 (s), 140.48 (s), 136.71 (s), 136.44 (s), 134.02 (s), 120.88 (s), 120.58 (s), 113.86 (s), 109.35 (s), 106.52 (s), 81.65 (s), 81.04 (s), 76.85 (s), 73.33 (s), 72.37 (s), 71.75 (s), 61.52 (s), 55.32 (s), 52.71 (d, J=15.8 Hz), 49.41 (s), 45.99 (s), 29.90 (s), 18.78 (s). HRMS (ESI) calcd for $C_{30}H_{41}ClN_7O_5[M+H]^+$ 614.2852; found 614.2856.

Example 22

Synthesis of (E)-N-(5-(5-chloro-4-(((3R,3aR,6R, 6aR)-6-hydroxyhexahydrofurano[3,2-b]furan-3-yl) oxygen) pyrimidin-2-yl)amino)-2-(4-(4-methylpiperazin-1-yl) piperidin-1-yl)phenyl)-4-(dimethylamino)-2-butenamide (LS 5-81)

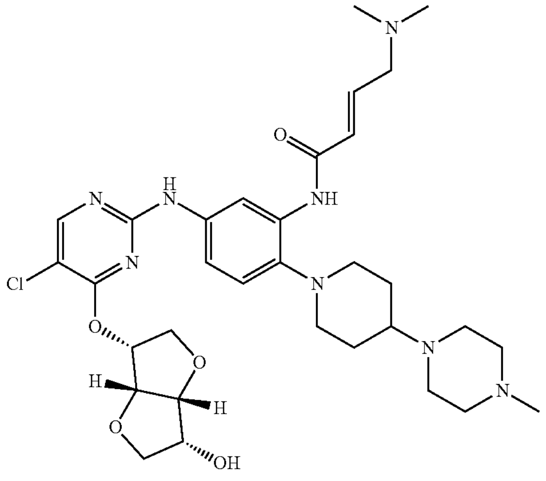 [SMILES: CN(C)C/C=C/C(=O)Nc1cc(Nc2ncc(Cl)c(O[C@@H]3CO[C@H]4[C@@H]3OC[C@H]4O)n2)ccc1N1CCC(N2CCN(C)CC2)CC1]

The synthesis method was the same as that of LS 5-12 in Example 16, except that 4-bromocrotonic acid was used instead of acrylic acid (13) to participate in the reaction, and the obtained intermediate 19 was substituted with 2M dimethylamine tetrahydrofuran solution to obtain the product.

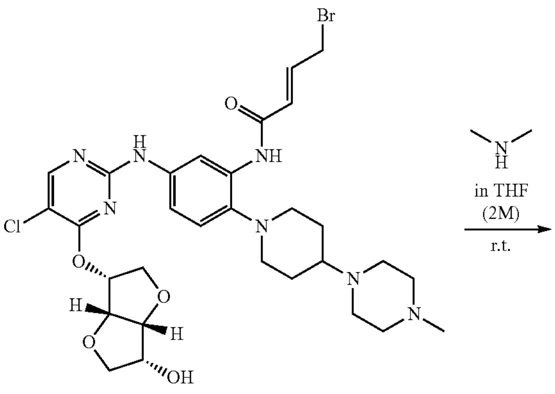

19

-continued

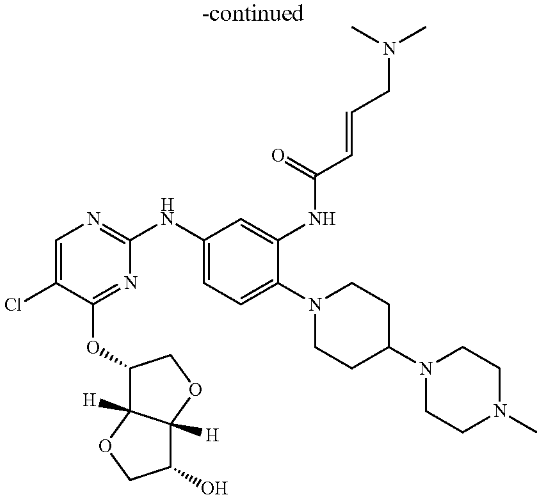

LS 5-81

Chemical compound LS 5-81: $^1$H NMR (400 MHz, $CDCl_3$) δ 8.99 (s, 1H), 8.69 (s, 1H), 8.13 (s, 1H), 7.15 (s, 1H), 7.08 (d, J=8.4 Hz, 1H), 7.06-6.84 (m, 2H), 6.15 (d, J=15.2 Hz, 1H), 5.98 (q, J=5.6 Hz, 1H), 4.97 (t, J=5.2 Hz, 1H), 4.48 (t, J=5.2 Hz, 1H), 4.33-4.19 (m, 2H), 4.11 (dd, J=10.0, 5.4 Hz, 1H), 3.95 (dd, J=8.8, 6.4 Hz, 1H), 3.68-3.57 (m, 1H), 3.20 (d, J=6.0 Hz, 2H), 3.01 (d, J=11.6 Hz, 2H), 2.94-2.63 (m, 9H), 2.47-2.39 (m, 5H), 2.34 (s, 6H), 2.08 (d, J=12.0 Hz, 2H), 1.80-1.68 (m, 2H). HRMS (ESI) calcd for $C_{32}H_{46}ClN_8O_5[M+H]^+$ 657.3274; found 657.3296.

Example 23

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(2-(dimethylamino) ethyl)(methyl)amino)phenyl) acrylamide (LS 5-88)

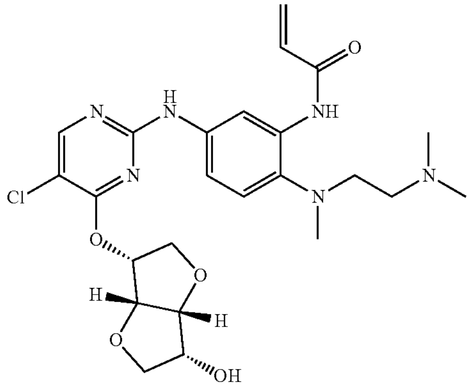 [SMILES: C=CC(=O)Nc1cc(Nc2ncc(Cl)c(O[C@@H]3CO[C@H]4[C@@H]3OC[C@H]4O)n2)ccc1N(C)CCN(C)C]

The synthesis method was the same as that of LS 5-12 in Example 16, except that N, N, N'-trimethylethylenediamine was used instead of 1-methyl-4-(piperidin-4-yl) piperazine hydrochloride (6) to participate in the reaction.

$^1$H NMR (400 MHz, $CDCl_3$) δ 10.11 (s, 1H), 9.03 (s, 1H), 8.14 (s, 1H), 7.14 (d, J=8.0 Hz, 2H), 7.01 (d, J=8.4 Hz, 1H), 6.56-6.27 (m, 2H), 6.02 (d, J=5.4 Hz, 1H), 5.72 (d, J=11.7 Hz, 1H), 4.99 (t, J=5.2 Hz, 1H), 4.50 (t, J=5.2 Hz, 1H), 4.35-4.19 (m, 2H), 4.14 (dd, J=9.6, 5.1 Hz, 1H), 4.00-3.88

(m, 1H), 3.69-3.57 (m, 1H), 2.92 (s, 2H), 2.69 (s, 3H), 2.55-2.15 (m, 7H), 2.05-1.94 (m, 1H). $^{13}C$ NMR (151 MHz, $CDCl_3$) δ 164.02 (s), 163.66 (s), 157.52 (s), 156.71 (s), 136.70 (d, J=14.1 Hz), 136.10 (s), 132.00 (s), 129.89 (s), 126.72 (s), 122.51 (s), 114.27 (s), 110.31 (s), 106.53 (s), 81.65 (s), 81.03 (s), 76.85 (s), 73.43 (s), 72.37 (s), 71.71 (s), 57.24 (s), 45.41 (s), 43.32 (s), 29.33 (s). HRMS (ESI) calcd for $C_{24}H_{32}ClN_6O_5[M+H]^+$ 519.2117; found 519.2106.

Example 24

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(9-methyl-3,9-diazospira[5.5]undecano-3-yl) phenyl) acrylamide (LS 5-91)

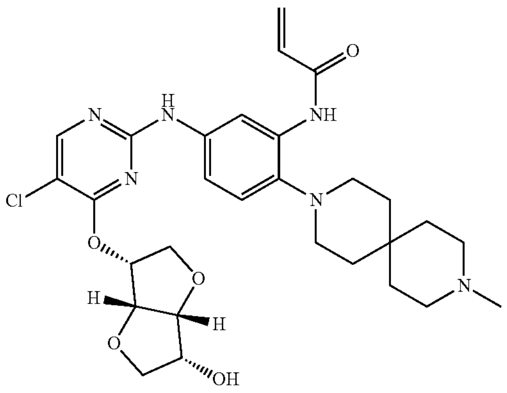 [SMILES: C=CC(=O)Nc1cc(Nc2ncc(Cl)c(O[C@@H]3CO[C@H]4[C@@H]3OC[C@H]4O)n2)ccc1N1CCC2(CCN(C)CC2)CC1]

The synthesis method was the same as that of LS 5-12 in Example 16, except that 3-methyl-3,9-diazospira[5,5]undecane was used instead of 1-methyl-4-(piperidin-4-yl) piperazine hydrochloride (6) to participate in the reaction.

$^{1}H$ NMR (400 MHz, $CDCl_3$) δ 8.98 (s, 1H), 8.83 (s, 1H), 8.14 (s, 1H), 7.17-7.06 (m, 2H), 7.02-6.91 (m, 1H), 6.37 (dd, J=16.8, 1.6 Hz, 1H), 6.27 (dd, J=16.8, 10.0 Hz, 1H), 5.99 (d, J=5.6 Hz, 1H), 5.77 (dd, J=10.0, 1.6 Hz, 1H), 4.99 (t, J=5.2 Hz, 1H), 4.49 (t, J=5.2 Hz, 1H), 4.30-4.20 (m, 2H), 4.13 (dd, J=10.0, 5.2 Hz, 1H), 3.95 (dd, J=9.2, 6.4 Hz, 1H), 3.62 (t, J=8.4 Hz, 1H), 2.88-2.67 (m, 4H), 2.44 (s, 4H), 2.32 (s, 3H), 1.95-1.65 (m, 8H). $^{13}C$ NMR (151 MHz, $CDCl_3$) δ 164.00 (s), 162.98 (s), 157.51 (s), 156.73 (s), 136.94 (s), 136.46 (s), 133.71 (s), 131.92 (s), 127.06 (s), 120.84 (s), 114.19 (s), 109.75 (s), 106.52 (s), 81.67 (s), 81.01 (s), 76.85 (s), 73.38 (s), 72.38 (s), 71.69 (s), 53.44 (s), 51.19 (s), 48.64 (s), 46.41 (s), 28.58 (s). HRMS (ESI) calcd for $C_{29}H_{38}ClN_6O_5[M+H]^+$ 585.2587; found 585.2582.

Example 25

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(4-(dimethylamino) piperidin-1-yl)phenyl) acrylamide (LS 5-102)

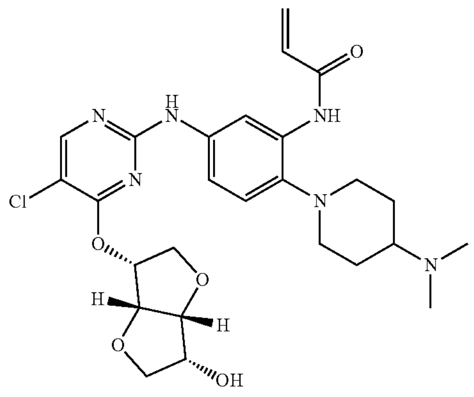 [SMILES: C=CC(=O)Nc1cc(Nc2ncc(Cl)c(O[C@@H]3CO[C@H]4[C@@H]3OC[C@H]4O)n2)ccc1N1CCC(N(C)C)CC1]

The synthesis method was the same as that of LS 5-12 in Example 16, except that 4-(dimethylamino) piperidine was used instead of 1-methyl-4-(piperidin-4-yl) piperazine hydrochloride (6) to participate in the reaction.

$^{1}H$ NMR (400 MHz, $CDCl_3$) δ 8.87 (s, 1H), 8.09 (s, 1H), 7.10-6.95 (m, 2H), 6.39-6.26 (m, 2H), 5.92 (d, J=4.8 Hz, 1H), 5.76 (dd, J=7.3, 4.1 Hz, 1H), 4.94 (t, J=5.2 Hz, 1H), 4.44 (t, J=5.2 Hz, 1H), 4.26-4.15 (m, 2H), 4.10 (dd, J=10.0, 5.2 Hz, 1H), 3.91 (dd, J=8.8, 6.8 Hz, 1H), 3.59 (t, J=8.4 Hz, 1H), 3.01 (d, J=12.0 Hz, 2H), 2.76-2.63 (m, 2H), 2.56-2.43 (m, 7H), 2.07 (d, J=12.4 Hz, 2H), 1.80-1.66 (m, 2H). $^{13}C$ NMR (151 MHz, $CDCl_3$) δ 164.02 (s), 163.05 (s), 157.46 (s), 156.72 (s), 136.65 (s), 136.34 (s), 133.80 (s), 131.86 (s), 127.17 (s), 120.84 (s), 114.13 (s), 109.74 (s), 106.62 (s), 81.66 (s), 81.01 (s), 76.85 (s), 73.42 (s), 72.36 (s), 71.70 (s), 61.92 (s), 52.40 (d, J=12.6 Hz), 41.96 (s), 30.00 (s). HRMS (ESI) calcd for $C_{26}H_{34}ClN_6O_5[M+H]^+$ 545.2274; found 545.2257.

Example 26

Synthesis of N-(5-((5-chloropyrimidin-2-yl)amino)-2-(4-(4-methylpiperazin-1-yl) piperidin-1-yl)phenyl) acrylamide (LS 5-126)

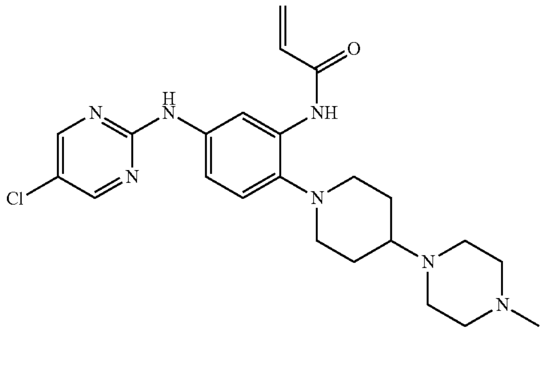 [SMILES: C=CC(=O)Nc1cc(Nc2ncc(Cl)cn2)ccc1N1CCC(N2CCN(C)CC2)CC1]

The synthesis method was the same as that of LS 5-12 in Example 16, except that 2,5-dichloropyrimidine was used instead of 2,4,5-trichloropyrimidine to participate in the reaction.

$^1H$ NMR (400 MHz, $CDCl_3$) δ 8.72 (s, 1H), 8.54 (s, 1H), 8.35 (s, 2H), 7.48 (dd, J=8.8, 2.5 Hz, 1H), 7.20-7.10 (m, 2H), 6.40 (d, J=16.4 Hz, 1H), 6.26 (dd, J=16.8, 10.0 Hz, 1H), 5.78 (d, J=10.4 Hz, 1H), 3.02 (d, J=12.0 Hz, 2H), 2.92-2.30 (m, 14H), 2.07 (d, J=12.4 Hz, 2H), 1.67 (d, J=10.8 Hz, 2H). HRMS (ESI) calcd for $C_{23}H_{31}ClN_7O$ $[M+H]^+$ 456.2273; found 456.2274.

Example 27

Synthesis of N-(5-((4-(((3R,3aR,6R, 6aR)-6-hydroxyhexahydrofurano[3,2-b]furan-3-yl) oxygen)-5-methylpyrimidin-2-yl)amino)-2-(4-(4-methylpiperazin-1-yl) piperidin-1-yl)phenyl) acrylamide (LS 5-133)

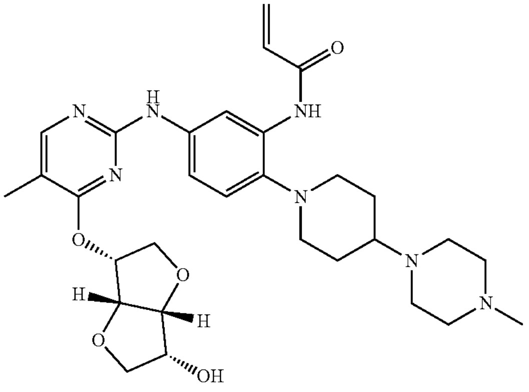

The synthesis method was the same as that of LS 5-12 in Example 16, except that 5-methyl-2,4-dichloropyrimidine was used instead of 2,4,5-trichloropyrimidine to participate in the reaction.

$^1H$ NMR (400 MHz, $CDCl_3$) δ 8.97 (s, 1H), 8.78 (s, 1H), 7.96 (s, 1H), 7.18 (s, 1H), 7.07 (d, J=8.6 Hz, 1H), 7.04-6.95 (m, 1H), 6.36 (d, J=16.8 Hz, 1H), 6.24 (dd, J=16.8, 10.0 Hz, 1H), 5.91 (q, J=6.4 Hz, 1H), 5.75 (d, J=11.2 Hz, 1H), 4.95 (t, J=5.1 Hz, 1H), 4.51 (t, J=5.1 Hz, 1H), 4.33-4.22 (m, 2H), 4.04-3.88 (m, 2H), 3.62-3.54 (m, 1H), 2.98 (d, J=11.6 Hz, 2H), 2.75-2.29 (m, 14H), 2.05-2.00 (m, 5H), 1.63 (d, J=8.8 Hz, 2H). HRMS (ESI) calcd for $C_{30}H_{42}N_7O_5$ $[M+H]^+$ 580.3242; found 580.3250.

Example 28

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(4-ethylpiperazin-1-yl)phenyl) acrylamide (LS 5-143)

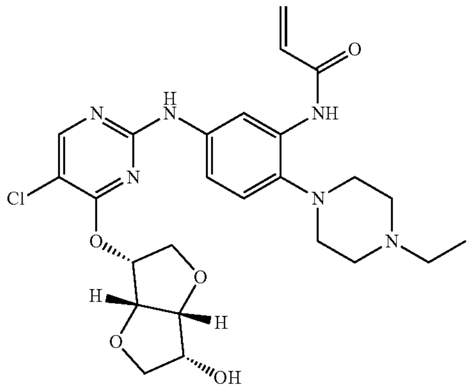 [SMILES: C=CC(=O)Nc1cc(Nc2ncc(Cl)c(O[C@@H]3CO[C@H]4[C@@H]3OC[C@H]4O)n2)ccc1N1CCN(CC)CC1]

The synthesis method was the same as that of LS 5-12 in Example 16, except that N-ethylpiperazine was used instead of 1-methyl-4-(piperidin-4-yl) piperazine hydrochloride (6) to participate in the reaction.

$^1H$ NMR (400 MHz, $CDCl_3$) δ 8.98 (s, 1H), 8.76 (s, 1H), 8.15 (s, 1H), 7.19 (d, J=8.4 Hz, 1H), 7.10-6.94 (m, 2H), 6.43-6.33 (m, 1H), 6.27 (dd, J=16.9, 10.0 Hz, 1H), 5.98 (d, J=6.0 Hz, 1H), 5.79 (dd, J=10.0, 1.2 Hz, 1H), 4.99 (t, J=5.3 Hz, 1H), 4.50 (t, J=5.3 Hz, 1H), 4.32-4.18 (m, 2H), 4.14 (dd, J=9.8, 5.2 Hz, 1H), 3.96 (dd, J=9.0, 6.5 Hz, 1H), 3.65-3.58 (m, 1H), 3.19-2.45 (m, 10H), 1.55-1.44 (m, 3H). $^{13}C$ NMR (151 MHz, $CDCl_3$) δ 164.01 (s), 162.96 (s), 157.47 (s), 156.70 (s), 136.82 (s), 135.87 (s), 133.87 (s), 131.89 (s), 127.11 (s), 121.25 (s), 114.27 (s), 109.64 (s), 106.58 (s), 81.68 (s), 81.01 (s), 76.85 (s), 73.38 (s), 72.38 (s), 71.69 (s), 53.76 (s), 52.49 (s), 52.42 (s), 12.06 (s). HRMS (ESI) calcd for $C_{25}H_{32}ClN_6O_5[M+H]^+$ 531.2117; found 531.2126.

Example 29

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-(3-(dimethylamino) pyrrol-1-yl)phenyl) acrylamide (LS 5-150)

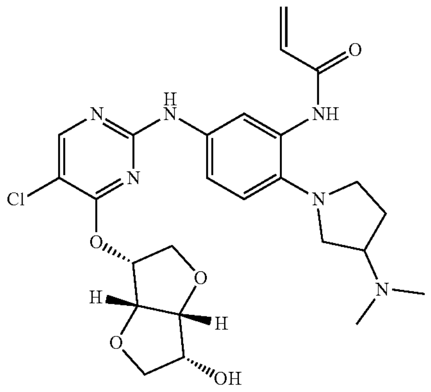 [SMILES: C=CC(=O)Nc1cc(Nc2ncc(Cl)c(O[C@@H]3CO[C@H]4[C@@H]3OC[C@H]4O)n2)ccc1N1CCC(N(C)C)C1]

The synthesis method was the same as that of LS 5-12 in Example 16, except that 3-(dimethylamino) pyrrole was used instead of 1-methyl-4-(piperidin-4-yl) piperazine hydrochloride (6) to participate in the reaction.

$^{1}H$ NMR (400 MHz, $CDCl_3$) δ 8.92 (s, 1H), 8.73 (s, 1H), 8.14 (s, 1H), 7.11 (d, J=8.2 Hz, 1H), 7.02-6.94 (m, 2H), 6.58-6.27 (m, 2H), 5.97 (d, J=6.0 Hz, 1H), 5.76 (d, J=11.6 Hz, 1H), 5.01-4.93 (m, 1H), 4.52-4.45 (m, 1H), 4.26 (dd, J=9.8, 6.0 Hz, 2H), 4.14 (dd, J=9.8, 5.2 Hz, 1H), 3.95 (dd, J=9.2, 6.4 Hz, 1H), 3.65-3.58 (m, 1H), 3.24-2.95 (m, 5H), 2.53-2.24 (m, 6H), 2.20 (s, 1H), 2.07 (s, 1H). $^{13}C$ NMR (151 MHz, $CDCl_3$) δ 164.00 (s), 163.15 (s), 157.53 (s), 156.70 (s), 136.18 (s), 134.15 (s), 134.04 (d, J=7.7 Hz), 131.76 (s), 127.26 (s), 120.52 (d, J=4.9 Hz), 114.67 (s), 110.56 (s), 106.44 (s), 81.68 (d, J=3.0 Hz), 81.02 (s), 73.33 (d, J=2.6 Hz), 72.38 (s), 71.71 (d, J=4.2 Hz), 65.77 (s), 57.33 (s), 52.48 (d, J=4.4 Hz), 44.02 (s), 30.14 (s). HRMS (ESI) calcd for $C_{25}H_{32}ClN_6O_5[M+H]^+$ 531.2117; found 531.2111.

Example 30

Synthesis of N-(2-(((1S,4S)-2-oxa-5-azabicyclic [2.2.1]heptane-5-yl)-5-(5-chloro-4-(((3R,3aR,6R, 6aR)-6-hydroxyhexahydrofurano[3,2-b]furan-3-yl) oxygen) pyrimidin-2-yl)amino)phenyl) acrylamide (LS 5-152)

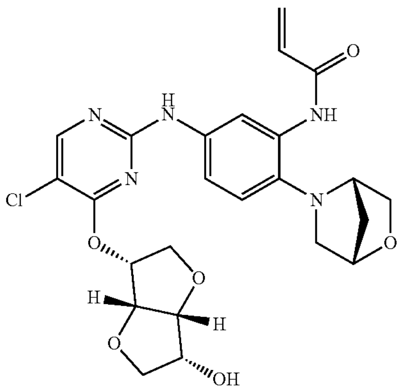 [SMILES: C=CC(=O)Nc1cc(Nc2ncc(Cl)c(O[C@@H]3CO[C@H]4[C@@H]3OC[C@H]4O)n2)ccc1N1C[C@@H]2C[C@H]1CO2]

The synthesis method was the same as that of LS 5-12 in Example 16, except that (1S,4S)-2-oxo-5-azabicyclic[2.2.1] heptane was used instead of 1-methyl-4-(piperidin-4-yl) piperazine hydrochloride (6) to participate in the reaction.

$^{1}H$ NMR (400 MHz, $CDCl_3$) δ 8.82 (s, 2H), 8.14 (s, 1H), 7.51 (s, 1H), 7.23-6.96 (m, 2H), 6.54-6.29 (m, 2H), 5.94 (d, J=4.0 Hz, 1H), 5.80 (d, J=11.2 Hz, 1H), 5.00 (t, J=5.3 Hz, 1H), 4.71-4.59 (m, 1H), 4.51 (t, J=5.2 Hz, 1H), 4.37-4.11 (m, 3H), 4.11-3.99 (m, 1H), 3.98-3.82 (m, 2H), 3.81-3.69 (m, 1H), 3.67-3.45 (m, 2H), 3.28 (s, 1H), 2.63 (d, J=7.2 Hz, 1H), 2.27-2.13 (m, 1H), 2.10-1.99 (m, 1H). $^{13}C$ NMR (151 MHz, $CDCl_3$) δ 164.01 (s), 162.97 (s), 157.50 (s), 156.75 (s), 135.85 (s), 133.97 (s), 133.68 (s), 131.71 (s), 127.42 (s), 121.42 (s), 114.47 (s), 111.01 (s), 106.56 (s), 81.66 (s), 81.03 (s), 73.41 (s), 72.36 (s), 72.28 (s), 71.71 (s), 62.09 (s), 59.74 (s), 36.42 (s). HRMS (ESI) calcd for $C_{24}H_{27}ClNO_6$ $[M+H]^+$ 516.1644; found 516.1640.

Example 31

Synthesis of N-(5-(5-chloro-4-(((3R,3aR,6R, 6aR)-6-hydroxyhexahydrofurano[3,2-b]furan-3-yl) oxygen) pyrimidin-2-yl)amino)-2-((1R,4R)-5-methyl-2, 5-diazabicyclic[2.2.1]heptane-2-yl)phenyl) acrylamide (LS 5-154)

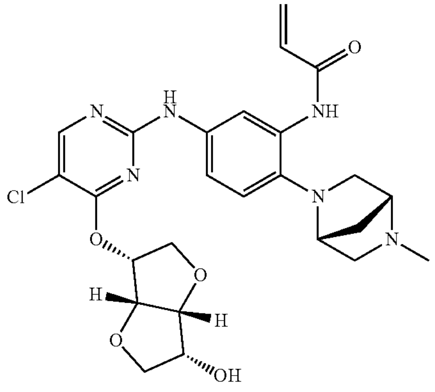 [SMILES: C=CC(=O)Nc1cc(Nc2ncc(Cl)c(O[C@@H]3CO[C@H]4[C@@H]3OC[C@H]4O)n2)ccc1N1C[C@H]2C[C@@H]1CN2C]

The synthesis method was the same as that of LS 5-12 in Example 16, except that 2-methyl-2,5-diazabicyclic[2.2.1] heptane was used instead of 1-methyl-4-(piperidin-4-yl) piperazine hydrochloride (6) to participate in the reaction.

$^{1}H$ NMR (400 MHz, $CDCl_3$) δ 8.93 (s, 1H), 8.52 (s, 1H), 8.13 (s, 1H), 7.17-7.04 (m, 2H), 6.99 (d, J=6.4 Hz, 1H), 6.69-6.54 (m, 1H), 6.40 (dd, J=16.8, 1.4 Hz, 1H), 5.97 (d, J=5.2 Hz, 1H), 5.78 (dd, J=10.2, 1.4 Hz, 1H), 4.96 (t, J=5.3 Hz, 1H), 4.48 (t, J=5.3 Hz, 1H), 4.25 (dd, J=9.8, 5.9 Hz, 2H), 4.14 (dd, J=9.9, 5.1 Hz, 1H), 4.07-3.91 (m, 2H), 3.79 (d, J=17.2 Hz, 2H), 3.67-3.57 (m, 1H), 2.96 (d, J=10.3 Hz, 1H), 2.82-2.56 (m, 5H), 2.15-2.06 (s, 2H). $^{13}C$ NMR (151 MHz, $CDCl_3$) δ 163.99 (s), 162.97 (s), 157.54 (s), 156.75 (s), 135.47 (s), 134.96 (s), 133.84 (s), 131.78 (s), 127.29 (s), 121.19 (s), 114.46 (s), 110.90 (s), 106.43 (s), 81.64 (s), 81.02 (s), 73.37 (s), 72.36 (s), 71.73 (s), 63.91 (s), 63.34 (s), 60.85 (s), 56.21 (s), 42.15 (s), 33.96 (s). HRMS (ESI) calcd for $C_{25}H_{30}ClN_6O_5[M+H]^+$ 529.1961; found 529.1965.

Example 32

Synthesis of N-(5-(5-chloro-4-(((3R,3aR,6R, 6aR)-6-methoxyhexahydrofurano[3,2-b]furan-3-yl)oxy) pyrimidin-2-yl)amino)-2-(4-(4-methylpiperazin-1-yl) piperidin-1-yl)phenyl) acrylamide (LS 6-16)

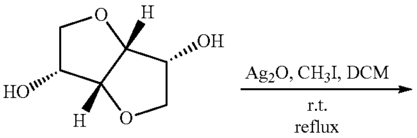

8

-continued

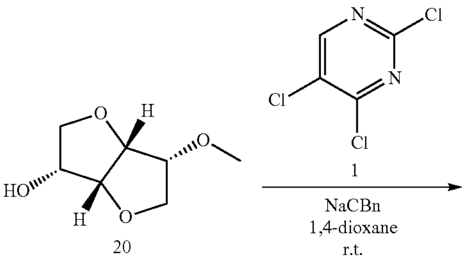

20

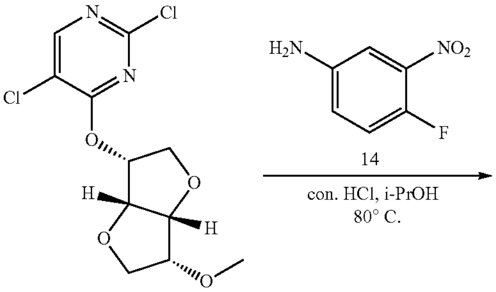

21

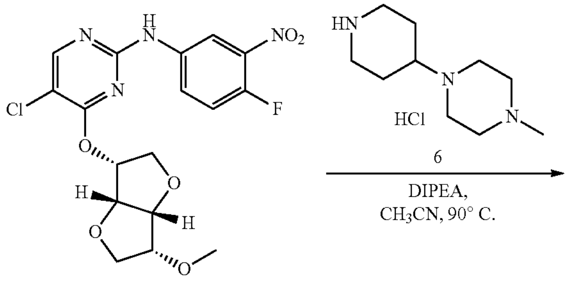

22

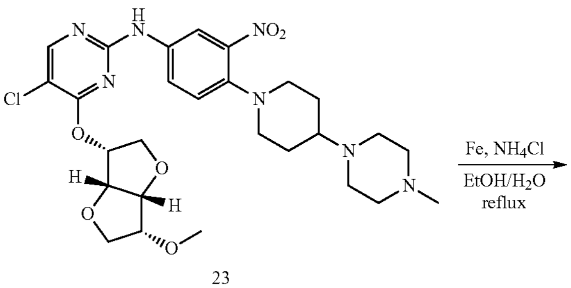

23

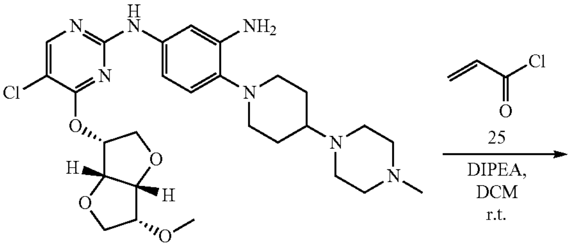

24

-continued

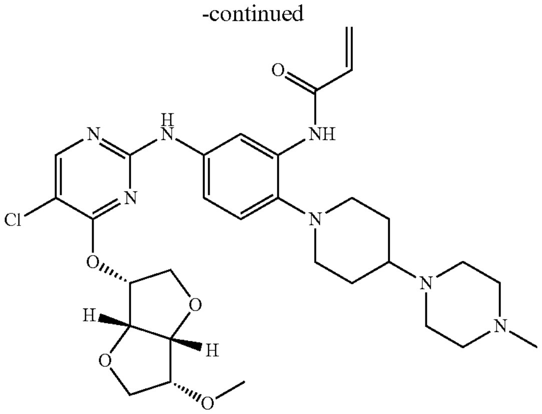

LS 6-16

Step 1 Synthesis of (3R,3aR,6R, 6aR)-6-methoxy-hexahydrofuran[3,2-b]furan-3-ol (20)

1,4:3,6-didehydrated mannitol (8, 1.0 g, 6.84 mmol) was dissolved in 30 mL of dichloromethane, added silver oxide (2.37 g, 10.2 mmol) to the system, stirred in the dark for 10 minutes, and reacted overnight in the dark after adding iodomethane (0.43 mL, 6.84 mmol) dropwise. The next day, after the reaction was complete, filtered with a pad of Celite, extracted three times with dichloromethane, the organic phases were combined, washed with saturated salt water, dried over anhydrous sodium sulfate, spin-dried, and separated by column chromatography to obtain a compound 20 (0.8 g, 77%). $^1H$ NMR (400 MHz, $CDCl_3$) δ 4.57 (t, J=4.8 Hz, 1H), 4.52 (t, J=5.2 Hz, 1H), 4.28 (q, J=6.0 Hz, 1H), 4.08 (dd, J=8.6, 6.4 Hz, 1H), 4.02-3.91 (m, 2H), 3.76-3.62 (m, 2H), 3.47 (d, J=7.7 Hz, 3H). MS (ESI) m/z 162.1 $[M+H]^+$.

Step 2 Synthesis of 2,5-Dichloro-4-(((3R,3aR,6R, 6aR)-6-methoxyhexahydrofuran [3,2-b]furan-3-yl) oxy) pyrimidine (21)

Intermediate 20 (0.2 g, 1.25 mmol) was dissolved in 5 mL of 1,4-dioxane solvent, added sodium tert butanol (0.14 g, 1.38 mmol) to the system, stirred at room temperature for 10 minutes, and then added raw material 1 dropwise (143 μL, 1.25 mmol) to the system, reacted at room temperature and stirred overnight. After the reaction was complete, spin-dried most of the solvents under reduced pressure. The crude product was extracted three times with dichloromethane, the organic phases were combined, washed with saturated salt water, dried over anhydrous sodium sulfate, spin-dried, and separated by column chromatography to obtain a compound 21 (0.29 g, 80%). $^1H$ NMR (400 MHz, $CDCl_3$) δ 8.34 (s, 1H), 5.56 (dd, J=10.2, 5.7 Hz, 1H), 4.96 (t, J=5.4 Hz, 1H), 4.57 (t, J=4.9 Hz, 1H), 4.21 (dd, J=10.4, 4.4 Hz, 1H), 4.09 (dd, J=10.4, 5.7 Hz, 1H), 4.01-3.95 (m, 1H), 3.95-3.87 (m, 1H), 3.67 (t, J=8.4 Hz, 1H), 3.50 (s, 3H). MS (ESI) m/z 307.0 $[M+H]^+$.

The method for the subsequent synthesis steps was the same as that of LS 5-12 in Example 16, except that the reaction raw materials were substituted to participate in the reaction.

Compound 22: $^1H$ NMR (400 MHz, $CDCl_3$) δ 8.81 (dd, J=6.4, 2.7 Hz, 1H), 8.19 (s, 1H), 7.82 (s, 1H), 7.50-7.41 (m, 1H), 7.30-7.20 (m, 1H), 5.59 (dd, J=9.5, 5.6 Hz, 1H), 5.02 (t, J=5.4 Hz, 1H), 4.61 (t, J=4.9 Hz, 1H), 4.29 (dd, J=10.5, 3.7 Hz, 1H), 4.09 (dd, J=10.6, 5.4 Hz, 1H), 4.02-3.95 (m, 1H), 3.95-3.87 (m, 1H), 3.75-3.66 (m, 1H), 3.50 (s, 3H). MS (ESI) m/z 427.1 $[M+H]^+$.

Compound 23: $^1$H NMR (400 MHz, $CDCl_3$) δ 8.47 (d, J=2.4 Hz, 1H), 8.14 (s, 1H), 7.29 (dd, J=8.8, 2.5 Hz, 1H), 7.23 (s, 1H), 7.11 (d, J=8.8 Hz, 1H), 5.54 (dd, J=10.1, 5.6 Hz, 1H), 4.99 (t, J=5.4 Hz, 1H), 4.61 (t, J=4.9 Hz, 1H), 4.22 (dd, J=10.3, 4.3 Hz, 1H), 4.09 (dd, J=10.3, 5.6 Hz, 1H), 4.02-3.95 (m, 1H), 3.95-3.86 (m, 1H), 3.74-3.67 (m, 1H), 3.49 (s, 3H), 3.33-3.22 (m, 2H), 2.72-2.25 (m, 14H), 1.91 (d, J=11.6 Hz, 2H), 1.78-1.69 (m, 2H). MS (ESI) m/z 591.2 $[M+H]^+$.

Compound 24: $^1$H NMR (400 MHz, $CDCl_3$) δ 8.11 (s, 1H), 6.96 (d, J=2.4 Hz, 1H), 6.91 (d, J=8.4 Hz, 1H), 6.85-6.75 (m, 2H), 5.44 (q, J=5.6 Hz, 1H), 4.90 (t, J=5.3 Hz, 1H), 4.58 (t, J=4.9 Hz, 1H), 4.13 (dd, J=5.6, 1.5 Hz, 2H), 4.06-3.95 (m, 3H), 3.95-3.90 (m, 1H), 3.72 (t, J=8.7 Hz, 1H), 3.50 (s, 3H), 3.17 (d, J=12.0 Hz, 2H), 2.85-2.43 (m, 14H), 2.01 (d, J=12.0 Hz, 2H), 1.72 (d, J=10.8 Hz, 2H). MS (ESI) m/z 561.3 $[M+H]^+$.

Compound LS 6-16: $^1$H NMR (400 MHz, $CDCl_3$) δ 8.92 (s, 1H), 8.75 (s, 1H), 8.11 (s, 1H), 7.22 (s, 1H), 7.08 (d, J=8.8 Hz, 1H), 7.01 (d, J=8.4 Hz, 1H), 6.36 (dd, J=16.9, 1.2 Hz, 1H), 6.25 (dd, J=16.9, 10.0 Hz, 1H), 5.90 (q, J=5.2 Hz, 1H), 5.76 (dd, J=10.0, 1.2 Hz, 1H), 5.00 (t, J=5.3 Hz, 1H), 4.53 (t, J=4.8 Hz, 1H), 4.22-4.09 (m, 2H), 4.04-3.93 (m, 1H), 3.92-3.82 (m, 1H), 3.75-3.67 (m, 1H), 3.47 (s, 3H), 2.99 (d, J=12.0 Hz, 2H), 2.80-2.26 (m, 14H), 2.06 (d, J=11.6 Hz, 2H), 1.69-1.61 (m, 2H). MS (ESI) m/z 614.3 $[M+H]^+$.

Example 33

Synthesis of N-(5-(5-chloro-4-(((3R,3aR,6R, 6aR)-6-methoxyhexahydrofurano[3,2-b]furan-3-yl)oxy) pyrimidin-2-yl)amino)-2-(2-(dimethylamino)ethyl) (methyl)amino)phenyl) acrylamide (LS 6-45)

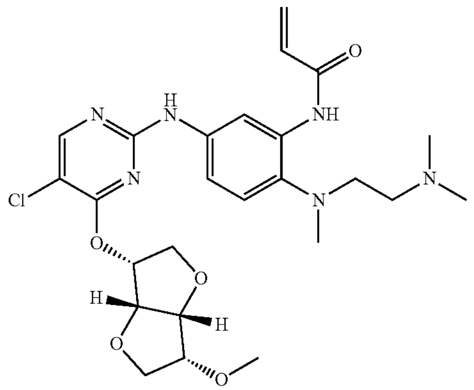 [SMILES: C=CC(=O)Nc1cc(Nc2ncc(Cl)c(O[C@@H]3CO[C@H]4[C@@H]3OC[C@H]4OC)n2)ccc1N(C)CCN(C)C]

The synthesis method was the same as that of LS 6-16 in Example 32, except that N, N, N'-trimethylethylenediamine was used instead of 1-methyl-4-(piperidin-4-yl) piperazine hydrochloride (6) to participate in the reaction.

$^1$H NMR (400 MHz, $CDCl_3$) δ 10.19 (s, 1H), 8.97 (s, 1H), 8.13 (s, 1H), 7.22-6.96 (m, 3H), 6.50-6.25 (m, 2H), 5.93 (d, J=5.6 Hz, 1H), 5.78-5.62 (m, 1H), 5.02 (t, J=5.3 Hz, 1H), 4.55 (t, J=4.8 Hz, 1H), 4.28-4.13 (m, 2H), 3.99 (t, J=7.2 Hz, 1H), 3.94-3.85 (m, 1H), 3.72 (t, J=8.4 Hz, 1H), 3.48 (s, 3H), 2.87 (t, J=4.8 Hz, 2H), 2.68 (s, 3H), 2.52-2.06 (m, 8H). $^{13}$C NMR (151 MHz, $CDCl_3$) δ 164.21 (s), 163.57 (s), 157.53 (s), 156.59 (s), 136.80 (s), 136.64 (s), 136.16 (s), 132.04 (s), 126.58 (s), 122.57 (s), 114.25 (s), 110.29 (s), 106.64 (s), 81.46 (s), 80.04 (s), 76.94 (s), 71.93 (s), 69.89 (s), 58.37 (s), 57.38 (s), 56.62 (s), 45.55 (s), 43.30 (s). HRMS (ESI) calcd for $C_{25}H_{34}ClN_6O_5[M+H]^+$ 533.2274; found 533.2251.

Example 34

Synthesis of N-(5-(5-chloro-4-(((3R,3aR,6R, 6aR)-6-methoxyhexahydrofurano[3,2-b]furan-3-yl)oxy) pyrimidin-2-yl)amino)-2-morpholinephenyl) acrylamide (LS 6-48)

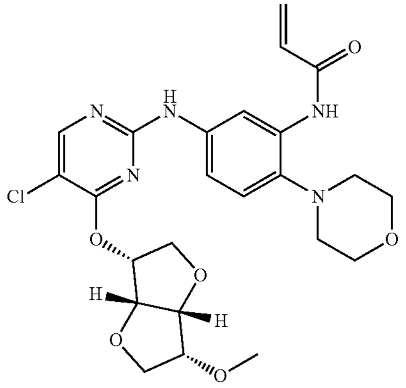 [SMILES: C=CC(=O)Nc1cc(Nc2ncc(Cl)c(O[C@@H]3CO[C@H]4[C@@H]3OC[C@H]4OC)n2)ccc1N1CCOCC1]

The synthesis method was the same as that of LS 6-16 in Example 32, except that morpholine was used instead of 1-methyl-4-(piperidin-4-yl) piperazine hydrochloride (6) to participate in the reaction.

$^1$H NMR (400 MHz, $CDCl_3$) δ 8.96 (s, 1H), 8.83 (s, 1H), 8.13 (s, 1H), 7.38 (s, 1H), 7.14 (d, J=8.4 Hz, 1H), 7.07 (d, J=8.0 Hz, 1H), 6.38 (dd, J=16.8, 1.6 Hz, 1H), 6.28 (dd, J=16.9, 10.0 Hz, 1H), 5.93 (q, J=5.0 Hz, 1H), 5.79 (dd, J=10.0, 1.4 Hz, 1H), 5.01 (t, J=5.3 Hz, 1H), 4.54 (t, J=4.8 Hz, 1H), 4.25-4.11 (m, 2H), 4.03-3.95 (m, 1H), 3.93-3.78 (m, 5H), 3.76-3.67 (m, 1H), 3.48 (s, 3H), 2.93-2.75 (m, 4H). HRMS (ESI) calcd for $C_{24}H_{29}ClN_5O_6[M+H]^+$ 518.1801; found 518.1791.

Example 35

Synthesis of N-(5-(5-chloro-4-(((3R,3aR,6R, 6aR)-6-methoxyhexahydrofurano[3,2-b]furan-3-yl)oxy) pyrimidin-2-yl)amino)-2-((S)-3,4-dimethylpiperazin-1-yl)phenyl) acrylamide (LS 6-49)

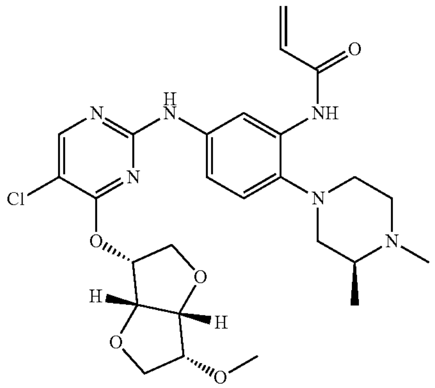 [SMILES: C=CC(=O)Nc1cc(Nc2ncc(Cl)c(O[C@@H]3CO[C@H]4[C@@H]3OC[C@H]4OC)n2)ccc1N1CCN(C)[C@@H](C)C1]

The synthesis method was the same as that of LS 6-16 in Example 32, except that (S)-1,2-dimethylpiperazine was used instead of 1-methyl-4-(piperidin-4-yl) piperazine hydrochloride (6) to participate in the reaction.

$^1$H NMR (400 MHz, $CDCl_3$) δ 8.92 (s, 1H), 8.79 (s, 1H), 8.13 (s, 1H), 7.19-6.98 (m, 3H), 6.39 (d, J=16.8 Hz, 1H), 6.26 (dd, J=16.9, 10.1 Hz, 1H), 5.89 (q, J=5.2 Hz, 1H), 5.78 (dd, J=10.0, 1.2 Hz, 1H), 5.01 (t, J=5.3 Hz, 1H), 4.55 (t, J=4.8 Hz, 1H), 4.22-4.08 (m, 2H), 4.02-3.95 (m, 1H), 3.93-3.86 (m, 1H), 3.76-3.68 (m, 1H), 3.49 (s, 3H), 3.13-2.97 (m, 2H), 2.94-2.77 (m, 2H), 2.77-2.68 (m, 1H), 2.56-2.36 (m, 5H), 1.19 (d, J=6.0 Hz, 3H). HRMS (ESI) calcd for $C_{26}H_{34}ClN_6O_5[M+H]^+$ 545.2274; found 545.2265.

Example 36

Synthesis of N-(5-(5-chloro-4-(((3R,3aR,6S,6aS)-6-fluorohexahydrofuran[3,2-b]furan-3-yl) oxygen) pyrimidin-2-yl)amino)-2-(4-(4-methylpiperazin-1-yl) piperidin-1-yl)phenyl) acrylamide (LS 6-59)

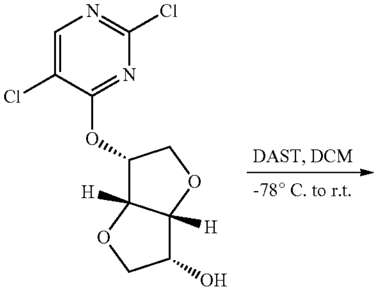

9

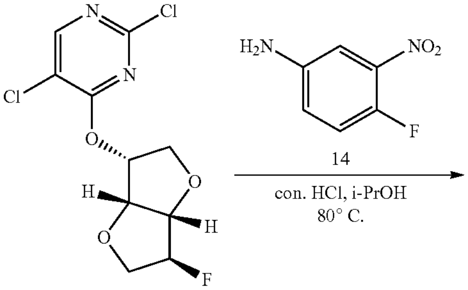

26

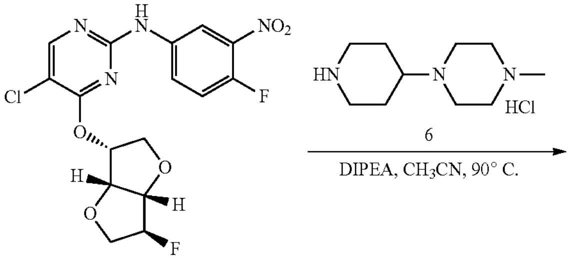

27

-continued

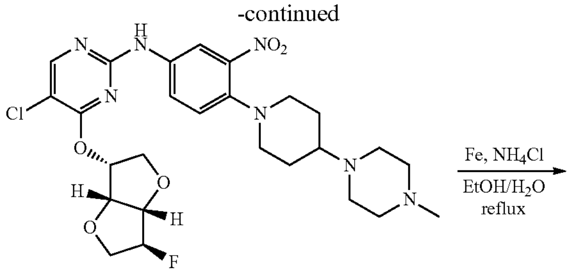

28

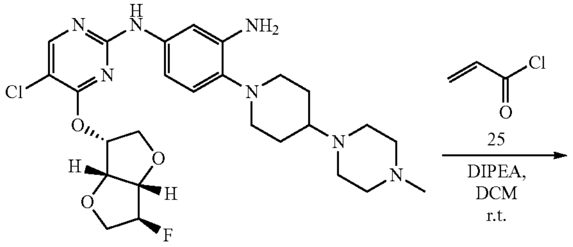

29

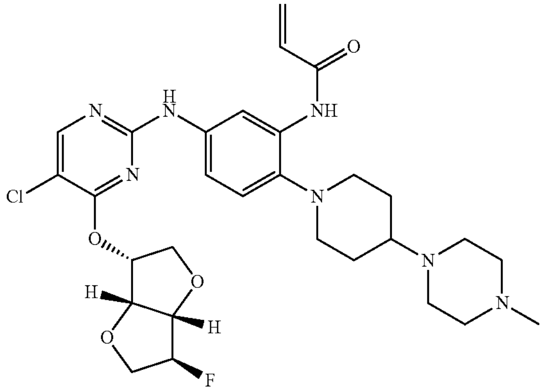
LS 6-59

Step 1 Synthesis of 2,5-Dichloro-4-(((3R,3aR,6S, 6aS)-6-fluorohexahydrofuran[3,2-b]furan-3-yl)oxy) pyrimidine (26)

Intermediate 9 (0.58 g, 2.0 mmol) was dissolved in 10 mL of anhydrous dichloromethane, and diethylamine sulfur trifluoride (DAST, 1.6 g, 10.0 mmol) was slowly added dropwise at −78° C. After the addition was complete, the reaction continued for 30 minutes, and then the reaction system was raised to room temperature and stirred overnight. After the reaction was complete, added water dropwise to the system in an ice bath environment to quench the reaction, extracted three times with dichloromethane. The organic phases were merged, washed with saturated salt water, dried over anhydrous sodium sulfate, spin-dried, and separated by column chromatography to obtain a compound 26 (0.22 g, 37%). $^1$H NMR (400 MHz, $CDCl_3$) δ 8.36 (s, 1H), 5.63 (td, J=5.4, 3.8 Hz, 1H), 5.22-5.00 (m, 2H), 4.66 (dd, J=11.2, 5.2 Hz, 1H), 4.16-3.87 (m, 4H). $^{19}$F NMR (376 MHz, $CDCl_3$) δ−188.91−−189.36 (m, 1F). MS (ESI) m/z 295.0 $[M+H]^+$.

The method of the subsequent synthesis steps was the same as that of LS 6-16 in Example 32, except that the reaction raw materials were substituted to participate in the reaction.

Compound 27: $^1$H NMR (400 MHz, $CDCl_3$) δ 8.83 (dd, J=6.4, 2.6 Hz, 1H), 8.21 (s, 1H), 7.85 (s, 1H), 7.53-7.45 (m, 1H), 7.30-7.20 (m, 1H), 5.70-5.62 (m, 1H), 5.22-5.05 (m, 2H), 4.70 (dd, J=11.6, 5.1 Hz, 1H), 4.18-3.92 (m, 4H). MS (ESI) m/z 415.1 $[M+H]^+$.

Compound 28: $^1H$ NMR (400 MHz, $CDCl_3$) δ 8.50 (d, J=2.8 Hz, 1H), 8.14 (s, 1H), 7.45 (s, 1H), 7.39 (dd, J=8.8, 2.4 Hz, 1H), 7.10 (d, J=8.9 Hz, 1H), 5.62 (td, J=5.3, 3.5 Hz, 1H), 5.19-5.01 (m, 2H), 4.68 (dd, J=11.7, 5.1 Hz, 1H), 4.12-3.90 (m, 4H), 3.32-3.24 (m, 2H), 2.87-2.39 (m, 14H), 1.93 (d, J=10.9 Hz, 2H), 1.80-1.66 (m, 2H). MS (ESI) m/z 578.2 $[M+H]^+$.

Compound 29: $^1H$ NMR (600 MHz, $CDCl_3$) δ 8.07 (s, 1H), 7.04 (s, 1H), 6.96 (d, J=2.4 Hz, 1H), 6.85 (d, J=8.4 Hz, 1H), 6.77 (dd, J=8.4, 2.4 Hz, 1H), 5.47 (dd, J=9.5, 5.4 Hz, 1H), 5.16-5.02 (m, 2H), 4.62 (dd, J=11.7, 5.0 Hz, 1H), 4.18-3.82 (m, 6H), 3.15-3.12 (m, 2H), 3.05-2.43 (m, 14H), 2.06-1.96 (m, 2H), 1.81-1.67 (m, 2H). MS (ESI) m/z 548.3 $[M+H]^+$.

Compound LS 6-59: $^1H$ NMR (400 MHz, $CDCl_3$) δ 9.02 (s, 1H), 8.76 (s, 1H), 8.14 (s, 1H), 7.21-7.05 (m, 2H), 6.95 (d, J=7.6 Hz, 1H), 6.36 (dd, J=16.9, 1.4 Hz, 1H), 6.25 (dd, J=16.9, 10.0 Hz, 1H), 6.04 (d, J=4.7 Hz, 1H), 5.77 (dd, J=9.9, 1.5 Hz, 1H), 5.20-4.95 (m, 2H), 4.62 (dd, J=11.5, 4.9 Hz, 1H), 4.19-3.90 (m, 4H), 3.01 (d, J=10.6 Hz, 2H), 2.96-2.22 (m, 14H), 2.07 (d, J=12.0 Hz, 2H), 1.66 (d, J=11.6 Hz, 2H). HRMS (ESI) calcd for $C_{29}H_{38}ClFN_7O_4$ $[M+H]^+$ 602.2652; found 602.2641.

Example 37

Synthesis of N-(5-(5-chloro-4-(((3R,3aR,6S,6aS)-6-fluorohexahydrofuran[3,2-b]furan-3-yl) oxygen) pyrimidin-2-yl)amino)-2-(2-(dimethylamino)ethyl) (methyl)amino)phenyl) acrylamide (LS 6-77)

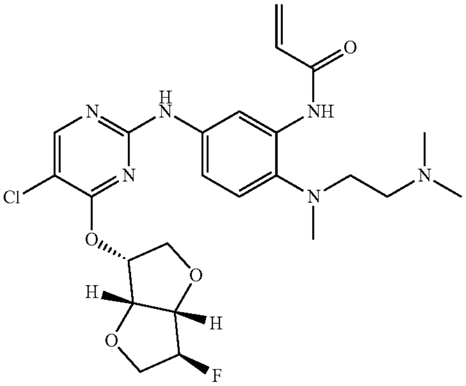 [SMILES: C=CC(=O)Nc1cc(Nc2ncc(Cl)c(O[C@@H]3CO[C@H]4[C@@H]3OC[C@@H]4F)n2)ccc1N(C)CCN(C)C]

The synthesis method was the same as that of LS 6-59 in Example 36, except that N, N, N'-trimethylethylenediamine was used instead of 1-methyl-4-(piperidin-4-yl) piperazine hydrochloride (6) to participate in the reaction.

$^1H$ NMR (600 MHz, $CDCl_3$) δ 10.23 (s, 1H), 9.07 (s, 1H), 8.14 (s, 1H), 7.25-7.08 (m, 2H), 6.98 (s, 1H), 6.50-6.26 (m, 2H), 6.08 (s, 1H), 5.77-5.66 (m, 1H), 5.22-5.02 (m, 2H), 4.63 (dd, J=11.5, 5.0 Hz, 1H), 4.19-3.92 (m, 4H), 2.87 (s, 2H), 2.69 (s, 3H), 2.65-1.89 (m, 8H). $^{13}C$ NMR (126 MHz, $CDCl_3$) δ 164.03 (s), 163.57 (s), 157.58 (s), 156.68 (s), 136.79 (s), 136.62 (s), 136.13 (s), 132.07 (s), 126.52 (s), 122.51 (s), 114.27 (s), 110.33 (s), 106.30 (s), 96.37 (s), 94.94 (s), 85.84 (d, J=30.9 Hz), 81.31 (s), 76.51 (s), 73.35 (d, J=21.9 Hz), 71.35 (s), 57.28 (s), 45.43 (s), 43.31 (s). $^{19}F$ NMR (376 MHz, $CDCl_3$) δ−188.71 (s). HRMS (ESI) calcd for $C_{24}H_{31}ClFN_6O_4[M+H]^+$ 521.2074; found 521.2056.

Example 38

Synthesis of N-(5-(5-chloro-4-(((3R,3aR,6S,6aS)-6-fluorohexahydrofuran[3,2-b]furan-3-yl)oxy) pyrimidin-2-yl)amino)-2-(4-ethylpiperazin-1-yl)phenyl) acrylamide (LS 6-78)

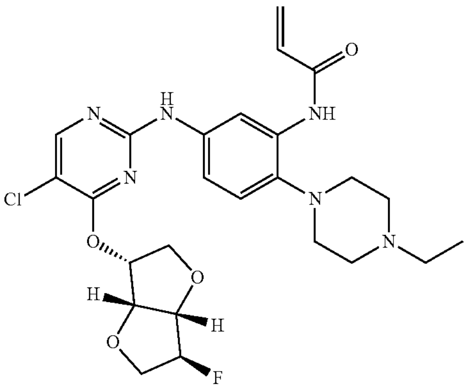 [SMILES: C=CC(=O)Nc1cc(Nc2ncc(Cl)c(O[C@@H]3CO[C@H]4[C@@H]3OC[C@@H]4F)n2)ccc1N1CCN(CC)CC1]

The synthesis method was the same as that of LS 6-59 in Example 36, except that N-ethylpiperazine was used instead of 1-methyl-4-(piperidin-4-yl) piperazine hydrochloride (6) to participate in the reaction.

$^1H$ NMR (400 MHz, $CDCl_3$) δ 9.03 (s, 1H), 8.74 (s, 1H), 8.15 (s, 1H), 7.20 (d, J=8.8 Hz, 1H), 7.09 (s, 1H), 7.01 (d, J=7.2 Hz, 1H), 6.38 (dd, J=16.9, 1.4 Hz, 1H), 6.27 (dd, J=16.8, 10.1 Hz, 1H), 6.04 (d, J=4.3 Hz, 1H), 5.79 (dd, J=10.0, 1.2 Hz, 1H), 5.18-5.03 (m, 2H), 4.63 (dd, J=11.6, 5.0 Hz, 1H), 4.14-4.04 (m, 3H), 4.00-3.94 (m, 1H), 3.18-2.57 (m, 10H), 1.30-1.25 (m, 3H). HRMS (ESI) calcd for $C_{25}H_{31}ClFN_6O_4[M+H]^+$ 533.2074; found 533.2059.

Example 39

Synthesis of N-(5-(5-chloro-4-(((3R,3aR,6R, 6aS)-6-fluorohexahydrofuran[3,2-b]furan-3-yl) oxygen) pyrimidin-2-yl)amino)-2-(2-(dimethylamino)ethyl) (methyl)amino)phenyl) acrylamide (LS 6-88)

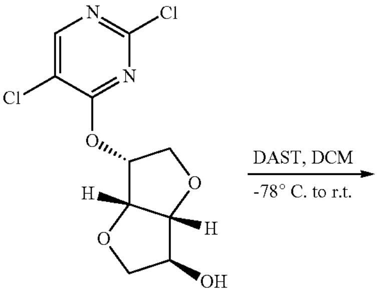

3-2

-continued

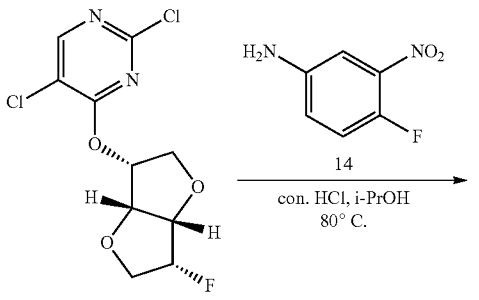

30

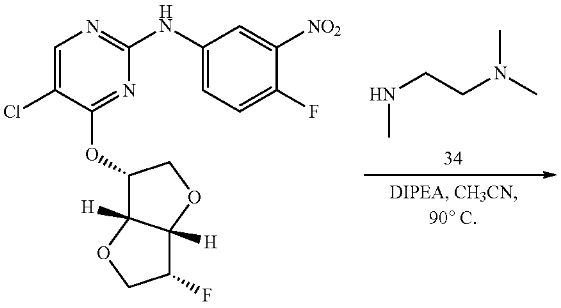

31

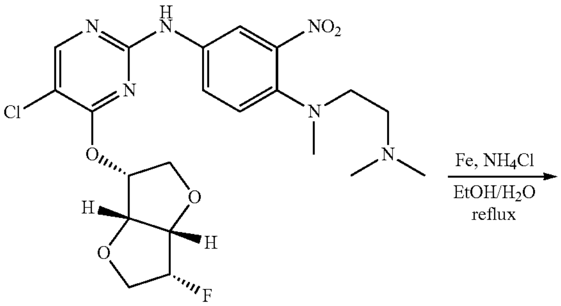

32

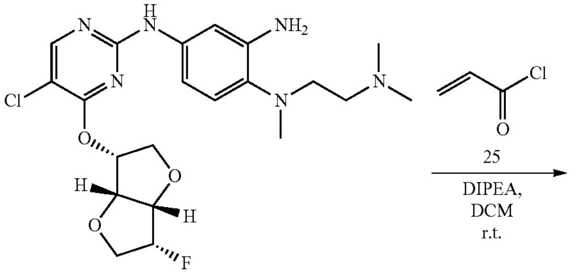

33

-continued

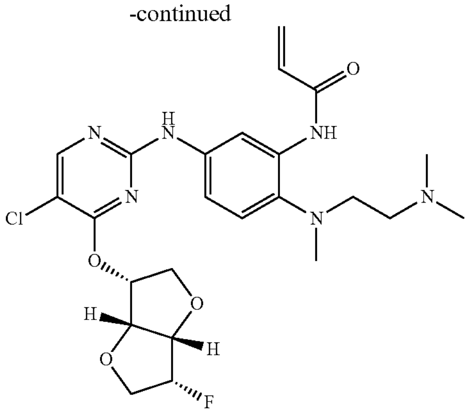

LS 6-88

The synthesis method was the same as that of LS 6-59 in Example 36, except that intermediate 3-2 was used instead of compound 9, and N,N,N'-trimethylethylenediamine (34) was used instead of 1-methyl-4-(piperidin-4-yl) piperazine hydrochloride (6) to participate in the reaction.

Compound 30: $^1$H NMR (400 MHz, $CDCl_3$) δ 8.36 (s, 1H), 5.64 (d, J=4.4 Hz, 1H), 5.28-5.02 (m, 2H), 4.67 (dd, J=11.4, 4.9 Hz, 1H), 4.15-3.89 (m, 4H). $^{19}$F NMR (376 MHz, $CDCl_3$) δ−188.95--189.30 (m, 1F). MS (ESI) m/z 295.0 $[M+H]^+$.

Compound 31: $^1$H NMR (400 MHz, $CDCl_3$) δ 8.83 (d, J=6.0 Hz, 1H), 8.20 (s, 1H), 7.52 (s, 1H), 7.46 (d, J=7.2 Hz, 1H), 7.23 (d, J=9.6 Hz, 1H), 5.66 (s, 1H), 5.23-5.07 (m, 2H), 4.70 (dd, J=11.2, 4.7 Hz, 1H), 4.16-4.00 (m, 4H). MS (ESI) m/z 415.1 $[M+H]^+$.

Compound 32: $^1$H NMR (400 MHz, $CDCl_3$) δ 8.44 (s, 1H), 8.17 (s, 1H), 7.32 (d, J=9.0 Hz, 1H), 7.19 (d, J=8.8 Hz, 1H), 7.09 (s, 1H), 5.62 (d, J=4.8 Hz, 1H), 5.23-5.04 (m, 2H), 4.71 (dd, J=12.0, 4.7 Hz, 1H), 4.19-3.91 (m, 4H), 3.34 (t, J=6.4 Hz, 2H), 2.84 (s, 3H), 2.70 (s, 2H), 2.41 (s, 6H). $^{19}$F NMR (376 MHz, $CDCl_3$) δ−188.99--189.05 (m, 1F). MS (ESI) m/z 497.1 $[M+H]^+$.

Compound LS 6-88: $^1$H NMR (600 MHz, $CDCl_3$) δ 10.22 (s, 1H), 9.07 (s, 1H), 8.14 (s, 1H), 7.21-7.07 (m, 2H), 6.98 (d, J=6.0 Hz, 1H), 6.46-6.21 (m, 2H), 6.07 (s, 1H), 5.77-5.66 (m, 1H), 5.16 (t, J=5.4 Hz, 1H), 5.10 (dd, J=50.4, 2.4 Hz, 1H), 4.63 (dd, J=11.4, 5.0 Hz, 1H), 4.23-3.85 (m, 4H), 2.98-2.75 (m, 2H), 2.69 (s, 3H), 2.61-1.91 (m, 8H). $^{13}$C NMR (126 MHz, $CDCl_3$) δ 164.04 (s), 163.62 (s), 157.54 (s), 156.68 (s), 136.77 (s), 136.59 (s), 136.13 (s), 132.07 (s), 126.54 (s), 122.48 (s), 114.23 (s), 110.35 (s), 106.36 (s), 96.37 (s), 94.94 (s), 85.85 (d, J=30.8 Hz), 81.31 (s), 76.51 (s), 73.36 (d, J=21.9 Hz), 71.36 (s), 57.22 (s), 45.38 (s), 43.34 (s). $^{19}$F NMR (376 MHz, $CDCl_3$) δ−188.74 (s). HRMS (ESI) calcd for $C_{24}H_{31}ClFN_6O_4$ $[M+H]^+$ 521.2074; found 521.2059.

Example 40

Synthesis of N-(5-(5-chloro-4-(((3R,3aR,6R, 6aS)-6-fluorohexahydrofuran[3,2-b]furan-3-yl)oxy) pyrimidin-2-yl)amino)-2-(4-ethylpiperazin-1-yl) phenyl) acrylamide (LS 6-89)

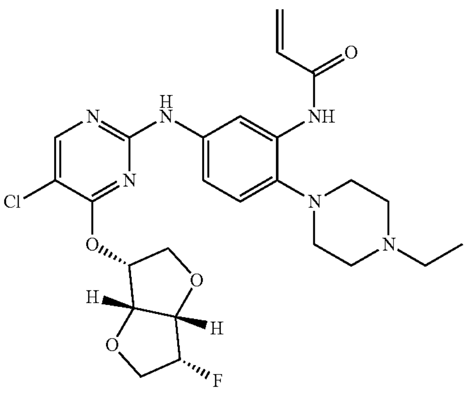 [SMILES: C=CC(=O)Nc1cc(Nc2ncc(Cl)c(O[C@@H]3CO[C@H]4[C@@H]3OC[C@H]4F)n2)ccc1N1CCN(CC)CC1]

The synthesis method was the same as that of LS 6-88 in Example 39, except that N-ethylpiperazine was used instead of N,N,N'-trimethylethylenediamine (34) to participate in the reaction.

$^1$H NMR (600 MHz, $CDCl_3$) δ 9.04 (s, 1H), 8.82 (s, 1H), 8.14 (s, 1H), 7.17 (d, J=8.4 Hz, 1H), 7.13 (s, 1H), 6.98 (d, J=6.0 Hz, 1H), 6.38 (d, J=17.4 Hz, 1H), 6.27 (dd, J=16.9, 10.1 Hz, 1H), 6.05 (s, 1H), 5.78 (dd, J=10.1, 1.0 Hz, 1H), 5.20-5.02 (m, 2H), 4.63 (dd, J=11.5, 4.9 Hz, 1H), 4.18-3.89 (m, 4H), 3.23-2.35 (m, 10H), 1.25-1.07 (m, 3H). HRMS (ESI) calcd for $C_{25}H_{31}ClFN_6O_4[M+H]^+$ 533.2074; found 533.2058.

Example 41

Synthesis of N-(5-(5-chloro-4-(((3R,3aR,6aS)-6,6-difluorohexahydrofuran[3,2-b]furan-3-yl) oxygen) pyrimidin-2-yl)amino)-2-(2-(dimethylamino)ethyl) (methyl)amino)phenyl) acrylamide (LS 6-105)

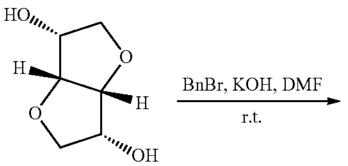

8

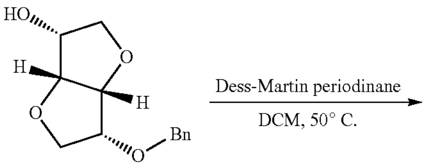

35

-continued

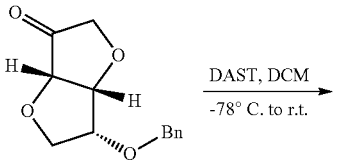

36

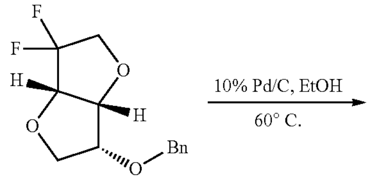

37

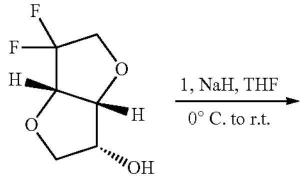

38

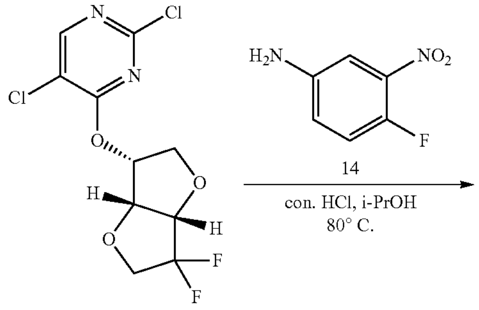

39

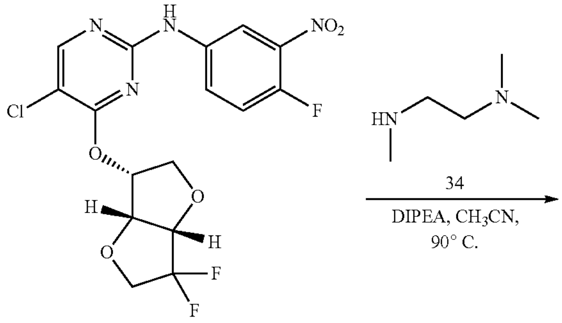

40

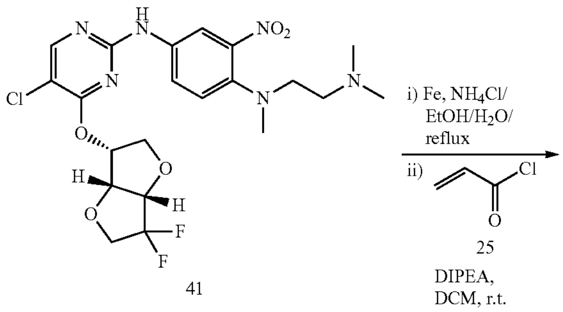

41

-continued

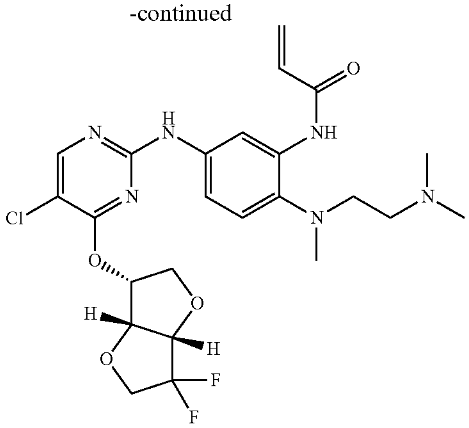

LS 6-105

Step 1 Synthesis of Intermediate 35

Potassium hydroxide (4.8 g, 85.5 mmol) was added to 80 mL of DMF solution of raw material 8 (10 g, 68.4 mmol). After being stirred at room temperature for 30 minutes, benzyl bromide (6.77 mL, 57 mmol) was slowly added dropwise to the system, and stirred overnight at room temperature. After the reaction was complete, spin-dried most of the solvent under reduced pressure, extracted three times with ethyl acetate. Then the organic phases were merged, washed with saturated salt water, dried over anhydrous sodium sulfate, spin-dried, and separated by column chromatography to obtain a compound 35 (8.5 g, 53%).

$^1$H NMR (600 MHz, DMSO-$d_6$) δ 7.54-7.25 (m, 5H), 4.81 (d, J=6.9 Hz, 1H), 4.62 (d, J=11.6 Hz, 1H), 4.53 (t, J=4.6 Hz, 1H), 4.47 (d, J=11.6 Hz, 1H), 4.29 (t, J=4.7 Hz, 1H), 4.14-4.04 (m, 2H), 3.88 (dd, J=8.3, 7.0 Hz, 1H), 3.84-3.79 (m, 1H), 3.50 (t, J=8.4 Hz, 1H), 3.40-3.35 (m, 1H). MS (ESI) m/z 237.1 $[M+H]^+$.

Step 2 Synthesis of Intermediate 36

Des Martin oxidant (DMP, 5.55 g, 13.10 mmol) was added in batches to a solution of intermediate 35 (0.62 g, 2.62 mmol) in anhydrous dichloromethane (30 mL). After stirred at room temperature for 30 minutes, the reaction system was heated to 50° C. to react overnight. After the reaction was complete, added sodium thiosulfate aqueous solution to the system to quench the reaction, and extracted three times with dichloromethane. The organic phases were combined, washed with saturated salt water, dried over anhydrous sodium sulfate, spin-dried, and separated by column chromatography to obtain a compound 36 (0.38 g, 61%). $^1$H NMR (600 MHz, $CDCl_3$) δ 7.42-7.28 (m, 5H), 4.93 (t, J=5.4 Hz, 1H), 4.75 (d, J=11.9 Hz, 1H), 4.63 (d, J=11.9 Hz, 1H), 4.32-4.23 (m, 2H), 4.16 (dd, J=10.9, 6.0 Hz, 1H), 4.07 (d, J=17.4 Hz, 1H), 3.99 (dd, J=9.3, 5.8 Hz, 1H), 3.84 (dd, J=9.3, 6.5 Hz, 1H). MS (ESI) m/z 235.1 $[M+H]^+$.

Step 2 Synthesis of Intermediate 37

Intermediate 36 (0.4 g, 1.7 mmol) was dissolved in 10 mL of anhydrous dichloromethane and slowly added diethylamine sulfur trifluoride (DAST, 1.38 g, 8.5 mmol) dropwise at −78° C. Then the reaction continued for 30 minutes, and then the temperature of the reaction system was raised to room temperature and stirred overnight. After the reaction was complete, added water dropwise to the system in an ice bath environment to quench the reaction, extracted three times with dichloromethane. The organic phases were merged, washed with saturated salt water, dried over anhydrous sodium sulfate, spin-dried, and separated by column chromatography to obtain a compound 37 (0.15 g, 35%). $^1$H NMR (600 MHz, $CDCl_3$) δ 7.44-7.28 (m, 5H), 4.75 (dd, J=10.5, 4.4 Hz, 2H), 4.57 (d, J=11.8 Hz, 1H), 4.41 (dd, J=10.0, 4.8 Hz, 1H), 4.13-3.96 (m, 4H), 3.74 (t, J=8.6 Hz, 1H). $^{19}$F NMR (376 MHz, $CDCl_3$) δ−106.76 (d, J=246.3 Hz, 1F), −126.84 (d, J=246.6 Hz, 1F). MS (ESI) m/z 257.1 $[M+H]^+$.

Step 3, Synthesis of Intermediate 38

Intermediate 37 (0.21 g, 0.82 mmol) was dissolved in anhydrous ethanol (8 mL), and under the protection by a hydrogen balloon, added a catalytic amount of 10% palladium/carbon. The temperature of the reaction system was raised to 60° C. for approximately 3 hours. After the reaction was complete and the system was filtered with a pad of Celite, spin-dried most of the solvents, extracted three times with dichloromethane. Then the organic phases were combined, washed with saturated salt water, dried over anhydrous sodium sulfate, spin-dried, and separated by column chromatography to obtain a compound 38 (0.12 g, 85%). $^1$H NMR (400 MHz, $CDCl_3$) δ 4.68 (t, J=4.9 Hz, 1H), 4.43 (dd, J=9.6, 4.8 Hz, 1H), 4.40-4.35 (m, 1H), 4.14-4.01 (m, 2H), 3.94 (ddd, J=25.2, 10.5, 6.0 Hz, 1H), 3.60 (dd, J=9.2, 7.5 Hz, 1H), 2.51 (s, 1H). $^{19}$F NMR (376 MHz, $CDCl_3$) δ−107.40 (d, J=247.4 Hz, 1F), −126.72 (d, J=247.4 Hz, 1F). MS (ESI) m/z 167.1 $[M+H]^+$.

Step 4, Synthesis of Intermediate 39

60% sodium hydride (58 mg, 1.44 mmol) was added in batches to a solution of intermediate 38 (0.12 g, 0.72 mmol) in tetrahydrofuran (THF, 4 mL) in an ice bath. After stirred for 10 minutes, added 2,4,5-trichloropyrimidine (1, 0.14 g, 0.72 mmol) dropwise to the system and stirred overnight at room temperature. After the reaction was complete, slowly added ice water to the system to quench, spin-dried most of the solvent, extracted three times with dichloromethane. The organic phases were merged, washed with saturated salt water, dried over anhydrous sodium sulfate, spin-dried, and separated with column chromatography to obtain a white solid 39 (144 mg, 64%). $^1$H NMR (400 MHz, $CDCl_3$) δ 8.37 (s, 1H), 5.60 (q, J=5.5 Hz, 1H), 5.15 (t, J=5.5 Hz, 1H), 4.49 (dd, J=10.6, 5.3 Hz, 1H), 4.24-4.15 (m, 2H), 4.04-3.93 (m, 2H). $^{19}$F NMR (376 MHz, $CDCl_3$) δ−107.24--108.04 (m, 1F), −127.41--128.09 (m, 1F). MS (ESI) m/z 313.0 $[M+H]^+$.

The synthesis methods of intermediates 40, 41, 42, and LS 6-105 were the same as that of Example 39, except that the reaction raw materials were substituted to participate in the reaction.

Compound 40: $^1$H NMR (400 MHz, $CDCl_3$) δ 8.81 (dd, J=6.6, 2.7 Hz, 1H), 8.22 (s, 1H), 7.52 (s, 1H), 7.46 (dt, J=8.9, 3.1 Hz, 1H), 7.29-7.21 (m, 1H), 5.65 (q, J=5.3 Hz, 1H), 5.20 (t, J=5.5 Hz, 1H), 4.53 (dd, J=10.8, 5.4 Hz, 1H), 4.30-4.15 (m, 2H), 4.12-3.96 (m, 2H). $^{19}$F NMR (376 MHz, $CDCl_3$) δ−107.31--108.10 (m, 1F), −124.39 (s, 1F), −127.80--128.52 (m, 1F). MS (ESI) m/z 433.1 $[M+H]^+$.

Compound 41: $^1$H NMR (400 MHz, $CDCl_3$) δ 8.41 (d, J=2.6 Hz, 1H), 8.18 (s, 1H), 7.30-7.26 (m, 1H), 7.17 (d, J=9.0 Hz, 1H), 7.11 (s, 1H), 5.60 (q, J=5.5 Hz, 1H), 5.18 (t, J=5.5 Hz, 1H), 4.53 (dd, J=10.6, 5.3 Hz, 1H), 4.20 (d, J=5.4

Hz, 2H), 4.0-3.95 (m, 2H), 3.28 (t, J=7.2 Hz, 2H), 2.84 (s, 3H), 2.61 (t, J=7.2 Hz, 2H), 2.33 (s, 6H). MS (ESI) m/z 515.2 $[M+H]^+$.

Compound LS 6-105: $^1H$ NMR (400 MHz, $CDCl_3$) δ 10.24 (s, 1H), 9.14 (s, 1H), 8.15 (s, 1H), 7.24-7.11 (m, 2H), 6.88 (d, J=7.2 Hz, 1H), 6.496.25 (m, 2H), 6.12 (d, J=5.7 Hz, 1H), 5.77-5.68 (m, 1H), 5.24 (t, J=5.4 Hz, 1H), 4.44 (dd, J=10.5, 5.1 Hz, 1H), 4.29 (dd, J=9.5, 6.5 Hz, 1H), 4.16 (dd, J=9.9, 5.5 Hz, 1H), 4.10-3.92 (m, 2H), 2.87 (s, 2H), 2.69 (s, 3H), 2.42-2.10 (m, 8H). $^{13}C$ NMR (151 MHz, $CDCl_3$) δ 163.89 (s), 163.61 (s), 157.55 (s), 156.89 (s), 136.74 (s), 136.69 (s), 136.21 (s), 131.97 (s), 126.74 (s), 122.65 (s), 114.23 (s), 110.05 (s), 106.32 (s), 81.71 (dd, J=37.6, 17.8 Hz), 81.47 (d, J=3.8 Hz), 76.09 (s), 71.64 (s), 70.88 (dd, J=31.4, 28.8 Hz), 57.35 (s), 56.59 (s), 45.52 (s), 43.29 (s). $^{19}F$ NMR (376 MHz, $CDCl_3$) δ-107.03--108.06 (m, 1F), -127.65--128.43 (m, 1F). HRMS (ESI) calcd for $C_{24}H_{30}C_1F_2N_6O_4$ $[M+H]^+$ 539.1980; found 539.1962.

Example 42

Synthesis of N-(5-(5-chloro-4-(((3R,3aS,6aR)-hexahydrofuran[3,2-b]furan-3-yl) oxygen) pyrimidin-2-yl)amino)-2-(2-(dimethylamino)ethyl)(methyl) amino)phenyl) acrylamide (LS 6-121)

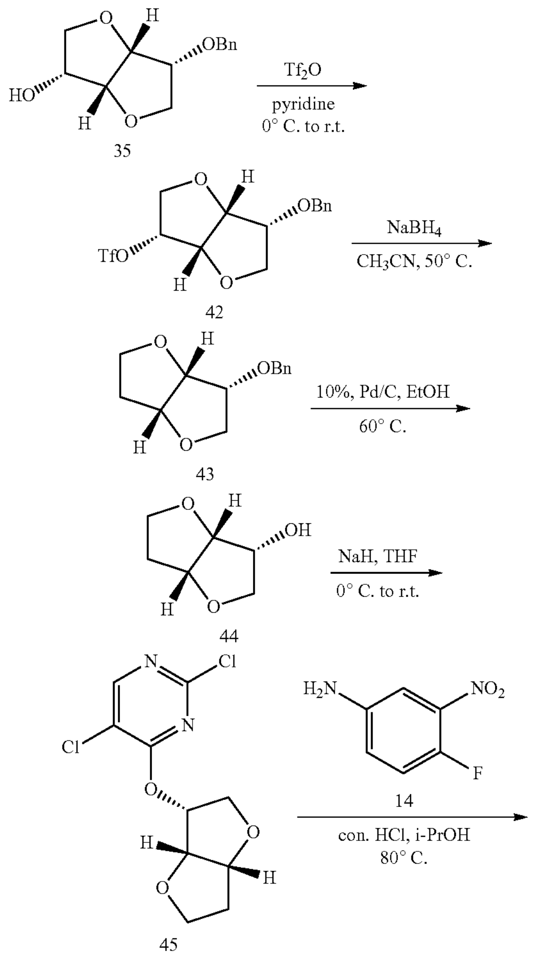

-continued

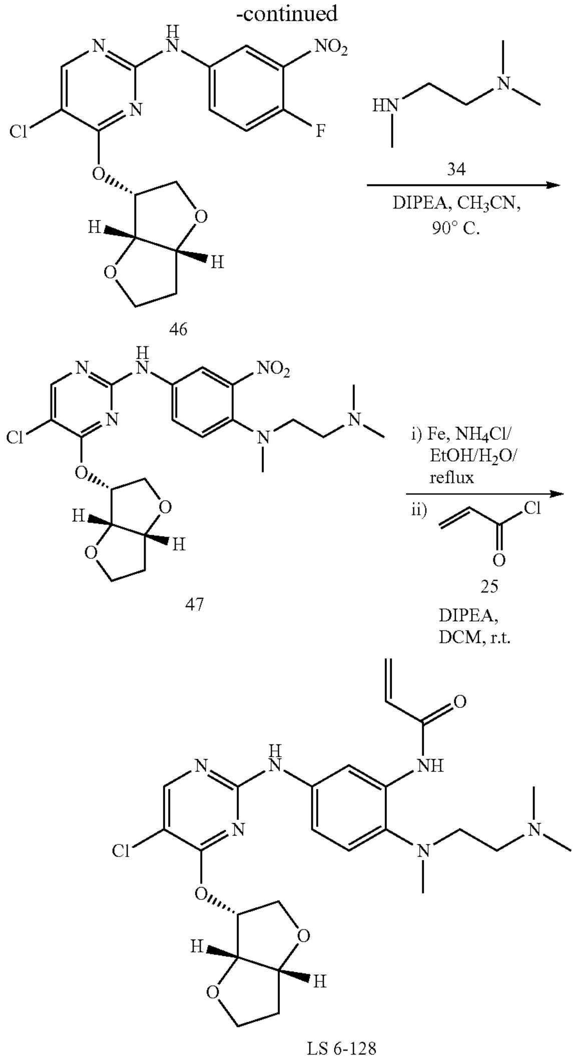

Step 1. Synthesis of Intermediate 42

Under an ice bath, trifluoromethanesulfonic anhydride (0.17 mL, 1.0 mmol) was slowly added to a solution of intermediate 35 (0.2 g, 0.85 mmol) in 5 mL pyridine. After the reaction raised to room temperature, continued stirring for 2 hours. The reaction was quenched with 4N hydrochloric acid solution, extracted three times with ethyl acetate. The organic phases were merged, washed with saturated salt water, dried over anhydrous sodium sulfate, spin-dried, and separated with column chromatography to obtain an intermediate 42 (0.24 g, 77% yield); $^1H$ NMR (400 MHz, $CDCl_3$) δ 7.46-7.27 (m, 5H), 5.20 (dd, J=10.0, 5.2 Hz, 1H), 4.73 (dd, J=11.2, 4.8 Hz, 2H), 4.58 (d, J=11.8 Hz, 1H), 4.49 (t, J=5.0 Hz, 1H), 4.17 (dd, J=10.9, 4.2 Hz, 1H), 4.11-4.05 (m, 1H), 4.04-3.97 (m, 2H), 3.73 (t, J=8.7 Hz, 1H). MS (ESI) m/z 369.1 $[M+H]^+$.

Step 2. Synthesis of Intermediate 43

At room temperature, sodium borohydride (62 mg, 1.63 mmol) was added to a solution of intermediate 42 (0.2 g, 0.54 mmol) in acetonitrile, and the reaction was heated to 50° C. and stirred overnight. The next day, the reaction solution was quenched with water, and then extracted three times with ethyl acetate. The organic phases were merged, washed with saturated salt water, dried over anhydrous sodium sulfate, spin-dried, and separated by column chromatography to obtain an intermediate 43 (86 mg, 72% yield); $^1$H NMR (400 MHz, $CDCl_3$) δ 7.41-7.26 (m, 5H), 4.78 (d, J=12.0 Hz, 1H), 4.65 (td, J=4.8, 1.7 Hz, 1H), 4.58 (d, J=12.0 Hz, 1H), 4.49 (t, J=4.7 Hz, 1H), 4.08-3.90 (m, 3H), 3.84 (dd, J=8.8, 6.5 Hz, 1H), 3.69 (dd, J=8.7, 7.7 Hz, 1H), 2.11-1.97 (m, 2H). MS (ESI) m/z 221.1 $[M+H]^+$.

Step 3. Synthesis of Intermediate 44

At room temperature, 50 mg of 10% palladium/carbon was added to a solution (5 mL) of intermediate 43 (0.3 g, 1.36 mmol) in ethanol. The reaction system reacted at 60° C. under hydrogen conditions for 4 hours. After the reaction was complete, filtered with a pad of Celite and concentrated to obtain a colorless oily substance 44, $^1$H NMR (400 MHz, $CDCl_3$) δ 4.59 (t, J=4.8 Hz, 1H), 4.46 (t, J=5.1 Hz, 1H), 4.31-4.19 (m, 1H), 4.05 (td, J=8.3, 2.4 Hz, 1H), 3.89-3.76 (m, 2H), 3.66 (dd, J=9.6, 4.9 Hz, 1H), 2.79 (d, J=6.2 Hz, 1H), 2.14 (dd, J=13.0, 5.3 Hz, 1H), 2.09-1.96 (m, 1H). MS (ESI) m/z 131.1 $[M+H]^+$.

Step 4. The synthesis of intermediates 45, 46, 47, and target product LS6-121 was the same as that of LS5-12, except that the reaction raw materials were substituted accordingly to participate in the reaction.

Compound 45: $^1$H NMR (400 MHz, $CDCl_3$) δ 8.34 (s, 1H), 5.58 (td, J=5.4, 3.2 Hz, 1H), 4.86 (t, J=5.4 Hz, 1H), 4.64 (t, J=5.2 Hz, 1H), 4.15 (dd, J=10.7, 3.2 Hz, 1H), 4.01-3.88 (m, 2H), 3.87-3.78 (m, 1H), 2.13 (dd, J=13.4, 5.2 Hz, 1H), 2.05-1.89 (m, 1H). MS (ESI) m/z 277.0 $[M+H]^+$.

Compound 46: $^1$H NMR (400 MHz, $CDCl_3$) δ 8.83 (dd, J=6.6, 2.8 Hz, 1H), 8.19 (s, 1H), 7.44 (dt, J=8.9, 3.2 Hz, 1H), 7.31 (s, 1H), 7.25-7.17 (m, 1H), 5.59 (td, J=5.3, 2.8 Hz, 1H), 4.93 (t, J=5.4 Hz, 1H), 4.68 (t, J=5.2 Hz, 1H), 4.20 (dd, J=10.7, 2.8 Hz, 1H), 3.98-3.84 (m, 3H), 2.15 (dd, J=13.2, 4.6 Hz, 1H), 2.01-1.87 (m, 1H). MS (ESI) m/z 397.1 $[M+H]^+$.

Compound 47: $^1$H NMR (400 MHz, $CDCl_3$) δ 8.43 (d, J=2.6 Hz, 1H), 8.15 (s, 1H), 7.32-7.26 (m, 1H), 7.13 (d, J=8.9 Hz, 1H), 7.03 (s, 1H), 5.56 (td, J=5.2, 3.2 Hz, 1H), 4.90 (t, J=5.4 Hz, 1H), 4.69 (t, J=5.1 Hz, 1H), 4.17 (dd, J=10.6, 3.1 Hz, 1H), 4.00-3.83 (m, 3H), 3.22 (t, J=7.2 Hz, 2H), 2.83 (s, 3H), 2.57-2.48 (m, 2H), 2.26 (s, 6H), 2.14 (dd, J=13.1, 4.0 Hz, 1H), 1.98-1.90 (m, 1H). MS (ESI) m/z 479.2 $[M+H]^+$.

LS 6-121: $^1$H NMR (400 MHz, $CDCl_3$) δ 10.22 (s, 1H), 8.93 (s, 1H), 8.14 (s, 1H), 7.24-6.97 (m, 3H), 6.41 (dd, J=17.0, 1.9 Hz, 1H), 6.36-6.26 (m, 1H), 5.90 (d, J=3.7 Hz, 1H), 5.71 (dd, J=9.9, 1.9 Hz, 1H), 4.91 (t, J=5.3 Hz, 1H), 4.63 (t, J=5.0 Hz, 1H), 4.14 (dd, J=10.3, 3.6 Hz, 1H), 4.02 (dd, J=10.3, 5.3 Hz, 1H), 3.96-3.83 (m, 2H), 2.92-2.77 (m, 2H), 2.69 (s, 3H), 2.50-2.13 (m, 8H), 2.15-2.07 (m, 1H), 1.95-1.90 (m, 1H). $^{13}$C NMR (151 MHz, $CDCl_3$) δ 164.30 (s), 163.60 (s), 157.61 (s), 156.52 (s), 136.87 (s), 136.63 (s), 136.15 (s), 132.06 (s), 126.57 (s), 122.54 (s), 114.30 (s), 110.44 (s), 106.59 (s), 83.69 (s), 81.89 (s), 71.49 (s), 69.01 (s), 57.38 (s), 56.58 (s), 45.54 (s), 43.33 (s), 34.21 (s). HRMS (ESI) calcd for $C_{24}H_{32}ClN_6O_4[M+H]^+$ 503.2168; found 503.2160.

Example 43

Synthesis of N-(5-(5-chloro-4-(((3R,3aR,6R, 6aR)-6-ethoxyhexahydrofuran[3,2-b]furan-3-yl)oxy) pyrimidin-2-yl)amino)-2-(2-(dimethylamino)ethyl) (methyl)amino)phenyl) acrylamide (LS 7-13)

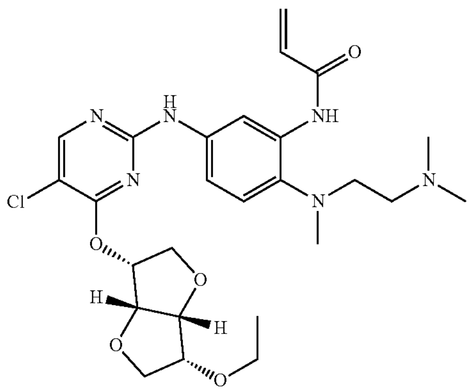 [SMILES: C=CC(=O)Nc1cc(Nc2ncc(Cl)c(O[C@@H]3CO[C@H]4[C@@H]3OC[C@H]4OCC)n2)ccc1N(C)CCN(C)C]

The synthesis method was the same as that of LS 6-16 in Example 32, except that iodoethane was used instead of iodomethane, and N,N,N'-trimethylethylenediamine was used instead of 1-methyl-4-(piperidin-4-yl) piperazine hydrochloride (6) to participate in the reaction.

$^1$H NMR (400 MHz, $CDCl_3$) δ 10.22 (s, 1H), 8.95 (s, 1H), 8.13 (s, 1H), 7.16 (d, J=8.6 Hz, 1H), 7.08 (d, J=8.8 Hz, 1H), 7.04 (s, 1H), 6.45-6.26 (m, 2H), 5.95-5.87 (m, 1H), 5.70 (dd, J=9.9, 1.7 Hz, 1H), 5.00 (t, J=5.3 Hz, 1H), 4.51 (t, J=4.5 Hz, 1H), 4.22 (dd, J=10.0, 4.5 Hz, 1H), 4.15 (dd, J=10.1, 5.8 Hz, 1H), 4.03-3.90 (m, 2H), 3.79-3.67 (m, 2H), 3.60-3.51 (m, 1H), 2.85 (t, J=4.8 Hz, 2H), 2.68 (s, 3H), 2.49-2.00 (m, 8H), 1.30-1.25 (m, 3H). $^{13}$C NMR (151 MHz, $CDCl_3$) δ 164.25 (s), 163.55 (s), 157.54 (s), 156.56 (s), 136.83 (s), 136.62 (s), 136.16 (s), 132.04 (s), 126.57 (s), 122.57 (s), 114.25 (s), 110.28 (s), 106.63 (s), 81.37 (s), 80.41 (s), 79.94 (s), 71.97 (s), 69.89 (s), 66.32 (s), 57.40 (s), 56.63 (s), 45.56 (s), 43.31 (s), 15.39 (s). HRMS (ESI) calcd for $C_{26}H_{36}ClN_6O_5[M+H]^+$ 547.2430; found 547.2420.

Example 44

Synthesis of N-(5-(5-chloro-4-(((3R,3aR,6R, 6aR)-6-isopropoxyhexahydrofuran[3,2-b]furan-3-yl)oxy) pyrimidin-2-yl)amino)-2-(2-(dimethylamino)ethyl) (methyl)amino)phenyl) acrylamide (LS 7-18)

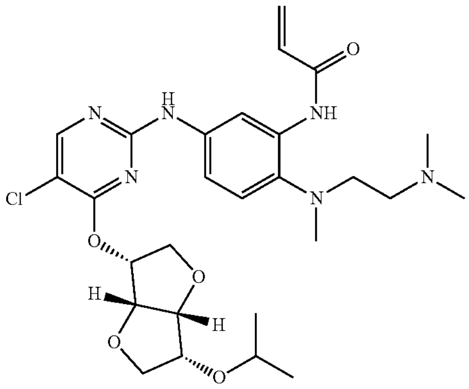 [SMILES: C=CC(=O)Nc1cc(Nc2ncc(Cl)c(O[C@@H]3CO[C@H]4[C@@H]3OC[C@H]4OC(C)C)n2)ccc1N(C)CCN(C)C]

The synthesis method was the same as that of LS 6-16 in Example 32, except that iodoisopropane was used instead of iodomethane, and N,N,N'-trimethylethylenediamine was used instead of 1-methyl-4-(piperidin-4-yl) piperazine hydrochloride (6) to participate in the reaction.

$^1$H NMR (400 MHz, $CDCl_3$) δ 10.22 (s, 1H), 8.94 (s, 1H), 8.13 (s, 1H), 7.16 (d, J=8.6 Hz, 1H), 7.09 (d, J=7.8 Hz, 1H), 7.05 (s, 1H), 6.41 (dd, J=16.9, 1.9 Hz, 1H), 6.30 (dd, J=17.1, 9.8 Hz, 1H), 5.90 (dd, J=10.0, 5.1 Hz, 1H), 5.70 (dd, J=9.8, 1.9 Hz, 1H), 4.98 (t, J=5.2 Hz, 1H), 4.45 (t, J=4.7 Hz, 1H), 4.22 (dd, J=10.1, 4.4 Hz, 1H), 4.13 (dd, J=10.1, 5.8 Hz, 1H), 4.07-3.97 (m, 1H), 3.97-3.88 (m, 1H), 3.81-3.65 (m, 2H), 2.85 (t, J=5.6 Hz, 2H), 2.69 (s, 3H), 2.50-1.94 (m, 8H), 1.25 (d, J=6.1 Hz, 3H), 1.20 (d, J=6.1 Hz, 3H). $^{13}$C NMR (151 MHz, $CDCl_3$) δ 164.28 (s), 163.53 (s), 157.56 (s), 156.53 (s), 136.85 (s), 136.62 (s), 136.15 (s), 132.04 (s), 126.56 (s), 122.56 (s), 114.27 (s), 110.30 (s), 106.61 (s), 81.21 (s), 80.95 (s), 77.94 (s), 77.14 (s), 72.18 (s), 71.94 (s), 69.99 (s), 57.41 (s), 56.66 (s), 45.58 (s), 43.30 (s), 22.54 (d, J=69.9 Hz). HRMS (ESI) calcd for $C_{27}H_{38}ClN_6O_5$ $[M+H]^+$ 561.2587; found 561.2571.

Example 45 Kinase Inhibitory Activity Test of 2-Aminopyrimidine Compounds

The kinase inhibitory activity of the compounds of the present disclosure against four members of the JAK family (JAK1, JAK2, JAK3, and TYK2) were tested using the Z'-Lyte method, wherein each kinase has an ATP concentration of $K_m$. Due to the higher ATP affinity of JAK3 compared to other family members, the kinase inhibitory activity of the compounds against JAK3 were also tested in this example at an ATP concentration of 1 mM.

Test method: Firstly, test compounds were prepared into 10 mM stock solution with DMSO, and continuously diluted into 10 concentrations at a 3-fold gradient for later use. 5X reaction buffer was diluted with deionized water into 1×reaction buffer (50 mM HEPES pH 7.5, 0.01% Brij-35, 10 mM $MgCl_2$, 1 mM EGTA), which was used to prepare a mixture of kinase and peptide substrate, as well as a phosphorylated peptide substrate solution. The kinase concentration was determined based on enzyme titration, and the final concentration of peptide substrate and phosphorylated peptide substrate was 2 μM. 5 μL of mixture substrate of kinase and peptide substrate was added to each well on the 384 well plate. Then 5 nL of the test compound (starting with a final concentration of 10 μM) was added with an Echo520 Sampler. After shaking and mixing at room temperature for 15 minutes, added an appropriate amount of ATP to the well to meet the test requirements (note: according to the concentration recommended in manufacturer's instructions, the ATP concentration for JAK1 kinase test is 75 μM, 25 μM for JAK2 kinase test, M for JAK3 kinase test, and 25 μM for TYK2 kinase test). An additional 100% phosphorylation well (5 μL phosphorylated peptide substrate solution), a 0% phosphorylated well (5 μL of a mixture of kinase and peptide substrate, without test compounds and ATP), and a 0% inhibitory well (5 μL of a mixture of kinase and peptide substrate and appropriate concentration of ATP) were set as control. Two repeats were set for each concentration. The above reaction system was incubated at 30° C. for 1.5 hours. Buffer A Dilute of kit Development was used to dilute Development reagent B at a ratio 1:128. 2.5 μL of the diluted mixture was added to each well and the system was incubated at 30° C. for another 1 hour. The plate was placed on the Envision instrument for detection, under an excitation wavelength of 400 nm, the emission wavelengths of 460 nm and 535 nm was detected. The substrate phosphorylation rate was obtained by calculating the ratio, and the activity of the kinase and the effect of the inhibitor on the kinase was further calculated. Every experiment was repeated at least three times.

The compound numbers (corresponding to the compound numbers in Examples 1-44) and corresponding kinase activity results are listed in Table 3.

TABLE 3

Kinase Inhibition Activity of the Compounds

| Compound | $IC_{50}$ (nM) | | | | |
|---|---|---|---|---|---|
| numbers | JAK1[a] | JAK2[a] | JAK3[a] | TYK2[a] | JAK3[b] |
| LS 3-96 | >10 μM | 8161 | 268 | >10 μM | >10 μM |
| LS 4-97 | 672 | 406.4 | 31.8 | 170 | 4960 |
| LS 4-104 | 1517 | 291.5 | 18.4 | 150 | 1741 |
| LS 4-100 | NT | NT | >10 μM | NT | NT |
| LS 4-106 | NT | NT | 638 | NT | NT |
| LS 5-58 | 161.3 | 669.7 | 120.0 | NT | NT |
| LS 4-144 | NT | NT | 84.8 | NT | NT |
| LS 4-142 | NT | NT | 49.5 | NT | NT |
| LS 4-145 | 470.5 | 981.1 | 66.0 | 301.4 | 4286 |
| LS 4-143 | 617.8 | 540.7 | 47.4 | 421.1 | >10 μM |
| LS 4-148 | NT | NT | 6470 | NT | NT |
| LS 5-16 | 354.2 | 948.7 | 141.2 | NT | NT |
| LS 4-150 | NT | NT | 84.0 | NT | NT |
| LS 5-54 | >10 μM | >10 μM | 5750 | NT | NT |
| LS 5-3 | >10 μM | >10 μM | 133.4 | NT | NT |
| LS 5-12 | 1540 | 1031 | 1.8 | 368.7 | 7.387 |
| LS 5-77 | 555.8 | 1404 | 1.25 | 93.9 | 2.392 |
| LS 5-62 | 1064 | 11030 | 2.2 | 859.8 | 2.262 |
| LS 5-66 | 1115 | 1162 | 5.9 | 335.2 | 14.4 |
| LS 5-74 | 1118 | 1522 | 4.26 | 225.7 | 7.372 |
| LS 5-72 | 2666 | 1542 | 90.54 | 429.9 | 4378 |
| LS 5-73 | 1734 | 1630 | 72.36 | 312.5 | 4941 |
| LS 5-81 | 4880 | 2365 | 56.95 | 278.5 | 4186 |
| LS 5-88 | 2874 | 1374 | 1.93 | 424.1 | 2.246 |
| LS 5-91 | 894.9 | 1065 | 5.5 | 233.3 | 20.62 |
| LS 5-102 | 1042 | 436.8 | 2.50 | 241.2 | 2.678 |
| LS 5-126 | 4773 | 2085 | 3.9 | 3115 | 4.352 |
| LS 5-133 | 684.6 | 416.8 | 6.336 | 312.7 | NT |
| LS 5-143 | 480.8 | 362.5 | 2.19 | 166.3 | 2.175 |
| LS 5-150 | 270.5 | 606.5 | 1.98 | 186.4 | 1.743 |
| LS 5-152 | 190.4 | 357.4 | 1.50 | 147.6 | 1.286 |

TABLE 3-continued

Kinase Inhibition Activity of the Compounds

| Compound numbers | $IC_{50}$ (nM) JAK1[a] | JAK2[a] | JAK3[a] | TYK2[a] | JAK3[b] |
|---|---|---|---|---|---|
| LS 5-154 | 800.5 | 524.4 | 1.56 | 187.5 | 1.592 |
| LS 6-16 | 533.2 | 966.8 | 8.12 | 906.3 | 12.46 |
| LS 6-45 | 12960 | 2039 | 1.255 | 1085 | 1.530 |
| LS 6-48 | 2748 | 1127 | 3.874 | 637.3 | 26.09 |
| LS 6-49 | 4685 | 1099 | 1.704 | 1193 | 2.916 |
| LS 6-59 | 7044 | 1085 | 3.270 | 435.4 | 7.576 |
| LS 6-77 | 33890 | 2468 | 1.279 | 920.7 | 1.551 |
| LS 6-78 | 12640 | 1668 | 4.020 | 911.9 | 7.136 |
| LS 6-88 | 87140 | 1720 | 1.349 | 930.0 | 1.533 |
| LS 6-89 | 15620 | 1708 | 4.257 | 805.0 | 6.537 |
| LS 6-105 | 4224 | 588.7 | 1.133 | 272.1 | 1.320 |
| LS 6-121 | 2934 | 1057 | 1.4 | 277.9 | 1.6 |
| LS 7-13 | 8602 | 1892 | 1.3 | 1657 | 1.9 |
| LS 7-18 | >10 μM | 2662 | 1.5 | 4417 | 2.3 |
| Tofacitinib | 6.62 | 25.95 | 3.0 | 111.9 | 473.7 |
| PF-06651600 | >10 μM | >10 μM | 2.321 | >10 μM | 2.420 |

The concentration of [a]ATP is $K_m$; the concentration of [b]ATP is 1 mM.

According to the detection results of kinase activity (Table 3), the compounds of the present disclosure exhibited high selective inhibitory activity against JAK3 subtype kinase. Some compounds (such as LS 5-12, LS 5-77, LS 5-62, LS 5-66, LS 5-74, LS 5-88, LS 5-91 LS 5-102, LS 5-143, LS 5-150, LS 5-152, LS 5-154, LS 6-45, LS 6-49, LS 6-77, LS 6-88, LS 6-105-LS 6-121-LS 7-13-LS 7-18, etc) exhibited strong and selective JAK3 kinase inhibitory activity, and maintained strong activity at an ATP concentration of 1 mM.

Example 46 In Vitro Proliferation Inhibitory Activity of 2-Aminopyrimidine Compounds on Tumor Cells Cell lines: human chronic myeloid leukemia cell line K562, human acute myeloid leukemia cell line U937, human T lymphocyte leukemia cell line HuT78, and human T lymphoblastic lymphoma cell line Jurkat. Cells were purchased from the Chinese Academy of Sciences Stem Cell Bank or ATCC.

Method: CCK-8 (cell counting kit-8) method, which is described as follows: Tumor cells in logarithmic growth phase were inoculated into 96-well plates at a density of $1*10^4$ cells/well. Parietal cell were cultured overnight and suspended cells were directly stimulated with drugs. Different concentrations of test compounds were added (maximum working concentration was 10 μM, and 10 gradients were diluted at a ratio of 1:3). Two repeats were set for each concentration, with a final volume of 200 μL. After treatment with drug for 72 hours, 10 μL of CCK-8 reagent was added to each well and continued incubation for 1-3 hours. The absorbance values at 450 nm and 650 nm were measured using a microplate reader, and the increment Z (A450-A650) was derived. The inhibitory rate of drugs on cell growth was calculated by GraphPad Prism 8.0.0 through the following formula:

$$\text{Inhibition rate (\%)}(OD_{control}-OD_{dosing})/OD_{control}\times 100\%$$

The half inhibitory concentration ($IC_{50}$) was calculated. Every experiment was repeated at least three times.

TABLE 4

Inhibitory activity of compounds ($IC_{50}$( μM)) on cell proliferation

| | K562 | U937 | JURKAT | HUT78 |
|---|---|---|---|---|
| LS 4-104 | 0.542 | 0.5274 | 2.053 | 2.424 |
| LS 4-145 | 0.8215 | 0.5160 | 9.033 | 2.388 |
| LS 4-143 | 0.3536 | 0.7392 | 6.339 | 3.384 |
| LS 5-3 | 0.3757 | 5.383 | 8.669 | 8.078 |
| LS 5-12 | 0.2905 | 0.03588 | 0.434 | 0.03167 |
| LS 5-77 | 0.1027 | 0.1059 | 1.659 | 0.447 |
| LS 5-62 | 0.6372 | 0.1107 | 2.464 | 0.423 |
| LS 5-66 | 1.862 | 0.08751 | 2.644 | 1.092 |
| LS 5-74 | 0.09183 | 0.1813 | 3.953 | 0.448 |
| LS 5-72 | 2.756 | 0.5244 | 2.78 | 0.9275 |
| LS 5-73 | 0.1166 | 0.2461 | 2.245 | 0.476 |
| LS 5-81 | 5.976 | 0.2270 | 3.052 | 1.062 |
| LS 5-88 | 0.4174 | 0.01528 | 0.1108 | 0.08106 |
| LS 5-91 | 0.07089 | 0.005779 | 0.03413 | 0.01916 |
| LS 5-102 | 0.8664 | 0.0211 | 0.2905 | 0.09243 |
| LS 5-126 | 0.03994 | 0.06922 | 0.5506 | 0.4633 |
| LS 5-143 | 0.216 | 0.01199 | 0.1277 | 0.07528 |
| LS 5-150 | 0.8972 | 0.01583 | 0.275 | 0.2719 |
| LS 5-152 | 0.04724 | 0.01955 | 0.2881 | 0.4277 |
| LS 5-154 | 2.409 | 0.03400 | 0.3465 | 0.717 |
| LS 6-16 | 0.1911 | 0.02403 | 0.1363 | 0.1213 |
| LS 6-45 | 0.3354 | 0.02023 | NT | NT |
| LS 6-48 | 1.547 | 0.4032 | NT | NT |
| LS 6-49 | 0.371 | 0.07941 | NT | NT |
| LS 6-59 | 0.2808 | 0.129 | NT | NT |
| LS 6-77 | 0.9062 | 0.04067 | NT | NT |
| LS 6-78 | 0.5249 | 0.1457 | NT | NT |
| LS 6-88 | 0.4104 | 0.05028 | NT | NT |
| LS 6-89 | 0.6196 | 0.1712 | NT | NT |
| LS 6-105 | 0.3448 | 0.03384 | NT | NT |
| LS 6-121 | NT | 0.03127 | NT | NT |
| LS 7-13 | NT | 0.02988 | NT | NT |
| LS 7-18 | NT | 0.04401 | NT | NT |
| tofacitinib | 21.67 | 0.1224 | >30 | >30 |
| PF-06651600 | >30 | 0.01953 | >30 | >30 |

The results (Table 4) showed that the 2-aminopyrimidine compounds of the present disclosure significantly inhibited the proliferation of various blood cancer cells, and some compounds had better inhibitory activity on tumor cells than the positive control compounds Tofacitinib and PF-06651600.

Example 47 In Vivo Pharmacokinetic Properties of Representative Molecule LS6-45 in Rats Solvent: intravenous with 5% DMSO+10% polyethylene glycol 15 hydroxystearate+85% physiological saline, oral with 0.5% hydroxypropyl methyl cellulose.

Species: SD rats, SPF grade. The animals were transferred from the animal reserve of the experimental institution (999M-017), Shanghai Xipur Bikai Experimental Animal Co., Ltd.

Number of rats: 3 in each group, male.

The animals in the oral administration group were fasted overnight (10-14 hours) before administration, and were fed 4 hours after administration. The animals were weighed before administration, and the dosage was calculated based on body weight. The drug was administered intravenously (iv, 5 mg/kg) or orally by gavage (po, 15 mg/kg). Blood was collected from jugular vein at 0.083 h, 0.25 h, 0.5 h, 1 h, 2 h, 4 h, 6 h, and 8 h after administration. About 0.20 mL of each sample was collected, anticoagulated with heparin sodium, placed on ice after collection, and centrifuged to separate plasma within 1 hour (centrifugation condition: 6800 g, 6 minutes, 2-8° C.). Plasma samples were stored in a −80° C. freezer until analysis. The analysis of biological samples and all samples were completed by the analysis laboratory of Medicipia Pharmaceutical Technology (Shanghai) Co., Ltd. The intraday accuracy evaluation of the quality control samples was conducted while the samples was analyzed, and the accuracy of over 66.7% of the quality control samples was required to be between 80-120%. Pharmacokinetic parameters were calculated using Phoenix WinNonlin7.0 based on the blood drug concentration data at different time points, providing the pharmacokinetic parameters and their average values, and standard deviations.

All procedures related to animal handling, care, and treatment in the experiment followed the protocol of the Ethics Committee for Experimental Animals Care and the Guidelines for the Care and Use of Experimental Animals in Shanghai, China.

Figure 3:
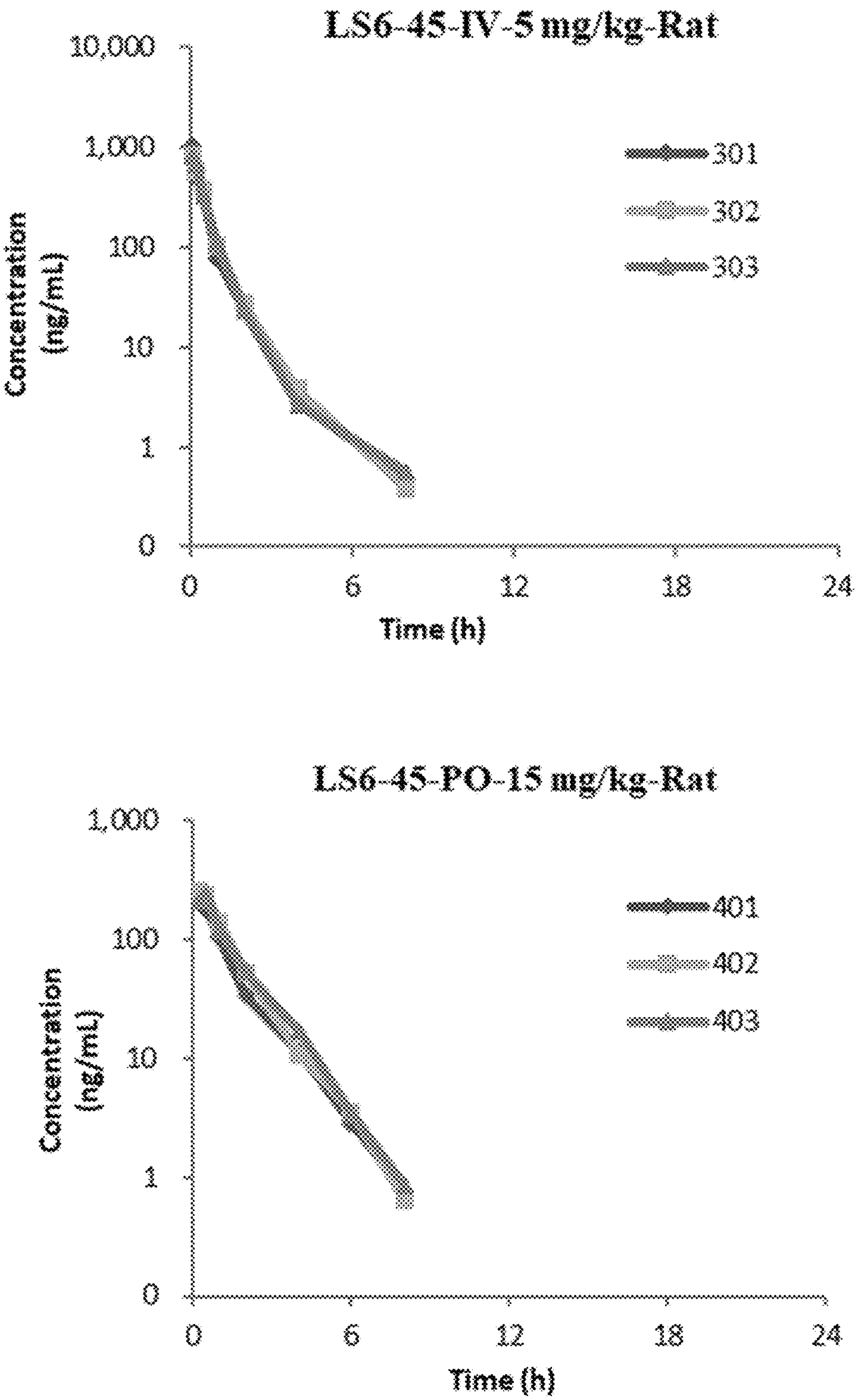
FIG. 3 shows the pharmacokinetic experimental results of compound LS6-45.

The experimental results are shown in Table 5 and FIG. 3.

TABLE 5

Pharmacokinetic parameters of Compound LS 6-45

| LS 6-45 | iv (5 mg/kg) | po (15 mg/kg) |
|---|---|---|
| Number of animals | 3 | 3 |
| $C_{max}$ (ng/mL) | 911.33 ± 139.73 | 238.28 ± 13.68 |
| $AUC_{(0-\infty)}$ (h*ng/mL) | 536.99 ± 9.89 | 333.50 ± 45.52 |
| CL (mL/min/kg) | 155.22 ± 2.83 | |
| F (%) | | 20.66 ± 2.83 |

The experimental data of pharmacokinetic in rats (Table 5 and FIG. 3) showed that compound LS6-45 had higher $C_m$a, area under curve (AUC), and oral availability (F=20.66%), indicating that the compound had good pharmacokinetic properties and the potential for oral administration.

Example 48 Rat Liver Microsomes Stability Test of Representative Molecule LS6-45

Firstly, preheated 0.1 M potassium phosphate buffer with 5 mM $MgCl_2$ (i.e. K/Mg buffer) at pH 7.4±0.1. Prepared the spiked solution for the tested compound and reference compound (500 µM spiked solution: added 5 µL of 10 mM stock solution into 95 µL of acetonitrile; 1.5 µM microsomal spiked solution (0.75 mg/mL): added 1.5 µL of 500 µM spiked solution and 18.75 µL of 20 mg/mL liver microsomes into 479.75 µL of K/Mg buffer). Then NADPH was dissolved in buffer K to prepare a 6 mM, 5 mg/mL NADPH stock solution. At different time points (0-, 5-, 15-, 30-, 45 minutes), 30 µL of 1.5 µM spiked solution containing 0.75 mg/mL of microsome solution was distributed onto the designated detection plate. At 0 min, 150 µL of acetonitrile containing internal standard (IS) was added to the 0 min plate well, followed by 15 µL of NADPH stock solution (6 mM). Then, all plates were pre-incubated at 37° C. for 5 minutes, added 15 µL of NADPH stock solution (6 mM), the reaction was initiated and timed. At 5 minutes, 15 minutes, 30 minutes, and 45 minutes, added 150 µL of acetonitrile solution containing IS to the corresponding wells to stop the reaction. After quenching, the plate was shaken for 10 minutes (600 rpm/min), followed by centrifugation at 6000 rpm/min for 15 minutes. 80 µL of supernatant of each well were transferred into a 96-well sample plate containing 140 µL of ultrapure water to perform LC/MS analysis. The analysis of biological samples and all samples were completed by the analysis laboratory of Medicipia Pharmaceutical Technology (Shanghai) Co., Ltd.

TABLE 6

Experimental Results of the stability of rat liver microsomes

| Sample | Species and genera | | Remaining percentage (%) 0 min | 5 min | 15 min | 30 min | 45 min | $T_{1/2}$ (min) | $Cl_{int}$ (mL/min/kg) |
|---|---|---|---|---|---|---|---|---|---|
| ketanserin | Rat | Average value | 100.00 | 75.87 | 42.60 | 29.98 | 17.88 | 18.71 | 132.72 |
| | | RSD | 0.00 | 0.03 | 0.20 | 0.01 | 0.01 | | |
| LS6-45 | Rat | Average value | 100.00 | 95.76 | 90.38 | 87.93 | 79.61 | >120 (149.87) | <20.70 (16.57) |
| | | RSD | 0.01 | 0.02 | 0.01 | 0.02 | 0.00 | | |

The experimental data of liver microsomes stability (Table 6) showed that the stable half-life $T_{1/2}$ of liver microsomes with reference to the molecule Ketanserin is 18.71 minutes, which was consistent with historical data, indicating the reliability of the experiment. The half-life Tin of the molecule LS6-45 in the Example was greater than 120 minutes, indicating that the molecule had higher liver microsome stability.

Example 49 Representative Molecule LS6-45 can Effectively Downregulate JAK3-STAT Signaling in U937 Cells Cell line: human acute myeloid leukemia cell line U937

Time dependent experiment: the tested molecule LS6-45 was co-incubated with U937 cells at a fixed concentration (100 nM), and the total cell protein was extracted at a specific action time. Dose dependent experiment: After co-incubating the tested molecule LS6-45 at different concentrations with U937 cell line for 10 hours, the total cell protein was extracted. Suspended cells U937 were centrifuged to remove the supernatant, washed twice with PBS, and then added an appropriate amount of lysate mixture (RIPA lysate (strong): phosphatase inhibitor mixture (50×): PMSF=100:1:1), lysed for 30 minutes on ice, and centrifugated at 12000 rpm at 4° C. for 15 min). Took the supernatant and discarded the sediment. Took an appropriate amount of supernatant to measure the protein concentration by the BCA method. Then added loading buffer at a 5:1 ratio and boiled at 100° C. for 7 minutes to be used for Western Blot experiments or stored in a −80° C. freezer for later use.

Figure 4:
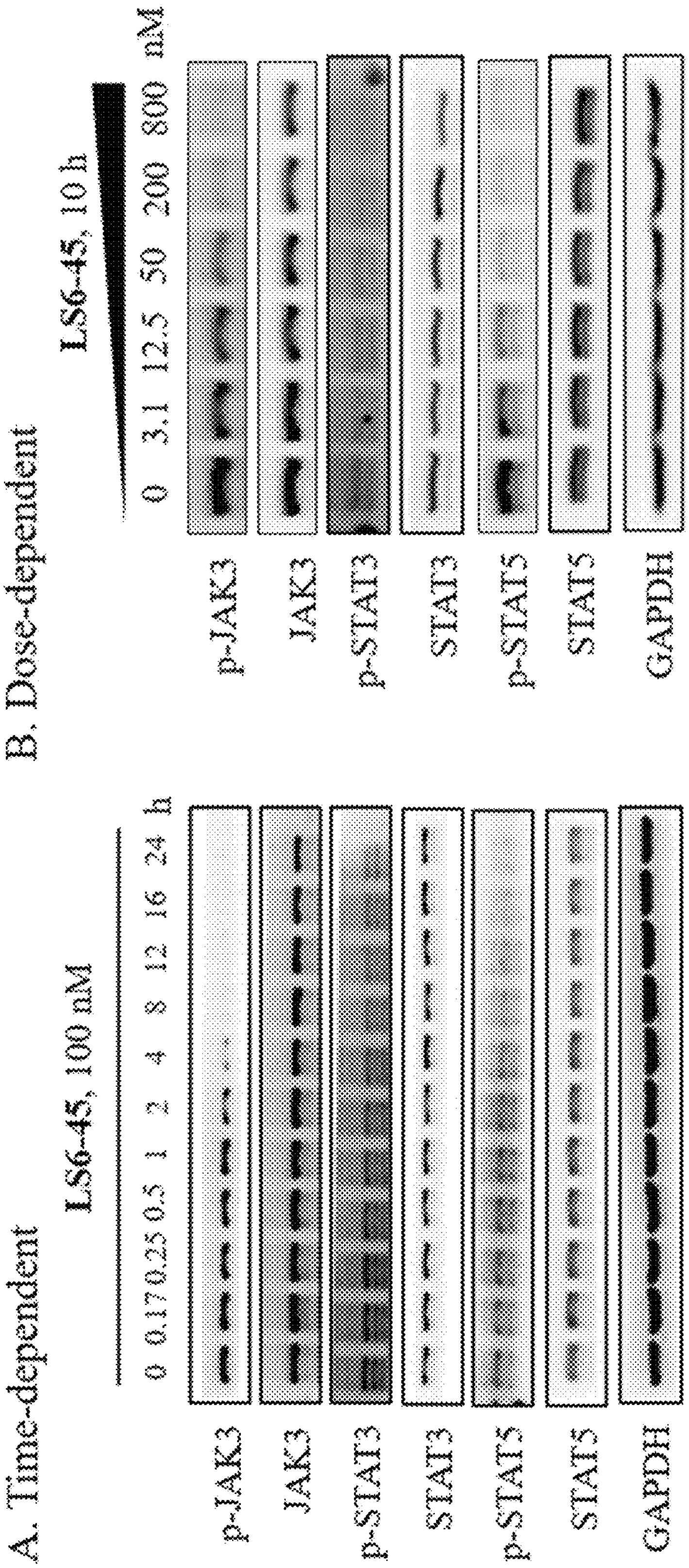
FIG. 4 shows the inhibitory effect of compound LS6-45 on the JAK3 pathway in U937 cells.

The experimental results are shown in FIG. 4, wherein the Western Blot analysis of compound LS6-45 on JAK3, STAT3, STAT5 proteins and their time/dose-dependent phosphorylation was performed, and GAPDH was used as an internal reference. In FIG. 4, A represents the U937 cell line treated with compound LS6-45 (100 nM) in a time-dependent manner, while B represents the U937 cell line treated with compound LS6-45 in a dose-dependent manner for 10 hours (diluted at five concentrations of 800 nM 1:4).

The Western blot experiment results (FIG. 4) showed that compound LS6-45 (100 nM) effectively reduced the phosphorylation level of JAK3 protein after co-incubating with U937 cells for 4 hours, and completely inhibited JAK3 phosphorylation in around 8 hours. At the same time, the phosphorylation levels of downstream proteins STAT3 and STAT5 also weakened in a time-dependent manner (A in FIG. 4). After treating U937 cell line with different concentrations of compound LS6-45 for 10 hours, it was found that the phosphorylation level of JAK3 was significantly weakened at 50 nM, and the phosphorylation level of JAK3 almost completely disappeared at 200 nM, while the phosphorylation levels of downstream proteins STAT3 and STAT5 also showed a dose-dependent weakening (B in FIG. 4). This indicated that the tested molecule LS6-45 can downregulate the JAK3 signaling pathway in U937 cells in time/dose-dependent manner.

Example 50 Wash Out Experiment

Cell line: human acute myeloid leukemia cell line U937

After 200 nM test compound LS6-45 was co-incubated with U937 cells for 10 hours, the supernatant was discarded by centrifugation. The cells were collected and washed with PBS to remove residual compounds. After adding fresh culture medium, the cells continued to be cultured in a 37° C. incubator. Cells were collected at 0, 0.5, 1, 2, 4, 8, 12, and 16 hours, and protein was extracted for Western blot analysis.

Figure 5:
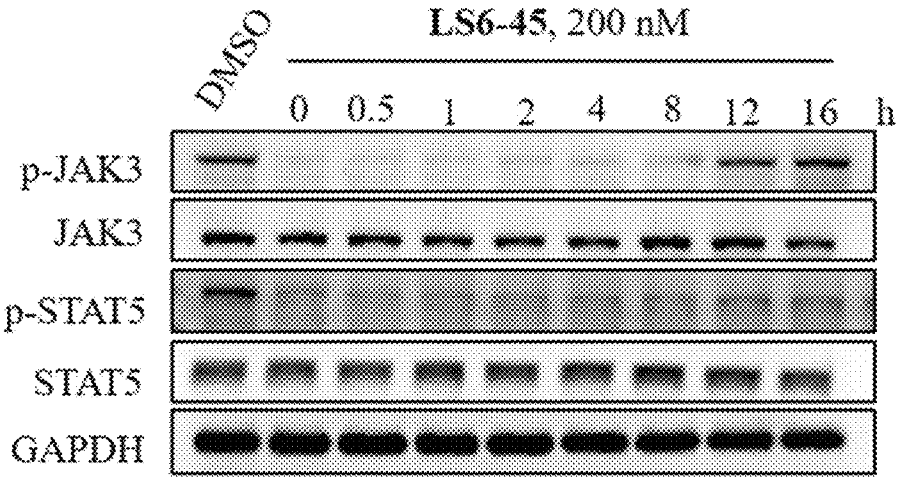
FIG. 5 shows the wash-out results of compound LS6-45.

The results of the wash out assay (FIG. 5) showed that after compound LS6-45 was removed from the culture system, the phosphorylation levels of JAK3 and downstream protein STAT5 in U937 cells were continuously inhibited within 8 hours and slowly recovered between 8-12 hours. This indicated that the tested compound LS6-45 could covalently bind to JAK3 protein and continuously exert kinase inhibitory activity within 8 hours, therefore it is a type of irreversible small molecule inhibitor of JAK3.

Example 51 Mechanism Study on the Inhibition of U937 Cell Proliferation by Compound LS6-45

Cell cycle detection: Took cells in good growth status and adjusted the density to $8\times10^5$ cells/mL, and evenly distributed them into 6-well plates, 2 mL per well. Then the compound was diluted in gradient and added to the cell suspension, and incubated in an incubator for 24 hours. BD Cycletest™ Plus DNA Reagent Kit was used for staining in this experiment. After 24 hours, the cells were collected into a 15 mL centrifuge tube, and the 6-well plate was washed twice with PBS. The washing solutions were merged into a 15 mL centrifuge tube, centrifuged at 12000 rpm for 5 minutes, and the supernatant was discarded. Added 5 mL of buffer solution to each tube and the cells were gently resuspended. Centrifuge: 12000 rpm for 5 minutes, the supernatant was carefully removed and left about 50 μL of liquid without discarding. Added 1.5 mL of buffer solution to each tube to gently resuspend the cells, which were carefully transferred to a 1.5 mL EP tube. Adjusted the cell concentration to $1\times10^6$ cells/mL, to meet the requirements of $5\times10^5$ cells to complete this experiment. Centrifuged at 1200 rpm for 5 minutes, and the supernatant was carefully aspirated. Added 125 μL of Solution A, mixed gently and reacted at room temperature for 10 minutes. Added 100 μL of Solution B, mixed gently and reacted at room temperature for 10 minutes. Added 200 μL of Solution C (PI), mixed gently and reacted in the dark for 10 minutes before detecting by an up-flow cytometry. Note: PI-stained samples needed to be filtered with gauze before being put on the machine; the stained samples are suggested to be placed on ice; the cells should not be over digested and minimize the overall operation time; don't use too many cells. It is enough if a thin layer of cells can be seen at the bottom of the 1.5 mL EP tube after centrifugation.

Cell apoptosis detection: Took cells in good growth status and adjusted the density to $8\times10^5$ cells/mL, evenly distributed them into 6-well plates, 2 mL per well. Then the compound was diluted in gradient and added to the cell suspension, and placed in the incubator for 48 hours. PE coupled Annexin V apoptosis detection kit was used for staining in this experiment. After 48 hours, cells were collected into a 15 mL centrifuge tube, and the 6-well plate was washed twice with PBS. The washing solutions were merged into a 15 mL centrifuge tube, centrifuged at 1200 rpm for 5 minutes, and the supernatant was discarded. The cells were washed with 1.5 mL of cold PBS and resuspended and transferred to a 1.5 mL EP tube. Repeated washing with cold PBS once and after centrifugation at 1200 rpm for 5 minutes, discarded the supernatant. Added 100 μL of 1×Binding Buffer (PBS dilution) to resuspend the cells. Added 2.5 μL of Annexin V-PE and 2.5 μL 7-AAD, mixed gently and reacted at room temperature in the dark for 15 minutes. Added 400 μL of 1× Binding Buffer, and then perform detection with an up-flow cytometry within 1 hour. Note: It is necessary to set up a single label control tube with apoptotic cells, and sample tubes with the same conditions; place the stained samples on ice.

Figure 6:
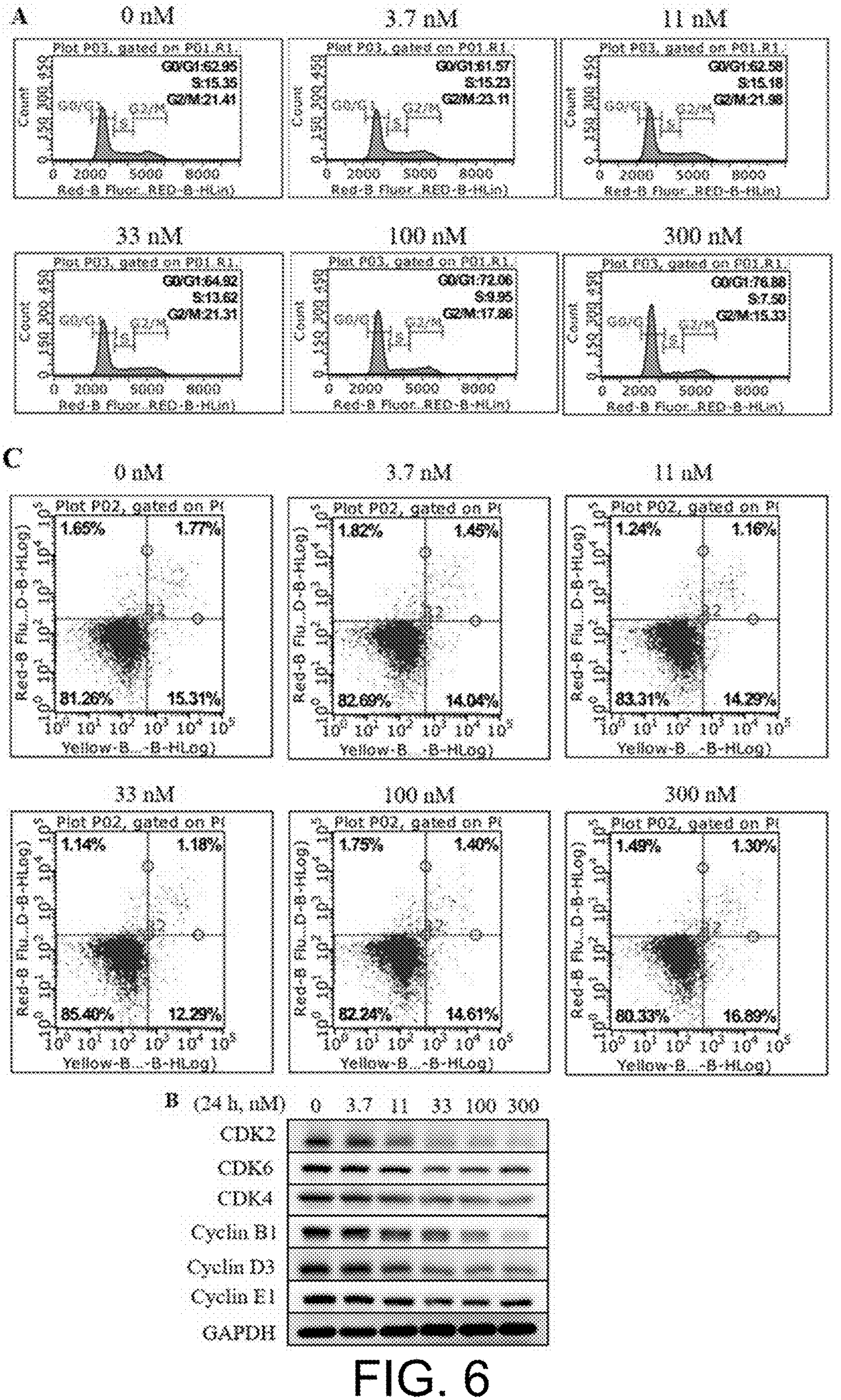
FIG. 6 shows the effect of compound LS6-45 on cell cycle arrest and apoptosis in U937 cells.

FIG. 6 shows the changes in cell cycle (A) and cell cycle related proteins (B) after treating U937 cells with compound LS6-45 for 24 hours, as well as the changes in cell apoptosis of U937 cells treated with compound LS6-45 for 48 hours (C). The results (FIG. 6) showed that U937 had obvious G0/G1 phase block after treatment with compound LS6-45 of different concentrations, and showed a dose-dependent manner (A in FIG. 6); At the same time, cell cycle related proteins (CDK2, CDK4, CDK6, Cyclin B1, Cyclin D3, and Cyclin E1) were also significantly down-regulated after treatment (B in FIG. 6). No apoptosis was observed in U937 cells treated with compound LS6-45 (C in FIG. 6).

Example 52 In Vivo Anti-Tumor Activity of Compound LS6-45 in Mice

This study was conducted in accordance with the "Regulations on the Breeding and Use of Experimental Animals" of Jinan University, and was approved by the Animal Ethics Committee of Jinan University.

Animal model: 4-6 weeks old Male CB-17 SCID mice

U937 cells were cultured in vitro (1640+10% FBS+1% dual antibody) and amplified to 50 plates (10 cm). The cells were collected into a 50 mL centrifuge tube, centrifuged at 800 rpm for 5 minutes. The supernatant was discarded, and the cells was enriched into a 50 mL sterile centrifuge tube, washed once with PBS, and centrifuged at 800 rpm for 5 minutes. The cells were suspended with an appropriate amount of sterile PBS, counted and diluted to $2\times10^7$ cells/mL; 0.2 mL cells per animal were inoculated subcutaneously in the right anterior axilla of the animal (preferably inoculated before the animal is 20 g).

5-7 days after inoculation (Since U937 tumor grows fast, observe once every 3 days), when the tumor grew to 100-200 $mm^3$, the mice were grouped and administered the drugs, and excluded the animals with too large or too small tumors. The mice were randomly divided into a medication group and a solvent group, with 6 mice in each group. The initial tumor volume and body weight were recorded on the day of grouping. Every mouse was orally administrated with 50 mg/kg, 25 mg/kg, and 12.5 mg/kg of medication twice every day (bid), intraperitoneal injection of 10 mg/kg of medication once (qd), and control group was given an equal volume of solvent.

The administration cycle was 10 days, and daily administration was applied. The body weight and tumor volume of animals were measured once every 2 days. The formula for calculating tumor volume is: $V=\pi/6*a*b*b$ (wherein a and b are the length and width of the tumor, respectively). The next day after the end of administration, the animal was weighed and the tumor volume was measured; and then the animal was sacrificed and the tumor was dissected to weighed. The tumor body was fixed with neutral formalin for pathological observation. Animal blood samples were collected for routine blood analysis according to experimental needs, and the main organs of the animals were collected for pathological analysis. At the end of the study, all animals were euthanized and the tumors, livers, kidneys, and lungs of nude mice were collected for further analysis.

Figure 7:
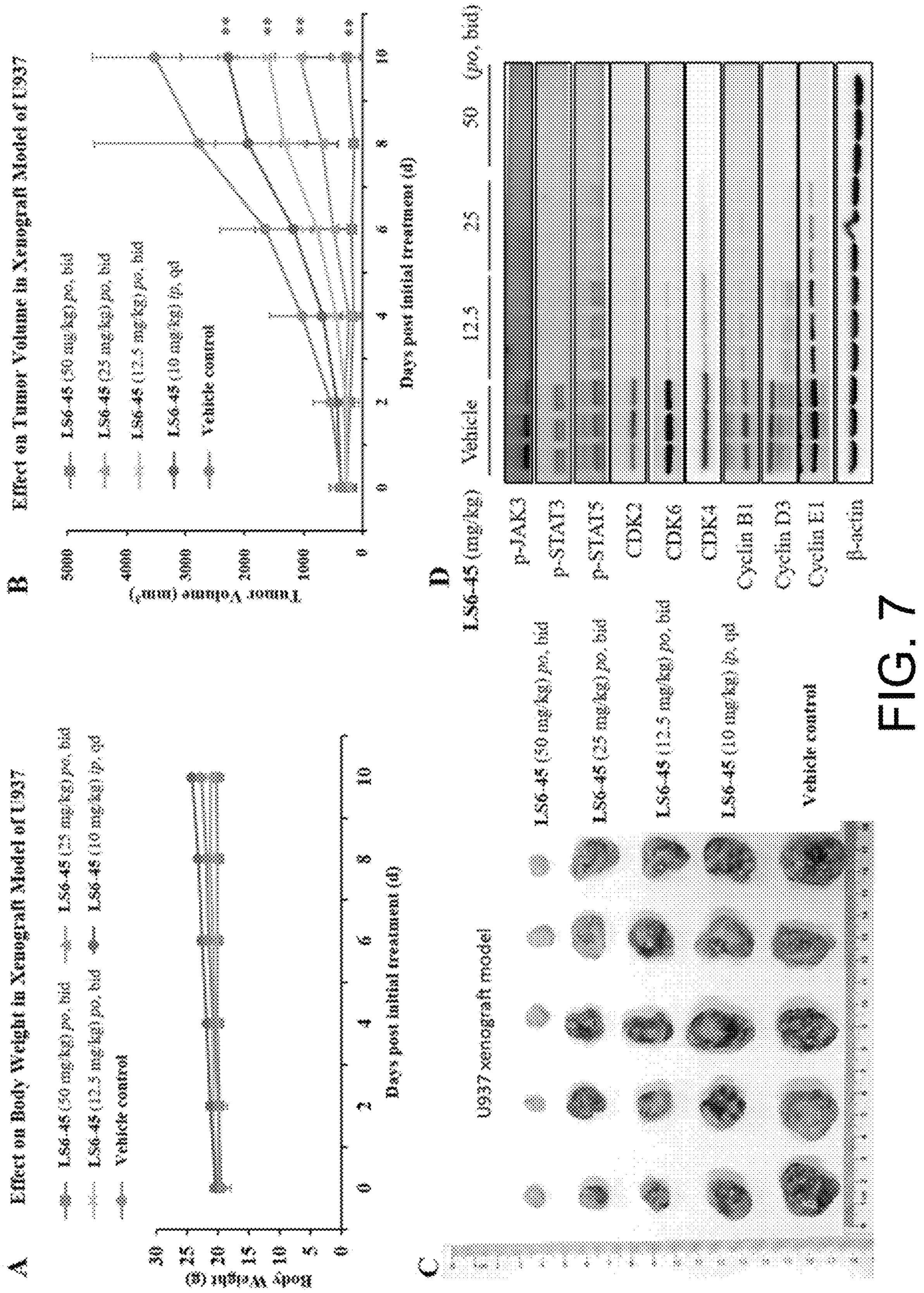
FIG. 7 shows the in vivo anti-tumor activity results of the compound LS6-45 in mice.

The experimental results are shown in FIG. 7, wherein A represents the body weight change curve of mice in each group; B represents the tumor volume growth curve of mice in each dose group; C represents the tumor size of each treatment group at the end of the experiment; D represents the activation level of JAK3 pathway and changes in cycle related proteins in tumor tissues of each treatment group. ** $p<0.01$.

The in vivo activity results (FIG. 7) showed that the growth rate of tumors during administration was significantly lower than that of the control group, and among them, the tumor growth of the 50 mg/kg dose group was completely stagnant or even regressed (B/C in FIG. 7). During the administration period, there were no toxic side effects and no signs of weight loss (A in FIG. 7). Western blot analysis was performed on tumor tissues of experimental mice. Compared with the control group, compound LS6-45 showed significant inhibitory effects on the phosphorylation of JAK3, STAT3, and STAT5, and cell cycle related proteins (D in FIG. 7). This indicated that the tested compound had good in vivo anti-tumor activity.

The technical features of the examples above can be combined arbitrarily. To simplify description, all possible combinations of the technical features of the examples above are not described. However, as long as there is no contradiction in the combination of these technical features, they should be considered as falling within the scope of this specification.

The examples above only express several implementations of the present disclosure. The descriptions of the examples are relatively specific and detailed, but may not be construed as the limitation on the patent scope of the present disclosure. It should be noted that a person of ordinary skill in the art may make several variations and improvements without departing from the concept of the present disclosure. These variations and improvements all fall within the protection scope of the present disclosure. Therefore, the patent protection scope of the present disclosure shall be defined by the appended claims.

What is claimed is:

1. 2-aminopyrimidine compounds with the structure shown in Formula (I) or their pharmaceutically acceptable salts, solvates, or their stereoisomers, geometric isomers, tautomers:

(I)

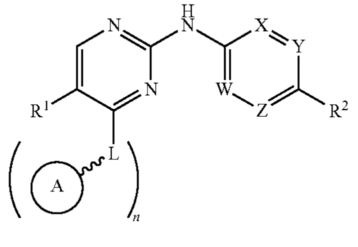

wherein, $R^1$ is selected from: H, halogen, cyano, a $C_1$-$C_6$ alkyl group optionally substituted with one or more $R^{11}$ groups, a $C_3$-$C_6$ cycloalkyl group optionally substituted with one or more $R^1$ groups, a $C_1$-$C_6$ alkoxy group optionally substituted with one or more $R^{11}$ groups, a $C_3$-$C_6$ cycloalkoxy group optionally substituted with one or more $R^{11}$ groups, —NH—C(═O)H;

$R^2$ is selected from: H, halogen, —$(CH_2)_m NR^3R^4$, —$(CH_2)_m CR^3R^4R^5$ or —$(CH_2)_m OCR^3R^4R^5$; wherein, each m is independently 0, 1, 2, or 3; each $R^3$ and each $R^4$ are independently selected from: (i) H, or one or more $R^{12}$ substituted $C_1$-$C_6$ alkyl groups; and (ii) $R^3$ and $R^4$, together with the attached N or C, may form a 3-12 membered single ring, fused ring, bridge ring, or spiral ring containing 0-3 heteroatoms and optionally substituted with one or more $R^{12}$ groups; $R^5$ is selected from: H, cyano or $C_1$-$C_3$ alkyl; each $R^{12}$ is independently selected from: H, halogen, hydroxyl, amino, $C_1$-$C_3$ alkyl, $C_1$-$C_3$ alkyl substituted by —C(═O)NHR$^{13}$, hydroxy substituted $C_1$-$C_3$ alkyl, $C_1$-$C_3$ alkyl substituted by $C_3$-$C_6$ cycloalkyl group, $C_3$-$C_8$ heterocyclic group substituted $C_1$-$C_3$ alkyl group, $C_1$-$C_3$ alkoxy, —NHR$^{13}$, —N(R$^{13}$)$_2$, —C(═O)R$^{13}$, $R^{13}$ substituted or unsubstituted 4-8-membered single ring, fused ring, bridge ring, or spiral ring containing 0, 1, 2, or 3 heteroatoms; $R^{13}$ is a $C_1$-$C_3$ alkyl group; the heteroatom is O, S, and/or N;

W, X, Y, and Z are independently N or —CR$^6$; wherein, $R^6$ is selected from: hydrogen, halogen, a $C_1$-$C_3$ alkyl group optionally substituted with one or more $R^{11}$ groups, a $C_1$-$C_3$ alkoxy group optionally substituted with one or more $R^{11}$ groups, —NH—CN, —NHC(O)—CR$^7$═CR$^8$R$^9$, —NHS(O)$_2$—CR$^7$=CR$^8$R$^9$; $R^7$, $R^8$, and $R^9$ are independently selected from: H, cyano, a $C_1$-$C_6$ alkyl group optionally substituted with one or more $R^{11}$ groups;

n is 1;

L is 0 or S;

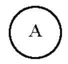

is a 8-10 membered saturated or partially saturated fused double ring containing 1, 2, or 3 oxygen atoms and optionally substituted with one or more $R^{10}$ groups; wherein, each $R^{10}$ is independently selected from: hydrogen, halogen, hydroxyl, a $C_1$-$C_3$ alkyl group optionally substituted with one or more $R^{11}$ groups, a $C_1$-$C_3$ alkoxy group optionally substituted with one or more $R^{11}$ groups, $R^{11}$ is selected from: halogen, hydroxyl, amino, $C_1$-$C_3$ alkyl, $C_1$-$C_3$ alkoxy, —$NHR^{13}$, —N $(R^{13})_2$, —C(=O) $R^3$.

2. The 2-aminopyrimidine compounds or their pharmaceutically acceptable salts, solvates, or their stereoisomers, geometric isomers, tautomers according to claim 1, wherein

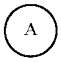

is selected from the group consisting of the following structures:

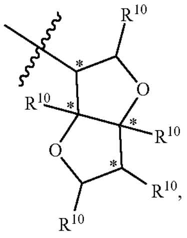

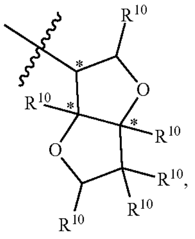

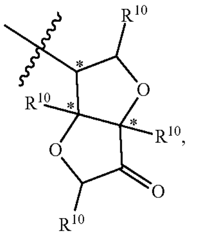

and

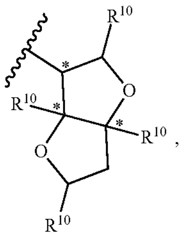

wherein, the configurations of chiral carbon atoms labeled with * are independently S or R configurations.

3. The 2-aminopyrimidine compounds or their pharmaceutically acceptable salts, solvates, or their stereoisomers, geometric isomers, tautomers according to claim 2, wherein

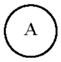

is selected from the group consisting of the following structures:

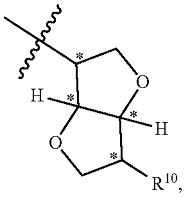

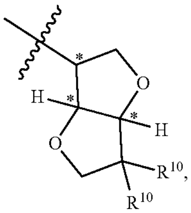

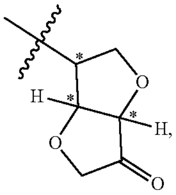

and

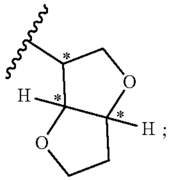

wherein, the configurations of chiral carbon atoms labeled with * are independently S or R configurations, and each $R^{10}$ is independently selected from: halogen, hydroxyl, $C_1$-$C_3$ alkyl, $C_1$-$C_3$ alkoxy.

4. The 2-aminopyrimidine compounds or their pharmaceutically acceptable salts, solvates, or their stereoisomers, geometric isomers, tautomers according to claim 3, wherein

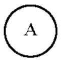

is selected from the group consisting of the following structures:

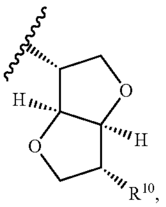

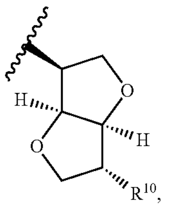

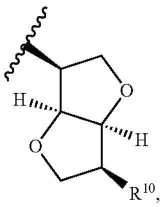

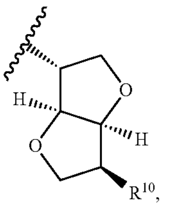

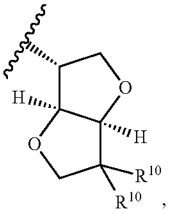

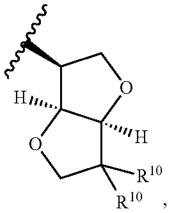

-continued

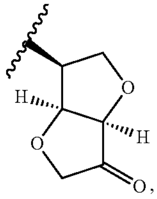, 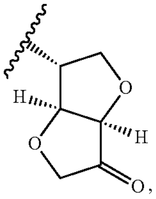, 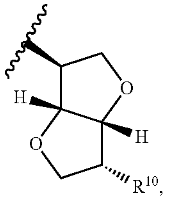, 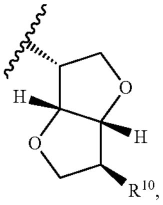, 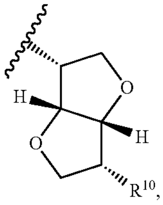, 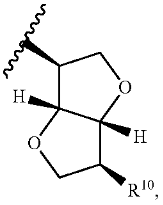, 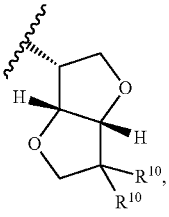, 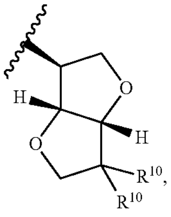, 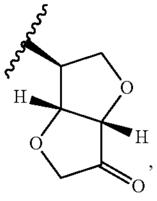, 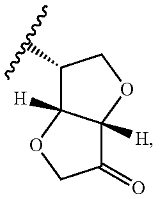, 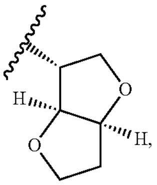, 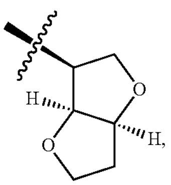, 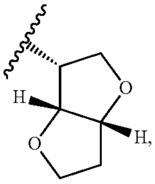, and 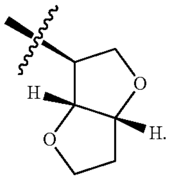.

5. The 2-aminopyrimidine compounds or their pharmaceutically acceptable salts, solvates, or their stereoisomers, geometric isomers, tautomers according to claim 4, wherein

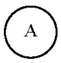

is selected from the group consisting of the following structures:

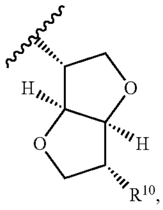, 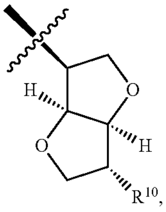, 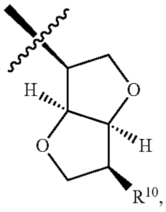,

-continued

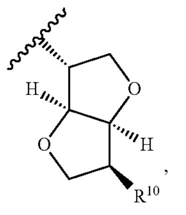, 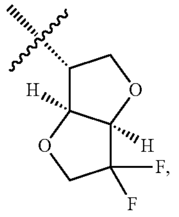, 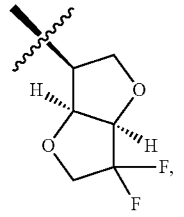, 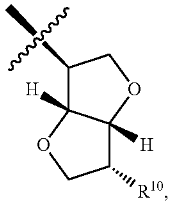, 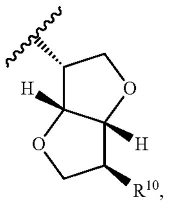, 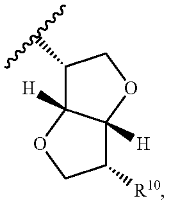, 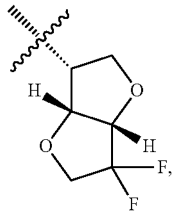, 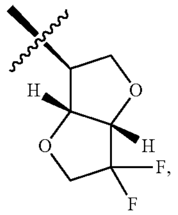, 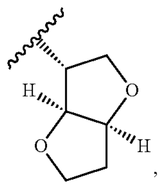, 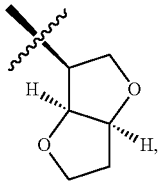, 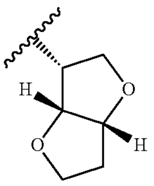 and 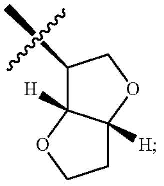;

wherein, each $R^{10}$ is independently selected from: F, hydroxyl, methyl, methoxy, ethoxy, and isopropoxy.

6. The 2-aminopyrimidine compounds or their pharmaceutically acceptable salts, solvates, or their stereoisomers, geometric isomers, tautomers according to claim 5, wherein

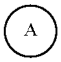

is selected from the group consisting of the following structures:

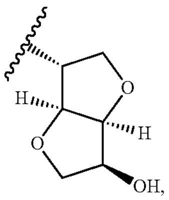, 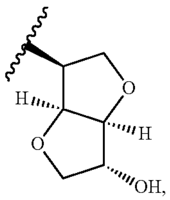, 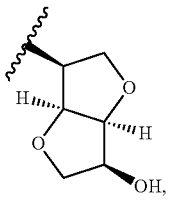, 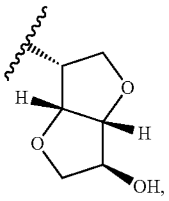, 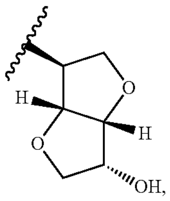, 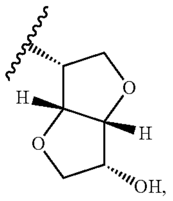,

-continued
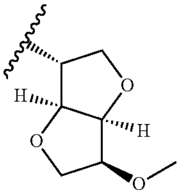,
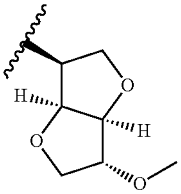,
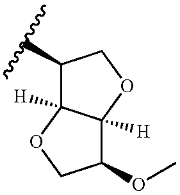,
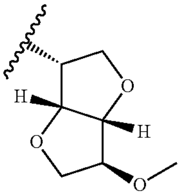,
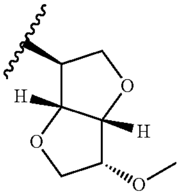,
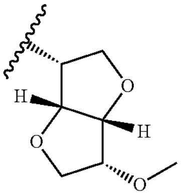,
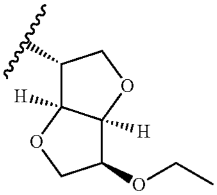,
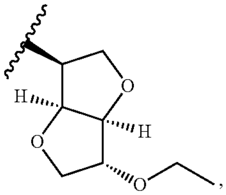,
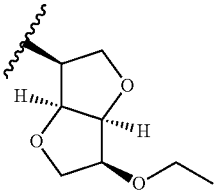,
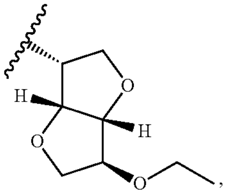,
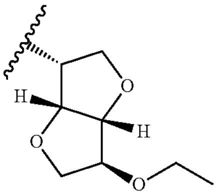,
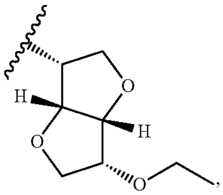,
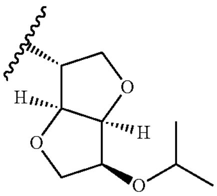,
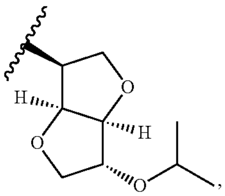,
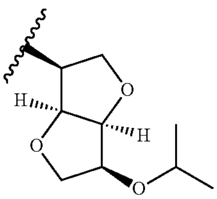,
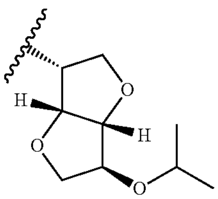,
-continued
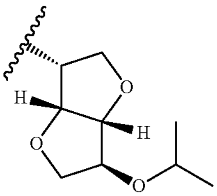,
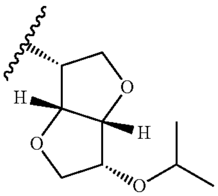,
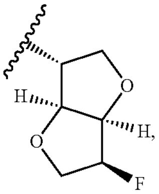
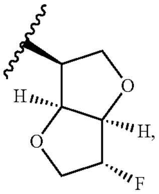
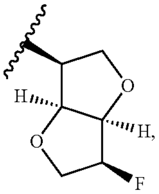
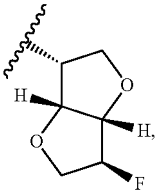
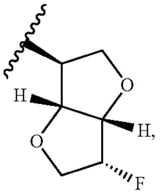
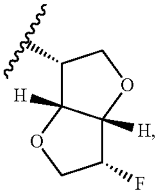
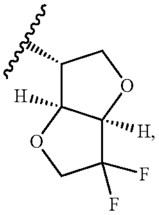
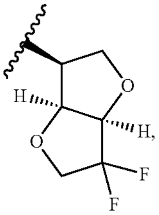
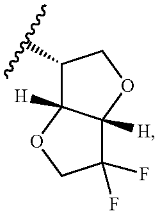
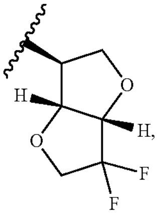
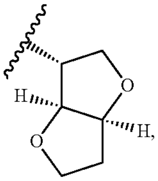
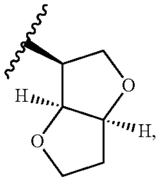
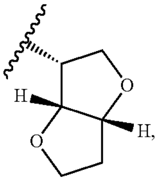
and
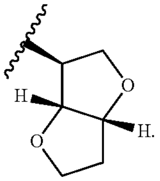
7. The 2-aminopyrimidine compounds or their pharmaceutically acceptable salts, solvates, or their stereoisomers, geometric isomers, tautomers according to claim 1, wherein $R^6$ is selected from: hydrogen, halogen, $C_1$-$C_3$ alkyl group, $C_1$-$C_3$ alkoxy group, —NH—CN,
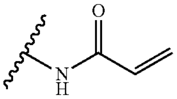,
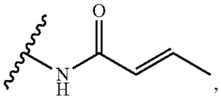,
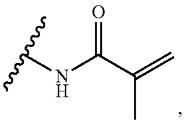,
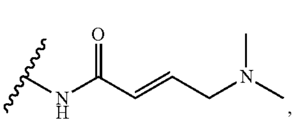, -continued

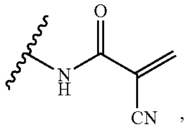

, or

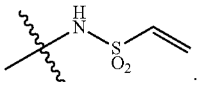

.

8. The 2-aminopyrimidine compounds or their pharmaceutically acceptable salts, solvates, or their stereoisomers, geometric isomers, tautomers according to claim 1, wherein W,X are both CH; Y and Z are independently selected from N or $CR^6$ respectively, wherein, $R^6$ is selected from: hydrogen, halogen, $C_1$-$C_3$ alkyl, $C_1$-$C_3$ alkoxy, —NH—CN,

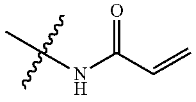

,

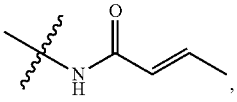

,

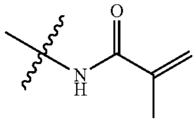

,

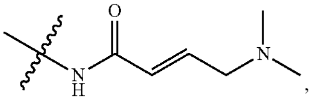

,

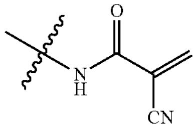

, or

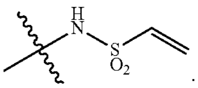

.

9. The 2-aminopyrimidine compounds or their pharmaceutically acceptable salts, solvates, or their stereoisomers, geometric isomers, tautomers according to claim 8, wherein W, X are both CH; Y is $CR^6$, wherein, $R^6$ is selected from: hydrogen, halogen, $C_1$-$C_3$ alkyl, $C_1$-$C_3$ alkoxy,

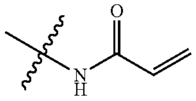

,

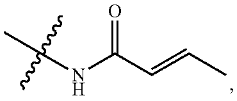

,

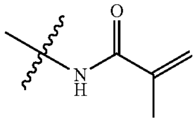

, or

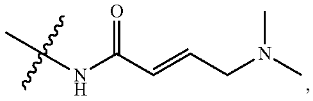

, and Z is CH or N.

10. The 2-aminopyrimidine compounds or their pharmaceutically acceptable salts, solvates, or their stereoisomers, geometric isomers, tautomers according to claim 9, wherein W, X and Z are all CH; Y is $CR^6$, wherein $R^6$ is

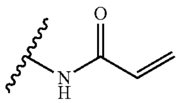

.

11. The 2-aminopyrimidine compounds or their pharmaceutically acceptable salts, solvates, or their stereoisomers, geometric isomers, tautomers according to claim 1, wherein $R^2$ is selected from: H, halogen, $—(CH_2)_mNR^3R^4$, or $—(CH_2)_mCR^3R^4R^5$; wherein, each m is independently 0, 1, 2, or 3;

each $R^3$ and each $R^4$ are independently selected from: (i) H, or one or more $R^{12}$ substituted $C_1$-$C_3$ alkyl groups; and (ii) $R^3$ and $R^4$, together with the attached N or C, may form a 5-11 membered single ring, fused ring, bridge ring, or spiral ring containing 0-3 heteroatoms and optionally substituted with one or more $R^{12}$ groups;

$R^5$ is selected from: H, cyano or $C_1$-$C_3$ alkyl;

each $R^{12}$ is independently selected from: H, hydroxyl, acetyl, $R^{13}$ substituted or unsubstituted 4-8-membered heterocyclic groups, halogens, hydroxyl, amino, $C_1$-$C_3$ alkyl, $C_1$-$C_3$ alkoxy, $—NHR^{13}$, or $—N(R^{13})_2$; $R^{13}$ is a $C_1$-$C_3$ alkyl group.

12. The 2-aminopyrimidine compounds or their pharmaceutically acceptable salts, solvates, or their stereoisomers, geometric isomers, tautomers according to claim 11, wherein $R^2$ is selected from: H, halogen, $—(CH_2)_mNR^3R^4$, or $—(CH_2)_mCR^3R^4R^5$; wherein, each m is independently 0 or 1;

each $R^3$ and each $R^4$ are independently selected from: (i) H, $C_1$-$C_3$ alkyl, hydroxy substituted $C_1$-$C_3$ alkyl, $—NHR^{13}$ substituted $C_1$-$C_3$ alkyl, or $—N(R^{13})_2$ substituted $C_1$-$C_3$ alkyl; and (ii) $R^3$ and $R^4$, together with the attached N or C, may form a 5-11 membered single ring, fused ring, bridge ring, or spiral ring containing 0-3 heteroatoms and optionally substituted with one or more $R^{12}$ groups;

$R^5$ is selected from: H, cyano or $C_1$-$C_3$ alkyl;

each $R^{12}$ is independently selected from: H, hydroxyl, acetyl, $R^{13}$ substituted piperazinyl, $C_1$-$C_3$ alkyl, $—NHR^{13}$, or $—N(R^{13})_2$; $R^{13}$ is a $C_1$-$C_3$ alkyl.

13. The 2-aminopyrimidine compounds or their pharmaceutically acceptable salts, solvates, or their stereoisomers, geometric isomers, tautomers according to claim 1, wherein $R^2$ is selected from: H, halogen,

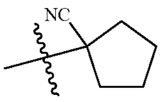

,

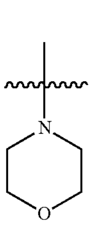

,

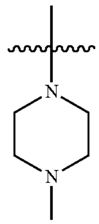

,

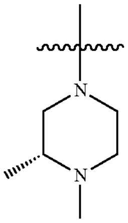

,

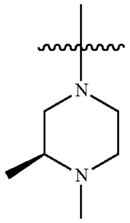

,

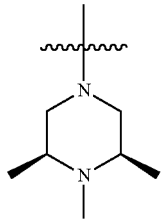

,

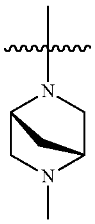

,

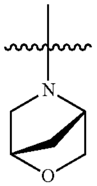

,

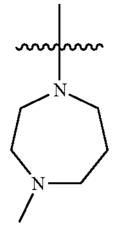

,

-continued

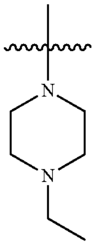 ,
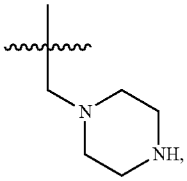 ,
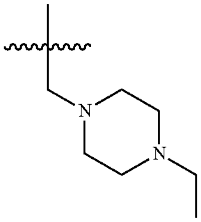 ,
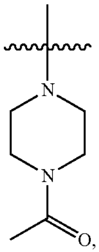 ,
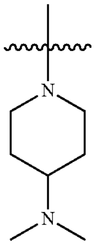 ,
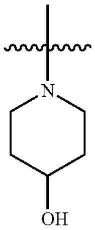 ,
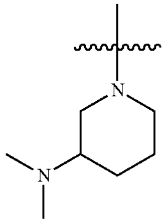 ,
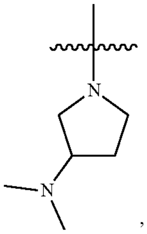 ,
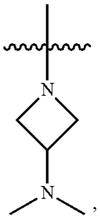 ,
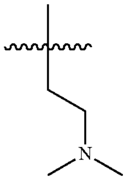 ,
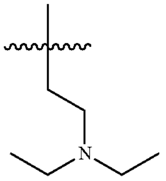 ,
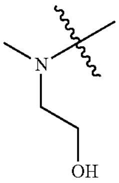 ,
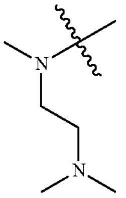 ,
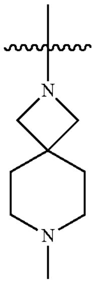 ,
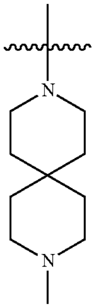 ,
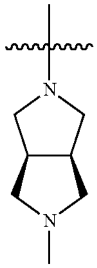 , -continued

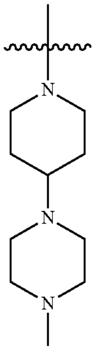 ,
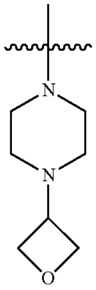 ,
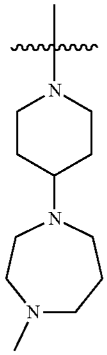 ,
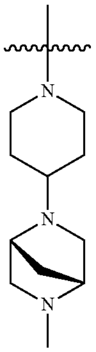 ,
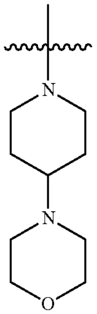 ,
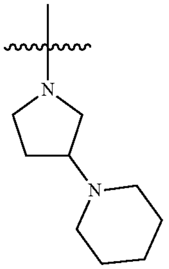 ,
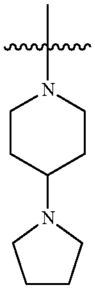 , or

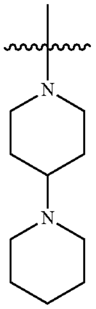 .

14. The 2-aminopyrimidine compounds or their pharmaceutically acceptable salts, solvates, or their stereoisomers, geometric isomers, tautomers according to claim 1, wherein $R^1$ is selected from: H, halogen, cyano, —NH—C(═O)H, $C_1$-$C_6$ alkyl group, $C_1$-$C_6$ alkoxy group, $C_3$-$C_6$ cycloalkyl group, $C_3$-$C_6$ cycloalkoxy group, halogenated $C_1$-$C_6$ alkyl group, or $C_1$-$C_6$ haloalkoxy group.

15. The 2-aminopyrimidine compounds or their pharmaceutically acceptable salts, solvates, or their stereoisomers, geometric isomers, tautomers according to claim 14, wherein $R^1$ is selected from: H, halogen, $C_1$-$C_3$ alkyl, or $C_1$-$C_3$ alkoxy.

16. The 2-aminopyrimidine compounds or their pharmaceutically acceptable salts, solvates, or their stereoisomers, geometric isomers, tautomers according to claim 1, wherein, $R^1$ is selected from: H, halogen, methyl, cyano, —NH—C(═O)H, trifluoromethyl, difluoromethyl, methoxy, cyclopropyl, or trifluoromethoxy.

17. The 2-aminopyrimidine compounds or their pharmaceutically acceptable salts, solvates, or their stereoisomers, geometric isomers, tautomers according to claim 1, wherein it has the structure shown in Formula (II) as follows:

(II)

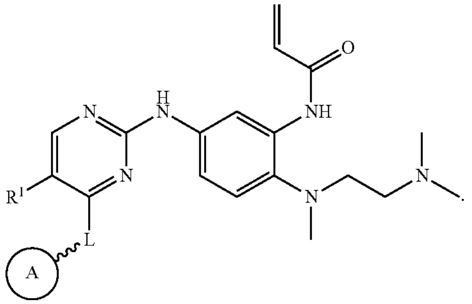

18. The 2-aminopyrimidine compounds or their pharmaceutically acceptable salts, solvates, or their stereoisomers, geometric isomers, tautomers according to claim 1, wherein the 2-aminopyrimidine compound is selected from:

LS 3-96

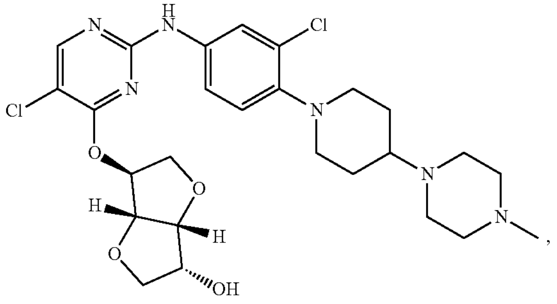

LS 4-97

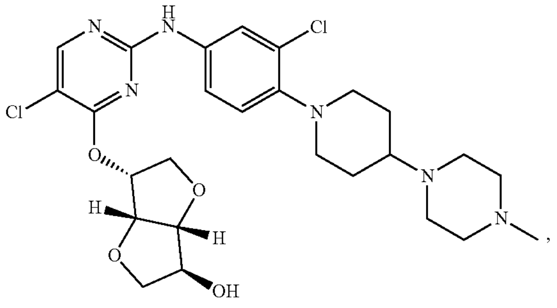

-continued

LS 4-104

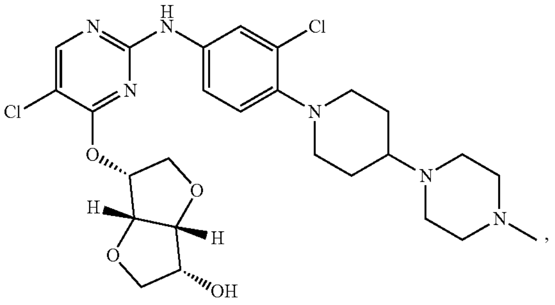

LS 4-100

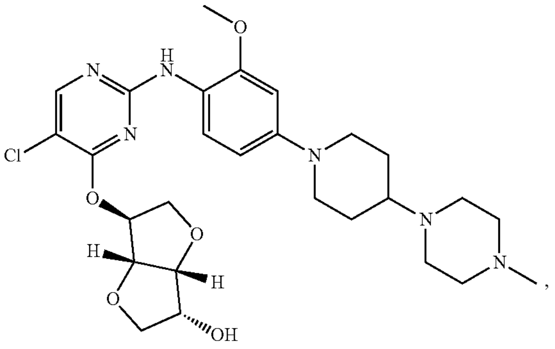

LS 4-106

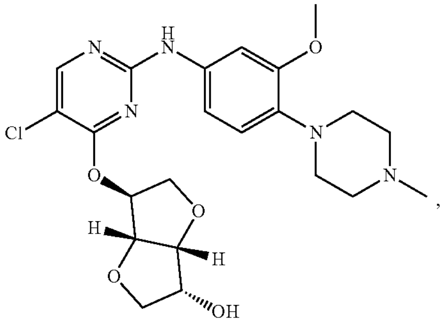

LS 5-58

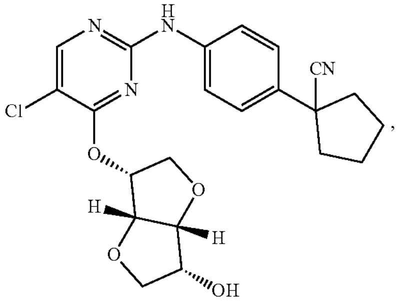

LS 4-144

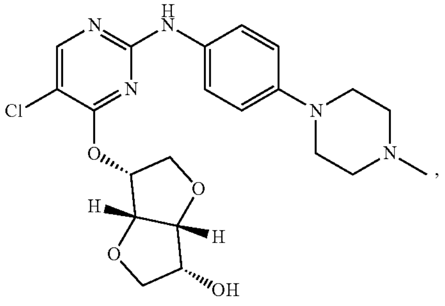

LS 4-142
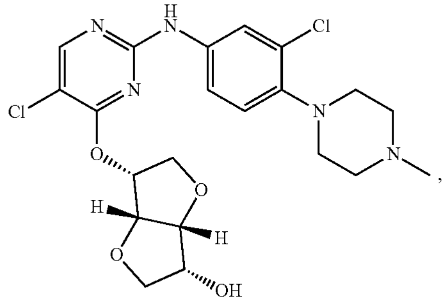
LS 4-145
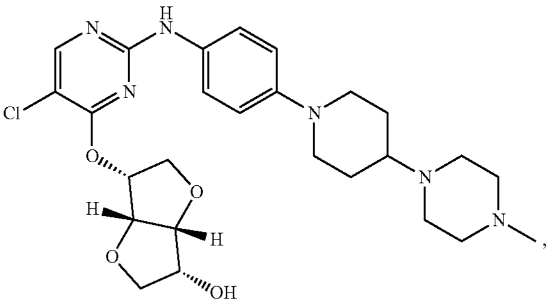
LS 4-143
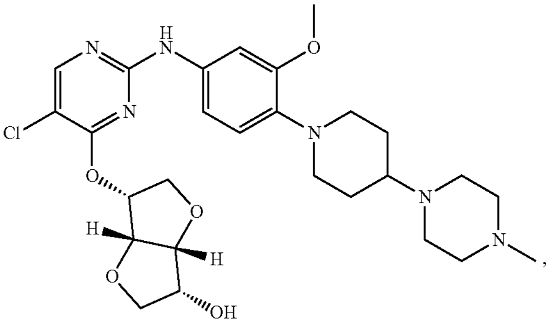
LS 4-148
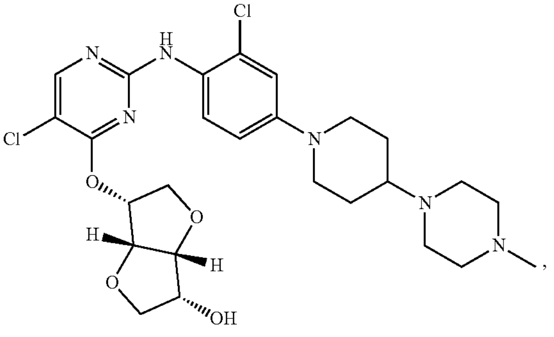
LS 5-16
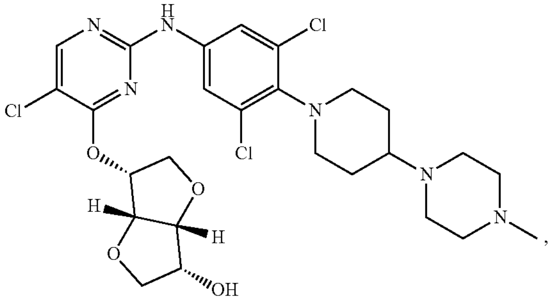
LS 4-150
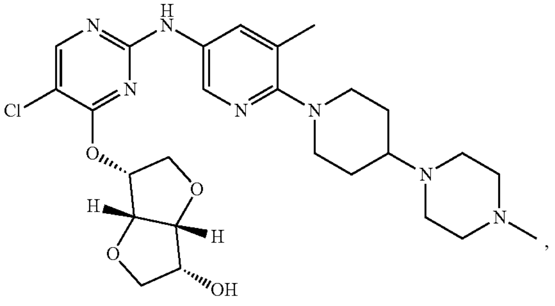
LS 5-54
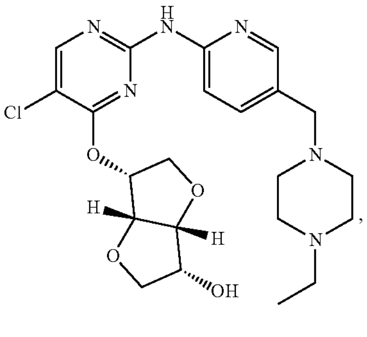
LS 5-3
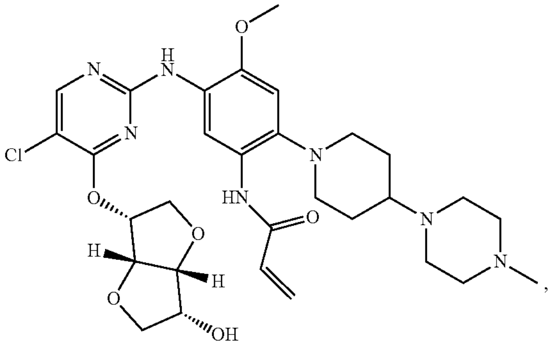

-continued
LS 5-12
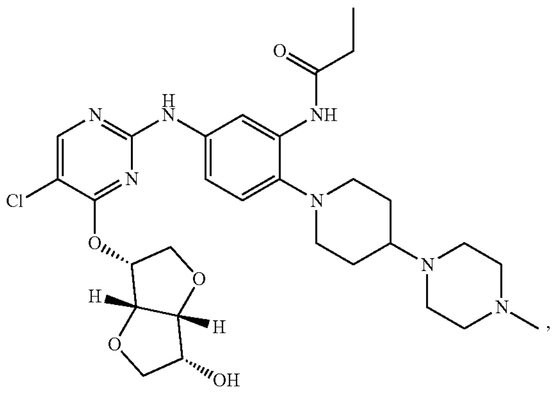
LS 5-77
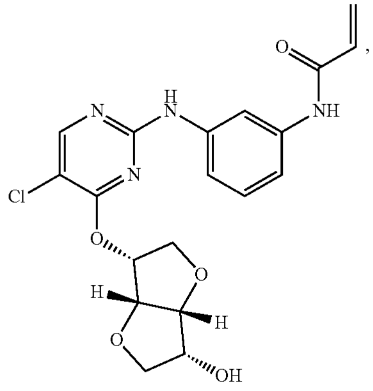
LS 5-62
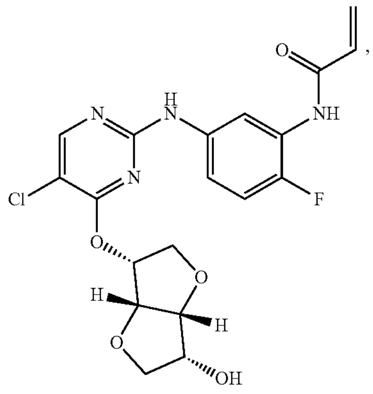
LS 5-66
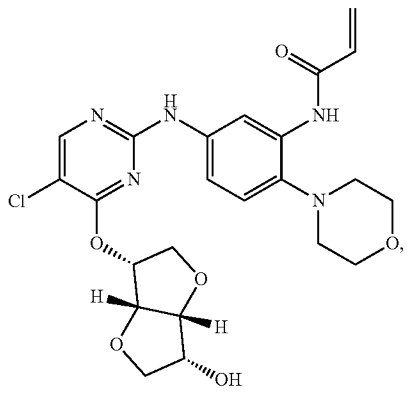
-continued
LS 5-74
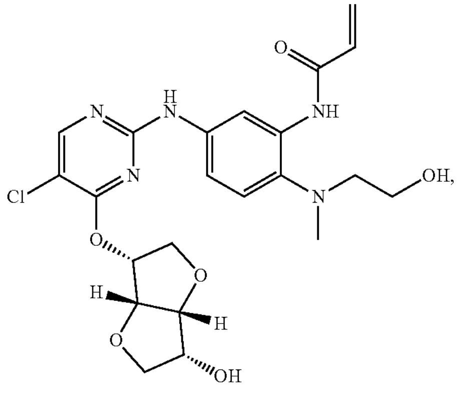
LS 5-72
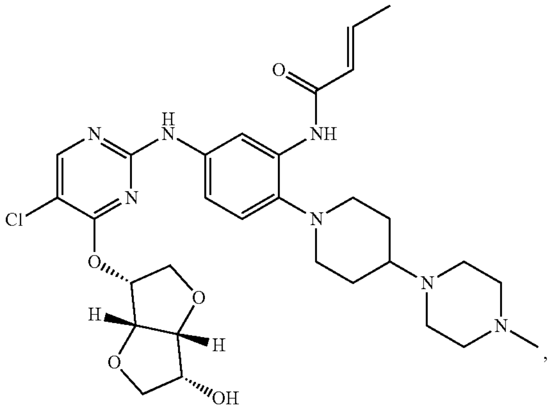
LS 5-73
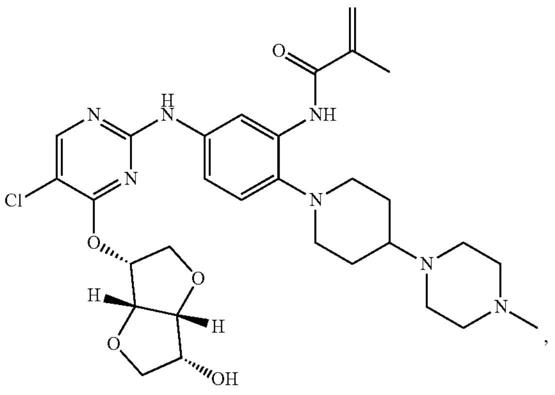

-continued
LS 5-81
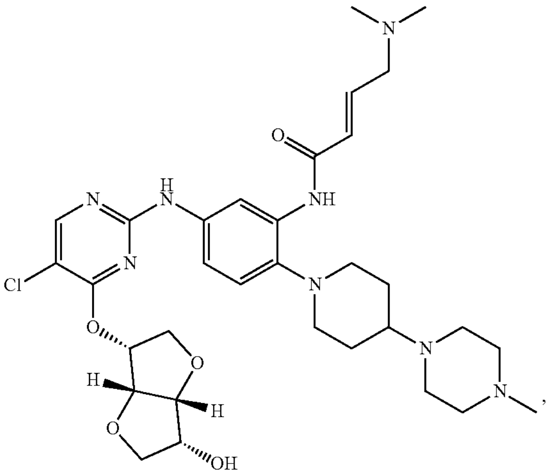
LS 5-88
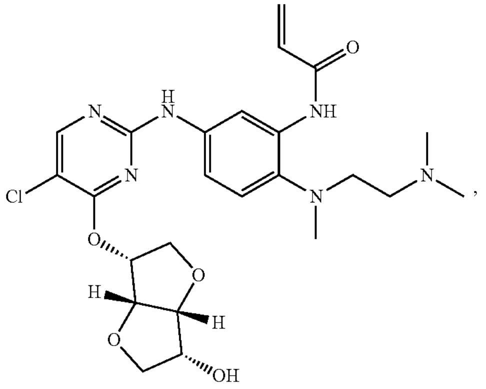
LS 5-91
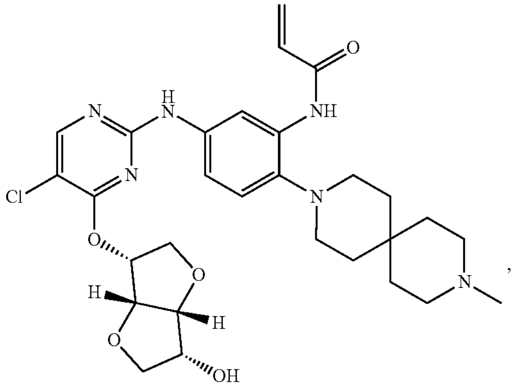
-continued
LS 5-102
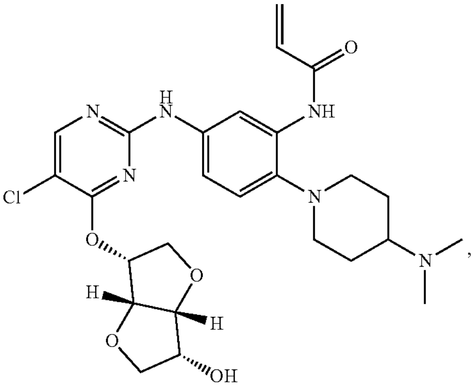
LS5-133
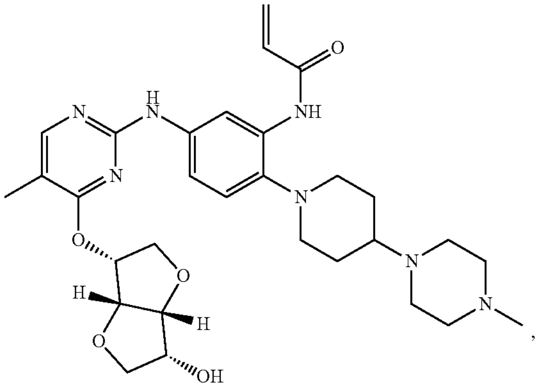
LS5-143
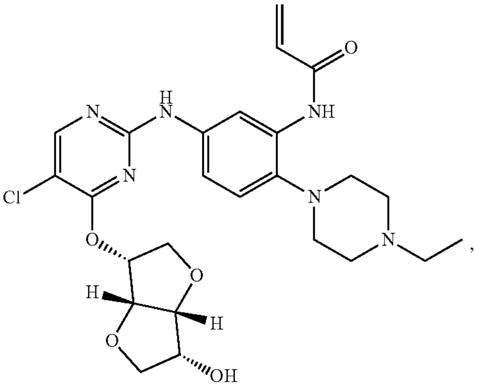
LS5-150
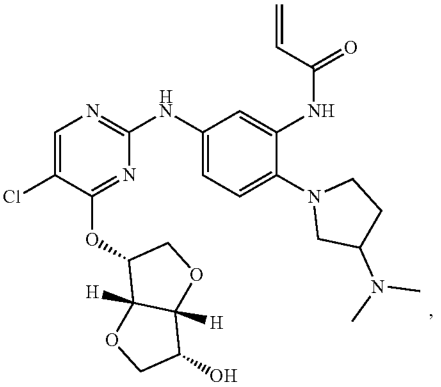

-continued
LS5-152
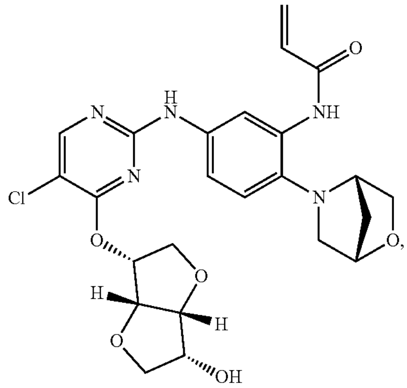
LS5-154
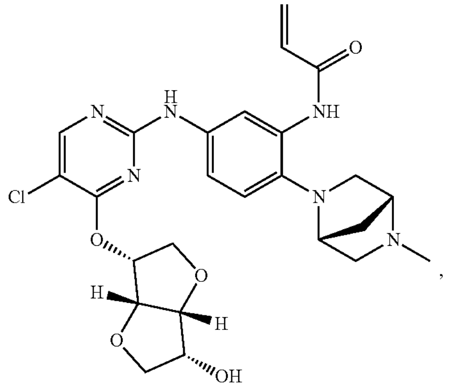
LS 6-16
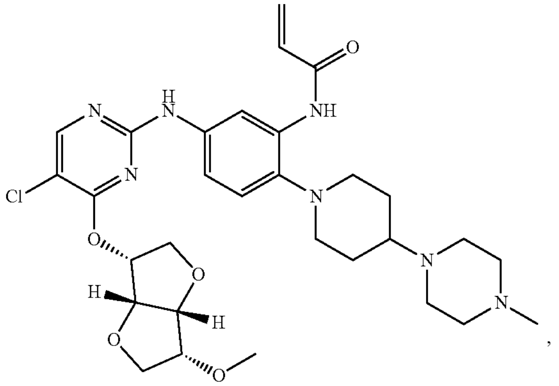
LS 6-45
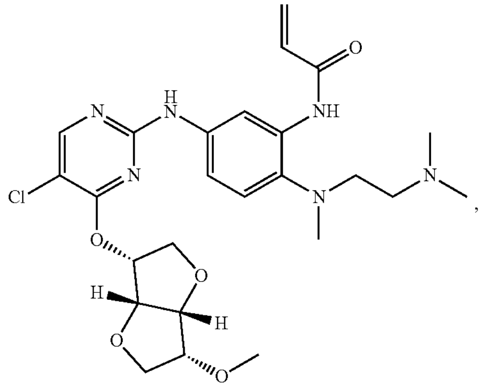
-continued
LS 6-48
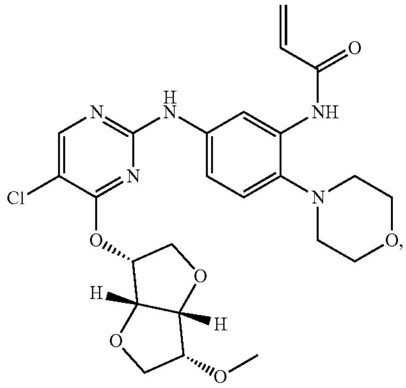
LS 6-49
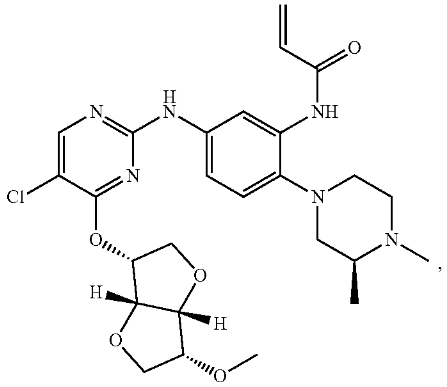
LS 6-59
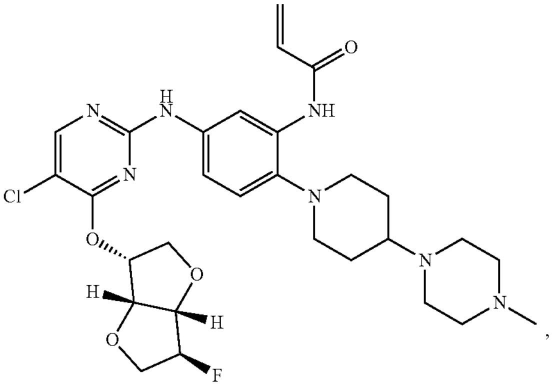
LS 6-77
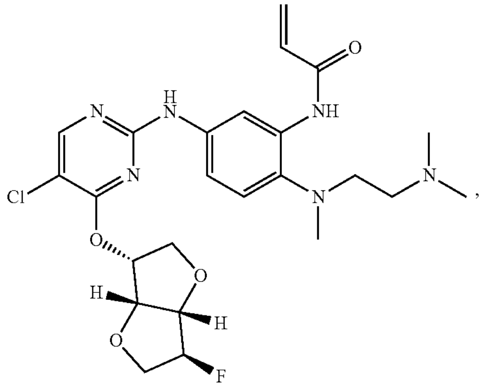

-continued
LS 6-78
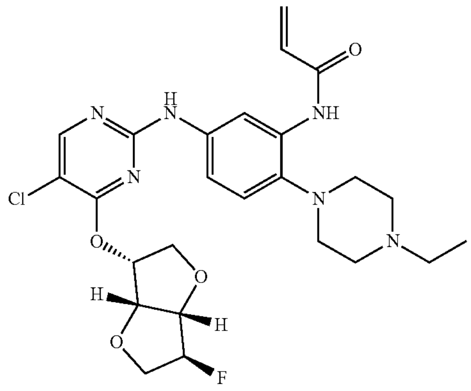
,
LS 6-88
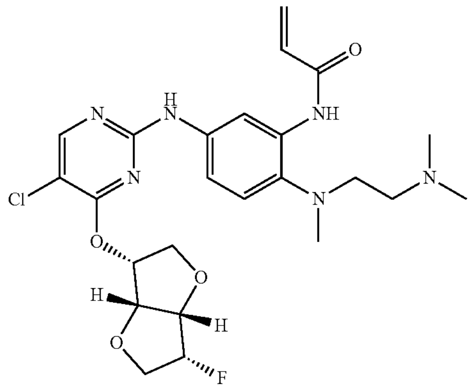
,
LS 6-89
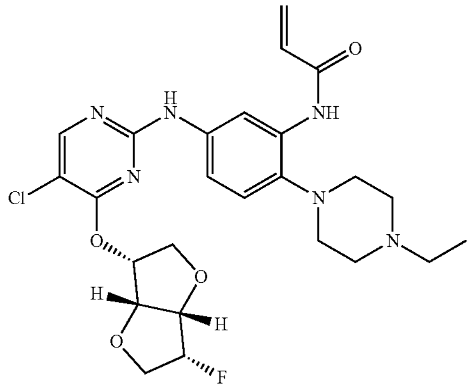
,
LS 6-105
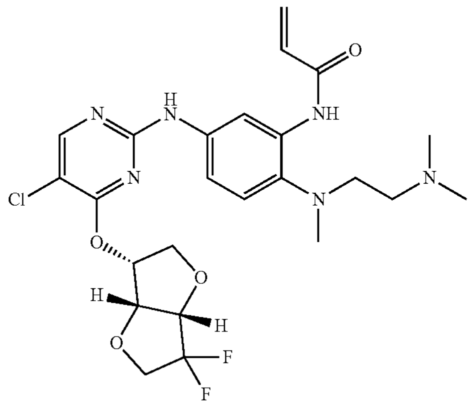
,
-continued
LS 6-121
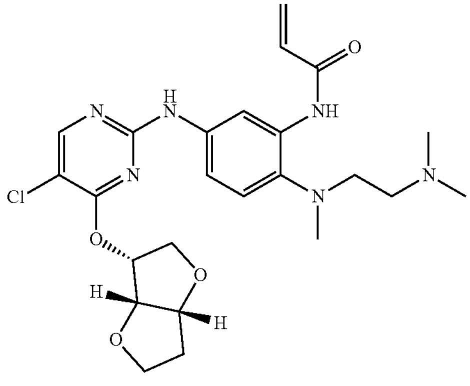
,
LS 7-13
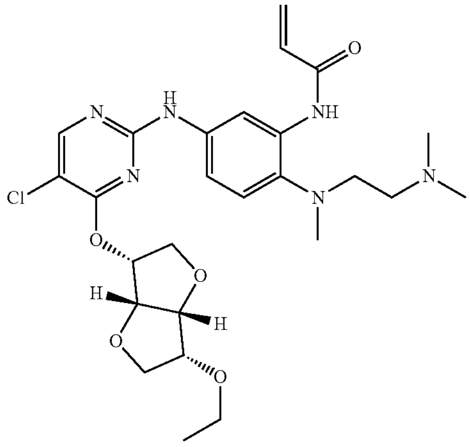
,
LS 7-18
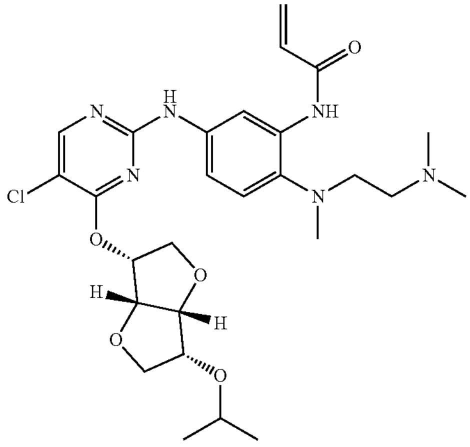
, -continued
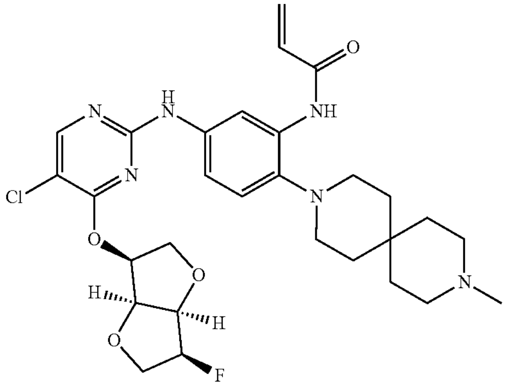
,
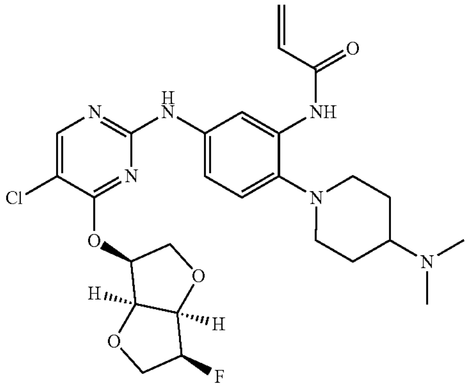
,
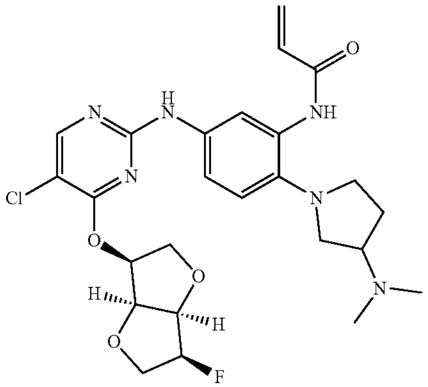
,
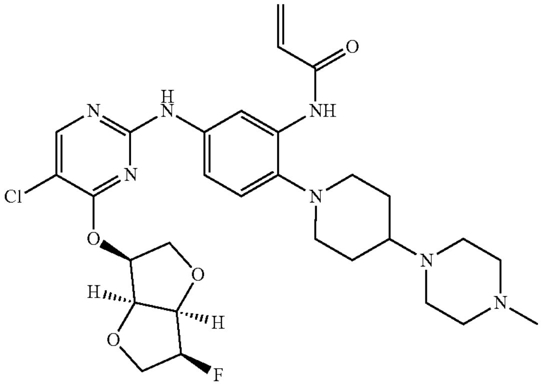
,
-continued
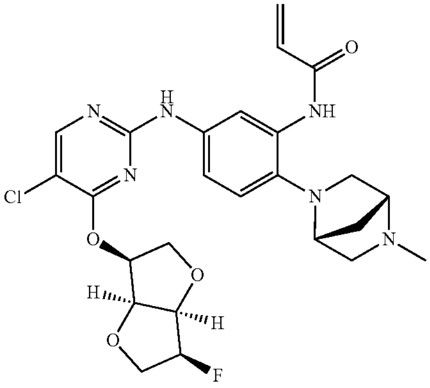
,
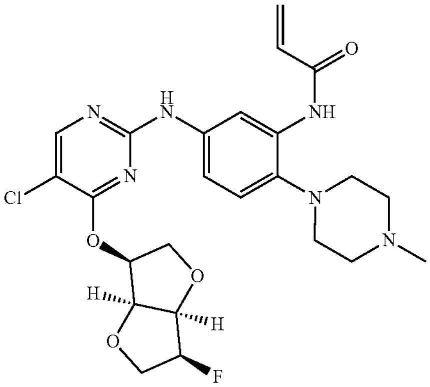
,
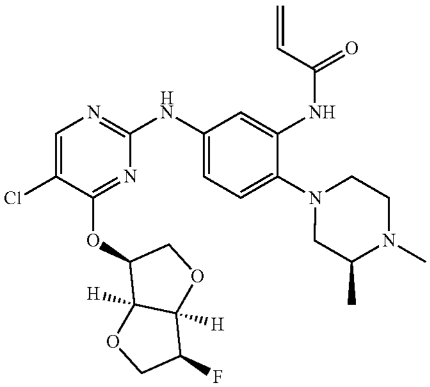
,
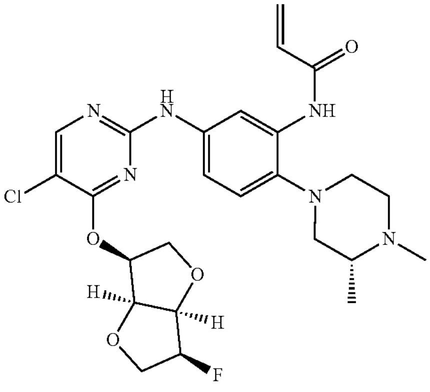
, -continued
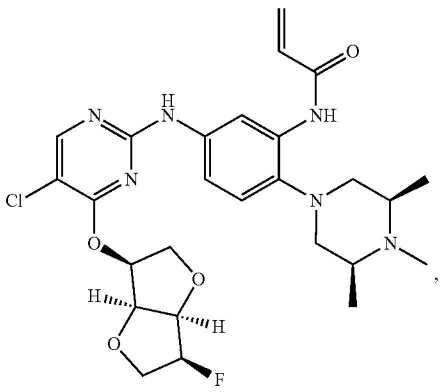
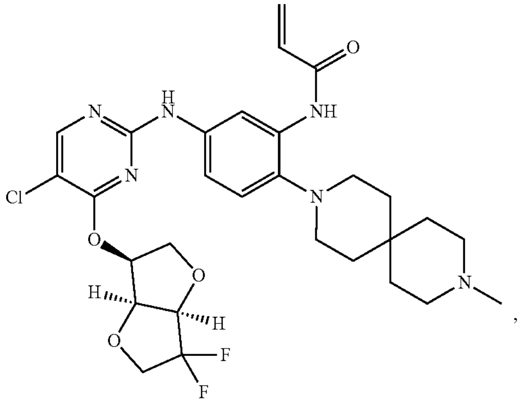
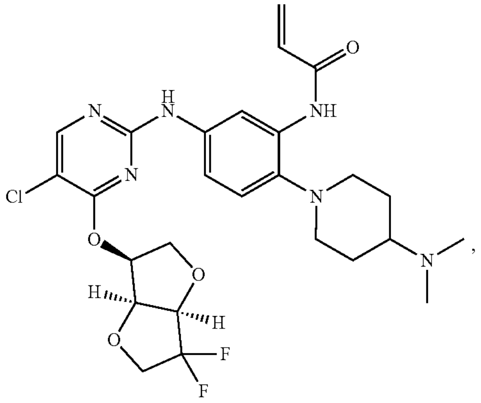
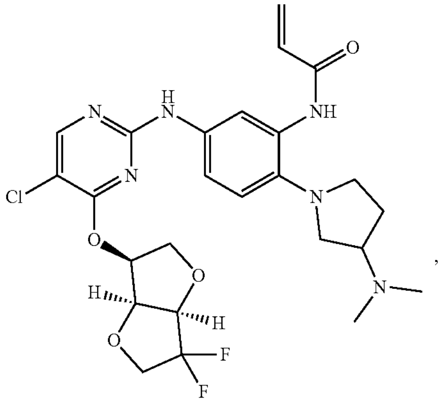
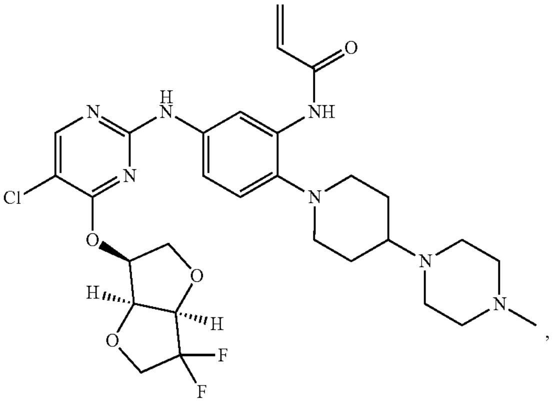
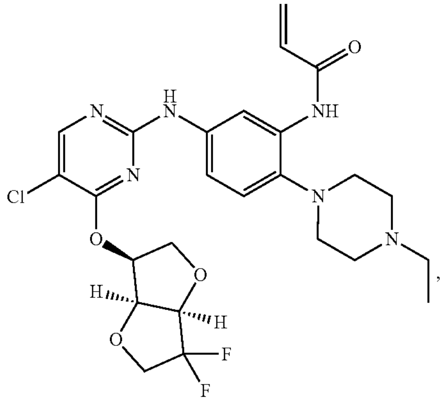
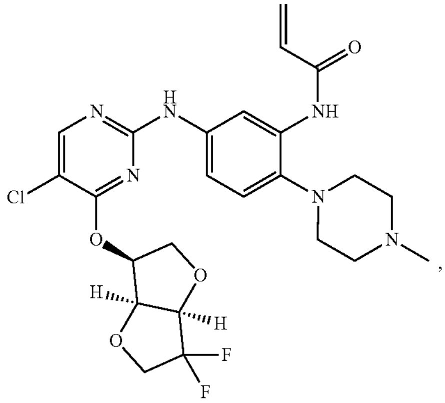
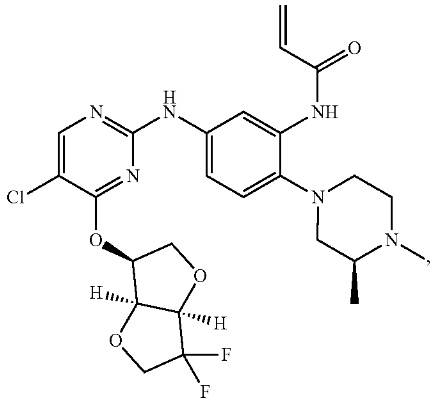
-continued -continued
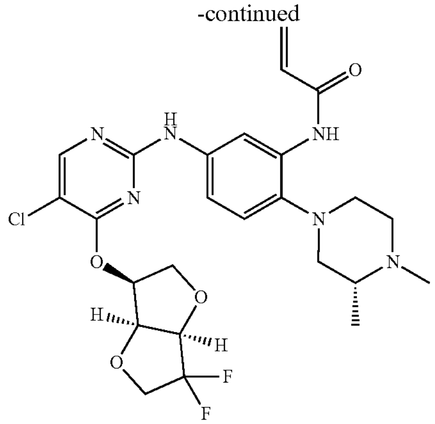
,
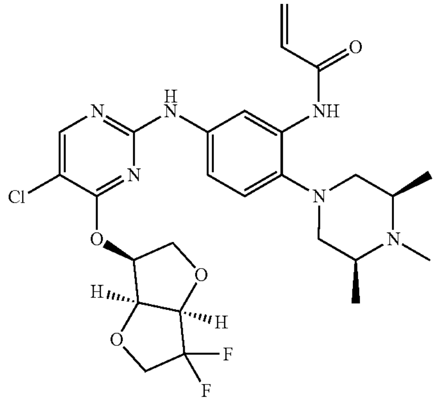
,
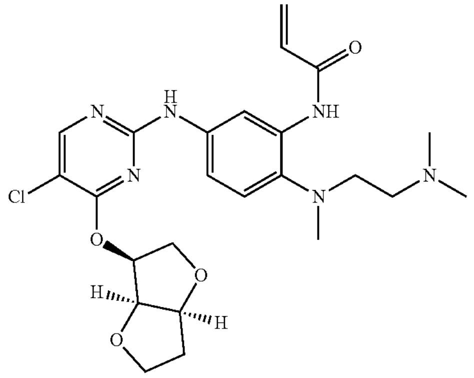
,
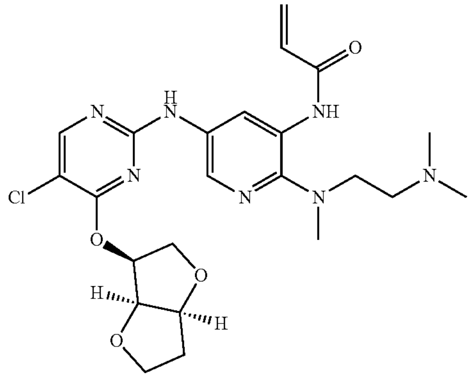
,
-continued
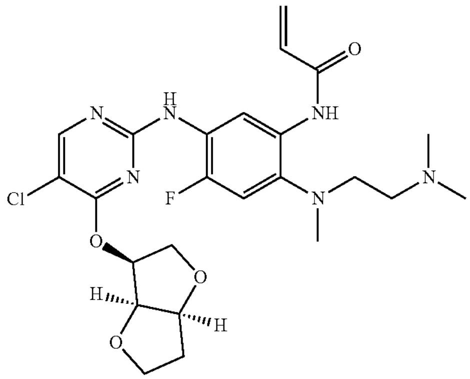
,
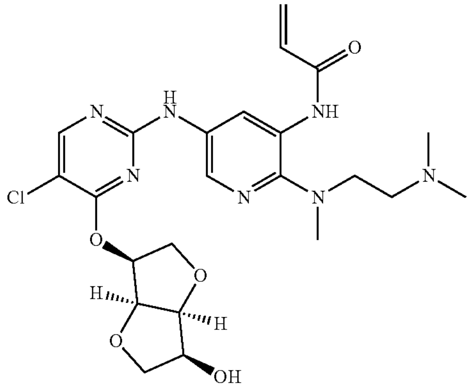
,
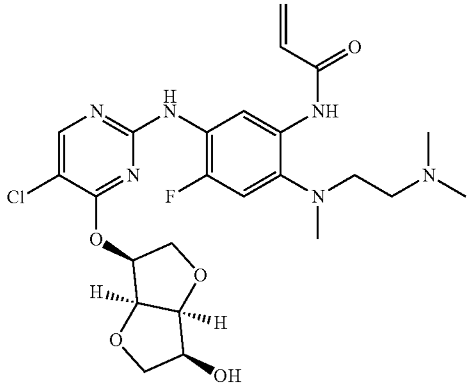
, -continued

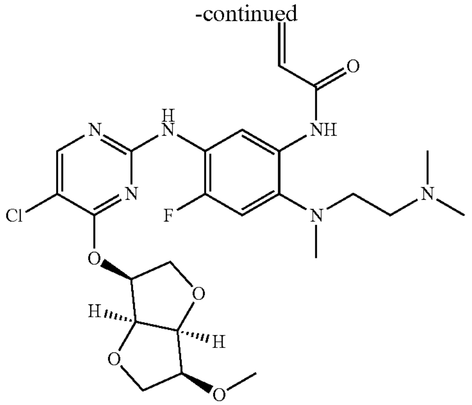

,

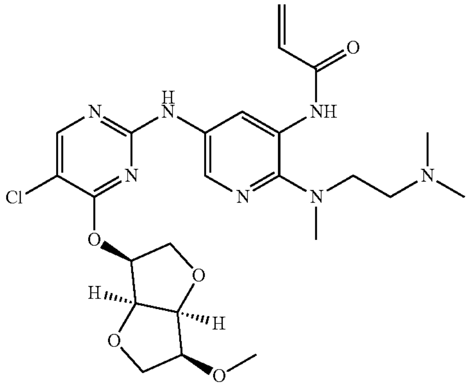

,

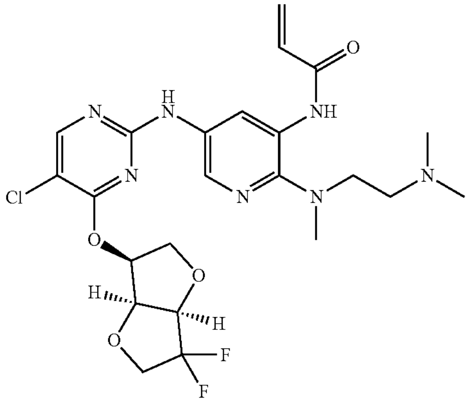

and

-continued

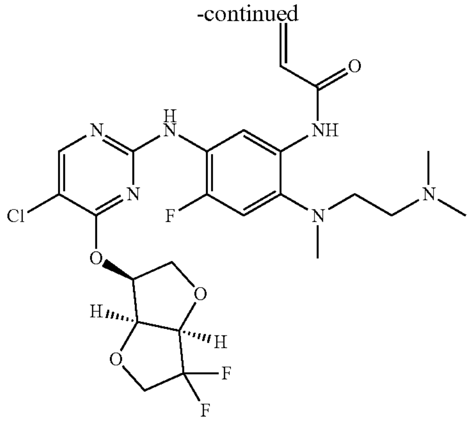

.

19. A pharmaceutical composition for preventing and treating tumors and/or inflammatory diseases, prepared from active ingredients and a pharmaceutically acceptable excipient and/or carrier, wherein the active ingredients comprise the 2-aminopyrimidine compound or pharmaceutically acceptable salt, solvate, or stereoisomer, geometric isomer, tautomer according to claim 1.

20. The pharmaceutical composition according to claim 19, wherein, the tumors are hematologic malignancies and solid tumors, and the hematologic malignancies are multiple myeloma, B-lymphoma, myelofibrosis, polycythemia vera, primary thrombocytosis, chronic myeloid leukemia, acute myeloid leukemia, acute lymphocytic leukemia, chronic myeloid leukemia, histiocyte lymphoma, acute megakaryocyte leukemia Juvenile lymphoblastic leukemia, T-lymphoblastic leukemia, and T-lymphoblastic lymphoma; the solid tumors are non small cell lung cancer, small cell lung cancer, lung adenocarcinoma, lung squamous cell cancer, pancreatic cancer, breast cancer, prostate cancer, liver cancer, skin cancer, epithelial cell cancer, gastrointestinal stromal tumor, nasopharyngeal carcinoma, and glioma; the inflammatory diseases are rheumatoid arthritis, atopic dermatitis, contact dermatitis, psoriasis, ulcerative colitis, Crohn's disease, eczema, discoid lupus erythematosus, systemic lupus erythematosus, alopecia areata, graft-versus-host disease, ankylosing spondylitis, diffuse systemic sclerosis of skin, and dermatomyositis.

* * * * *